United States Patent [19]

Nishimura et al.

[11] Patent Number: 4,839,351
[45] Date of Patent: Jun. 13, 1989

[54] ANTIBACTERIAL COMPOUNDS, AND USE

[75] Inventors: Tatsuo Nishimura, Toyonaka; Yoshinobu Yoshimura, Ibaraki; Akio Miyake, Hirakata; Naoto Hashimoto, Suita, all of Japan

[73] Assignee: Takeda Chemical Industries, Ltd., Japan

[21] Appl. No.: 941,069

[22] Filed: Dec. 12, 1986

[30] Foreign Application Priority Data

Dec. 13, 1985 [JP] Japan .................................. 60-281724

[51] Int. Cl.⁴ .................. C07D 501/36; A61K 31/545
[52] U.S. Cl. ..................................... 514/206; 540/227; 540/225; 514/203
[58] Field of Search ................ 514/206, 203; 540/225, 540/227, 222

[56] References Cited

U.S. PATENT DOCUMENTS

| | | | |
|---|---|---|---|
| 3,813,391 | 5/1974 | Naito et al. | 260/243 C |
| 3,814,755 | 6/1974 | Naito et al. | 260/243 C |
| 3,907,786 | 9/1975 | Naito et al. | 260/243 C |
| 3,946,000 | 3/1976 | Naito et al. | 260/243 C |
| 4,317,907 | 3/1982 | Saikawa et al. | 544/21 |
| 4,331,666 | 5/1982 | Nannini et al. | 424/246 |
| 4,358,448 | 11/1982 | Perrone | 424/246 |
| 4,385,178 | 5/1983 | Saikawa et al. | 544/26 |
| 4,388,314 | 6/1983 | Nannini et al. | 540/226 |
| 4,463,003 | 7/1984 | Takaya et al. | 424/246 |

FOREIGN PATENT DOCUMENTS 0150507 7/1985 European Pat. Off. .
1599469 7/1981 United Kingdom .

Primary Examiner—Nicholas S. Rizzo
Attorney, Agent, or Firm—Wegner & Bretschneider

[57] ABSTRACT

A compound of the general formula:

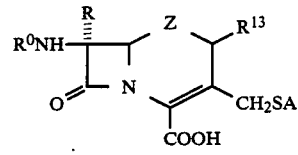

wherein $R^0$ is hydrogen, a nitrogen-containing heterocyclic group, an acyl group or an amino-protective group; A is S, S→O, O or $CH_2$; $R^4$ is hydrogen, methoxy group or formamido group; $R^{13}$ is hydrogen, methyl, hydroxyl or a halogen; and A is an optionally substituted condensed cyclic group formed by combining an imidazole or pyrazole ring with 5- or 6-membered nitrogen-containing aromatic heterocyclic ring to share a C-N bond with each other, or a salt or ester thereof.

and a process for preparing the same and a pharmaceutical composition thereof are disclosed.

12 Claims, No Drawings

ANTIBACTERIAL COMPOUNDS, AND USE

This invention relates to novel antimicrobial compounds having an excellent antimicrobial activity and to methods for the production and pharmaceutical compositions thereof.

More specifically this invention relates to a compound of the general formula:

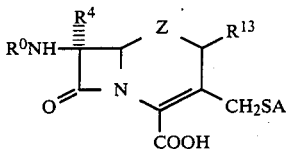

wherein $R^0$ is hydrogen, a nitrogen-containing heterocyclic group, an acyl group or an amino-protective group; Z is S, S→O, O or $CH_2$; $R^4$ is hydrogen, methoxy or formamido; $R^{13}$ is hydrogen, methyl, hydroxyl or a halogen; and A is an optionally substituted condensed cyclic group formed by combining an imidazole or pyrazole ring with a 5- or 6-membered nitrogen-containing aromatic heterocyclic ring to share a C—N bond with each other, or a salt or ester thereof, and to a process for preparing the same and a pharmaceutical composition thereof.

Hereinafter, unless otherwise mentioned, the compound (I) in this specification includes a salt or ester thereof.

The cephem compounds described in this specification are named according to "Cepham" described in "The Journal of the American Chemical Society" Vol. 84, p. 3400 (1962), and a cephem compound means a cepham compound having a double bond at the 3,4-position in the molecule.

Various cephem compounds having each a nitrogen-containing heterocyclic thiomethyl group at the 3 position and their derivatives have hitherto been synthesized, and applications for patent thereon have been filed. However only a few compounds in which a nitrogen-containing heterocyclic ring is a condensed ring have been synthesized and the condensed ring has been limited to the one formed by condensation between triazole or tetrazole and another heterocyclic ring (for example, U.S. Pat. Nos. 3,813,391, 3,814,755, 3,907,786, 3,946,000, 4,317,907, 4,385,178, G.B. Pat. No. 1,599,469, U.S. Pat. Nos. 4,331,666, 4,358,448, 4,463,003, EP No. 150,507, etc.). In such patent specifications, there have neither been synthesized, nor disclosed on compounds which contain an optionally substituted condensed cyclic group formed by combining an imidazole or pyrazole ring with a 5- or 6-membered nitrogen-containing aromatic heterocyclic ring to share a C-N bond with each other, as the nitrogen-containing heterocyclic group in the nitrogen-containing heterocyclic thiomethyl group which is the substituent at the 3 position.

The present inventors have succeeded in synthesizing the compound of the general formula (I) having these chemical structural characteristics, and found from studies on the antibacterial activity and antibacterial spectra, that the compound (I) wherein $R^0$ is a nitrogen-containing heterocyclic group or an aryl group has an excellent antibacterial activity against various bacteria, for example, Gram-negative bacteria or Gram-positive bacteria thus completing this invention.

In the following the names of groups and the symbols used in this specification are described. Unless otherwise stated, the names of groups and symbols in this specification mean the following.

"Alkyl group" is desirably a straight-chain or branched lower alkyl group having 1 to 6 carbon atoms (hereinafter sometimes abbreviated as "$C_{1-6}$ alkyl group"), such as methyl, ethyl, n-propyl, isopropyl, n-butyl, isobutyl, sec-butyl, tert-butyl n-pentyl or n-hexyl.

"Alkenyl group" is desirably a straight-chain or branched lower alkenly group having 2 to 6 carbon atoms (hereinafter sometimes abbreviated as "$C_{2-6}$ alkenyl group"), such as vinyl, allyl, 1-propenyl, isopropenyl, 1-butenyl, 2-butenyl, 3-butenyl, methallyl or 1,1-dimethylallyl.

"Alkynyl group" is desirably a straight-chain or branched lower alkynyl group having 2 to 6 carbon atoms (hereinafter sometimes abbreviated as "$C_{2-6}$ alkynyl group"), such as ethynyl, 1-propynyl or propargyl.

"Cycloalkyl group" is desirably a 3- to 7-membered alicyclic hydrocarbon group having 3 to 10 carbon atoms (hereinafter sometimes abbreviated as "$C_{3-10}$ cycloalkyl group"), such as cyclopropyl, cyclobutyl, cyclopentyl, cyclohexyl, cycloheptyl, norbornyl or adamantyl.

"Cycloalkenyl group" is desirably a 5- or 6-membered alicyclic hydrocarbon group having double bond(s) (hereinafter sometimes abbreviated as "$C_{5-6}$ cycloalkenyl group"), such as cyclopentenyl, cyclopentadienyl, cyclohexenyl or cyclohexadienyl.

"Aryl group" is desirably an aromatic hydrocarbon group having 6 to 12 carbon atoms (hereinafter sometimes abbreviated as "$C_{6-12}$ aryl group"), such as phenyl, naphthyl, β-naphthyl or biphenylyl, more preferably one having 6 to 10 carbon atoms (hereinafter sometimes abbreviated as "$C_{6-10}$ aryl group").

"Aralkyl group" is desirably an aromatically substituted alkyl group having 7 to 12 carbon atoms (hereinafter sometimes abbreviated as "$C_{7-12}$ aralkyl group"), such as benzyl, 1-phenylethyl, 2-phenylethyl, phenylpropyl or naphthylmethyl. Sometimes $C_{7-12}$ aralkyl group in combination with a di-$C_{6-10}$ aryl-methyl group and a tri-$C_{6-10}$ aryl-methyl group which are described below is altogether described as "$C_{7-19}$ aralkyl group".

"Diarylmethyl group" means a methyl group substituted with two $C_{6-10}$ aryl groups described above (hereinafter sometimes abbreviated as "di-$C_{6-10}$ aryl-methyl group"), such as benzhydryl.

"Triarylmethyl group" means a methyl group substituted with three $C_{6-10}$ aryl groups described above (hereinafter sometimes abbreviated as "tri-$C_{6-10}$ aryl-methyl group"), such as trityl.

The aryl group in "arylmethylene group" is desirably the $C_{6-10}$ aryl group described above, and therefore "arylmethylene group" is sometimes abbreviated as "$C_{6-10}$ arylmethylene group" hereinafter. Examples of the $C_{6-10}$ arylmethylene group include benzylidene ($C_6H_5CH=$).

The alkyl group in "alkoxy group" is desirably the $C_{1-6}$ alkyl group described above, and therefore "alkoxy group" is sometimes abbreviated as "$C_{1-6}$ alkoxy group" hereinafter. Examples of the $C_{1-6}$ alkoxy group include methoxy, ethoxy, n-propoxy, isopropoxy, n-butoxy, tert-butoxy, pentyloxy and hexyloxy.

The cycloalkyl group in "cycloalkyloxy group" is desirably the $C_{3-10}$ cycloalkyl group described above, and therefore "cycloalkyloxy group" is sometimes abbreviated as "$C_{3-10}$ cycloalkyloxy group" hereinafter. Examples of the $C_{3-10}$ cycloalkyloxy group include cyclopropyloxy, cylcopentyloxy, cyclohexyloxy and norbornyloxy.

The aryl group in "aryloxy group" is desirably the $C_{6-10}$ aryl group described above, and therefore "aryloxy group" is sometimes abbreviated as "$C_{6-10}$ aryloxy group" hereinafter. Examples of the $C_{6-10}$ aryloxy group include phenoxy and naphthyloxy.

The aralyl group in "aralkyloxy group" is desirably the $C_{7-19}$ aralkyl group described above, and therefore "aralkyloxy group" is sometimes abbreviated as "$C_{7-19}$ aralkyloxy group" hereinafter. Examples of the $C_{7-19}$ aralkyloxy group include benzyloxy, 1-phenylethyloxy, 2-phenylethyloxy, naphthylmethyloxy, benzhydryloxy and trityloxy.

The alkyl group in "alkylthio group" is desirably the $C_{1-6}$ alkyl group, and therefore "alkylthio group" is sometimes abbreviated as "$C_{1-6}$ alkylthio group" hereinafter. Examples of the $C_{1-6}$ alkylthio group include methylthio, ethylthio, n-propylthio and n-butylthio.

The alkylthio group in "aminoalkylthio group" is desirably the $C_{1-6}$ alkylthio group described above, and therefore "aminoalkylthio group" is sometimes abbreviated as "amino-$C_{1-6}$ alkylthio group" hereinafter. Examples of the amino-$C_{1-6}$ alkylthio group include aminomethylthio, 2-aminoethylthio and 3-aminopropylthio.

The alkenyl group in "alkenylthio group" is desirably the $C_{2-6}$ alkenyl group described above, and therefore "alkenylthio group" is sometimes abbreviated as "$C_{2-6}$ alkenylthio group" hereinafter. Examples of the $C_{2-6}$ alkenylthio group include vinylthio, allylthio, 1-propenylthio and isopropenythio.

The cycloalkyl group in "cycloalkylthio group" is desirably the $C_{3-10}$ cycloalkyl group described above, and therefore "cycloalkylthio group" is sometimes abbreviated as "$C_{3-10}$ cycloalkylthio group" hereinafter. Examples of the $C_{3-10}$ cycloalkylthio group include cyclopropylthio and cyclohexylthio.

The aryl group in "arylthio group" is desirably the $C_{6-10}$ aryl group described above, and therefore "arylthio group" is sometimes abbreviated as "$C_{6-10}$ arylthio group" hereinafter. Examples of the $C_{6-10}$ arylthio group include phenylthio and naththylthio.

The aralkyl group in "aralkylthio group" is desirably the $C_{7-19}$ aralkyl group described above, and therefore "aralkylthio" is sometimes abbreviated as "$C_{7-19}$ aralkylthio group" hereinafter. Examples of the $C_{7-1}$ aralkylthio group include benzylthio, phenylethylthio, benzhydrylthio and tritylthio.

The alkyl group in "monoalkylamino group" is desirably the $C_{1-6}$ alkyl group described above, and therefore "monoalkylamino group" is sometimes abbreviated as "mono-$C_{1-6}$ alkylamino group" hereinafter. Examples of the mono-$C_{1-6}$ alkylamino group include methylamino, ethylamino, n-propylamino, n-butylamino, tert-butylamino, n-pentylamino and n-hexylamino.

The alkyl group in "di-alkylamino group" is desirably the $C_{1-6}$ alkyl group described above, and therefore "dialkylamino group" is sometimes abbreviated as "di-$C_{1-6}$ alkyl group" hereinafter. Examples of the di-$C_{1-6}$ alkylamino group include dimethylamino, diethylamino, methylethylamino, di-(n-propyl)amino and di-(n-butyl)amino.

The alkyl group in "tri-alkylammonium group" is desirably the $C_{1-6}$ alkyl group described above, and therefore "tri-alkylammonium group" is sometimes abbreviated as "tri-$C_{1-6}$ alkylammonium group" hereinafter. Examples of the tri-$C_{1-6}$ alkylammonium group include trimethylammonium $(CH_3)_3N^+$ and triethylammonium. The tri-alkylammonium group is always accompanied by a corresponding anion. Examples of the anions include a halogenide ion (chloride ion, bromide ion, iodide ion, etc.), sulfate ion, nitrate ion, carbonate ion, an organic carboxylate ion (e.g. oxalate ion, trifluoroacetate ion), and an organic sulfonate ion (e.g. methanesulfonate ion, p-toluenesulfonate ion). The organic carboxylate ion and the organic sulfonate ion may form intramolecular salts.

The cycloalkyl group in "cycloalkylamino group" is desirably the $C_{3-10}$ cycloalkyl group described above, and therefore "cycloalkylamino group" is sometimes abbreviated as "$C_{3-10}$ cycloalkylammonio group" hereinafter. Examples of the $C_{3-10}$ cycloalkylamino group include cyclopropylamino, cyclopentylamino and cyclohexylamino.

The aryl group in "arylamino group" is desirably the $C_{6-10}$ aryl group described above, and therefore "arylamino group" is sometimes abbreviated as "$C_{6-10}$ arylamino group" hereinafter. Examples of the $C_{6-10}$ arylamino group include anilino and N-methylanilino.

The aralkyl group in "aralkylamino group" is desirably the $C_{7-19}$ aralkyl group described above, and therefore "aralkylamino group" is sometimes abbreviated as "$C_{7-19}$ aralkylamino group" hereinafter. Examples of the $C_{7-19}$ aralkylamino group include benzylamino, 1-phenylethylamino, 2-phenylethylamino, benzyldrylamino and tritylamino.

"Cyclic amino group" is a group which is formed by removing one of hydrogen atoms attached to the ring-constituting nitrogen atom of a nitrogen-containing heterocyclic ring or of a ring formed by saturation of the double bond(s) in the said nitrogen-containing heterocyclic ring, such as 1H-tetrazol-1-yl, 1H-pyrrol-1-yl, pyrrolino, pyrrolidino, 1H-imidazol-1-yl, imidazolino, imidazolidino, 1H-pyrazol-1-yl, pyrazolino, pyrazolidino, piperidino, piperazino, pyrazino and morpholino.

The alkyl group in "hydroxyalkyl group" is desirably the $C_{1-6}$ alkyl group described above, and therefore "hydroxyalkyl group" is sometimes abbreviated as "hydroxy $C_{1-6}$ alkyl group" hereinafter. Examples of the hydroxyl $C_{1-6}$ alkyl group include hydroxymethyl, 1-hydroxyethyl, 2-hydroxyethyl and 3-hydroxypropyl.

The alkyl group in "mercaptoalkyl group" is desirably the $C_{1-6}$ group described above, and therefore "mercaptoalkyl group" is sometimes abbreviated as "mercapto $C_{1-6}$ alkyl group" hereinafter. Examples of the mercapto $C_{1-6}$ alkyl group include mercaptomethyl, 1-mercaptoethyl and 2-mercaptoethyl.

The alkoxy group and the alkyl group in "alkoxyalkyl group" are desirably the $C_{1-6}$ alkoxy group and the $C_{1-6}$ alkoxy roup described above, respectively, and therefore "alkoxyalkyl group" is sometimes abbreviated as "$C_{1-6}$ alkoxy $C_{1-6}$ alkyl group" hereinafter. Examples of the $C_{1-6}$ alkoxy $C_{1-6}$ alkyl group include methoxymethyl, ethoxymethyl and 2-methoxyethyl.

The alkylthio group and the alkyl group in "alkylthioalkyl group" are desirably the $C_{1-6}$ alkylthio group and the $C_{1-6}$ alkyl group described above, respectively, and therefore "alkylthioalkyl group" is sometimes abbreviated as "$C_{1-6}$ alkylthio $C_{1-6}$ alkyl group" hereinafter. Examples of the $C_{1-6}$ alkylthio $C_{1-6}$ alkyl group include methylthiomethyl and 2-methylthioethyl.

The alkyl group in "aminoalkyl group" is desirably the $C_{1-6}$ alkyl group described above, and therefore "aminoalkyl group" is sometimes abbreviated as "amino $C_{1-6}$ alkyl group" hereinafter. Examples of the amino $C_{1-6}$ alkyl group include aminomethyl, 2-aminoethyl and 3-aminopropyl.

"Monoalkylaminoalkyl group" is desirably "mono-$C_{1-6}$ alkylamino $C_{1-6}$ alkyl group", including methylaminomethyl, ethylaminomethyl, 2-(N-methylamino)ethyl and 3-(N-methylamino) propyl.

"Dialkylaminoalkyl group" is desirably "di-$C_{1-6}$ alkylamino $C_{1-6}$ alkyl group", including N,N-dimethylaminomethyl, N,N-diethylaminomethyl, 2-(N,N-dimethylamino)ethyl, 2-(N,N-diethylamino)ethyl and 3-(N,N-dimethylamino)propyl.

The cyclic amino group and the alkyl group in "cyclic aminoalkyl group" are desirably the one described above and the $C_{1-6}$ alkyl group described above, respectively, and therefore "a cyclic aminoalkyl group" is sometimes abbreviated as "cyclic amino $C_{1-6}$ alkyl group" hereinafter. Examples of the cyclic amino $C_{1-6}$ alkyl group include pyrrolidinomethyl, piperidinomethyl, piperazinomethyl, morpholinomethyl and 2-(morpholino)ethyl.

The cyclic aminoalkyl group in "cyclic aminoalkylamino group" is desirably the cyclic amino $C_{1-6}$ alkyl group described above, and therefore "cyclic aminoalkylamino group" is sometimes abbreviated as "cyclic amino $C_{1-6}$ alkylamino group" hereinafter. Examples of the cyclic amino $C_{1-6}$ alkylamino group include pyrrolidinomethylamino, piperidinomethylamino, piperazinomethylamino and morpholinomethylamino.

The alkyl group in "haloganoalkyl group" is desirably the $C_{1-6}$ alkyl group described above, and therefore "halogenoalkyl group" is sometimes abbreviated as "halogeno $C_{1-6}$ alkyl group" hereinafter. Examples of the halogeno $C_{1-6}$ alkyl group include fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl and 2-iodoethyl.

The alkyl group in "cyanoalkyl group" is desirably the $C_{1-6}$ alkyl group described above, and therefore "a cyanoalkyl group" is sometimes abbreviated as "cyano $C_{1-6}$ alkyl group" hereinafter. Examples of the cyano $C_{1-6}$ alkyl group include cyanomethyl and 2-cyanoethyl.

The alkyl group in "carboxyalkyl group" is desirably the $C_{1-6}$ alkyl group described above, and therefore "carboxyalkyl group" is sometimes abbreviated as "carboxy $C_{1-6}$ alkyl group" hereinafter. Examples of the carboxy $C_{1-6}$ alkyl group include carboxymethyl, 1-carboxyethyl and 2-carboxyethyl.

The alkyl group in "sulfoalkyl group" is desirably the $C_{1-6}$ alkyl group described above, and therefore "sulfoalkyl group" is sometimes abbreviated as "sulfo $C_{1-6}$ alkyl group" hereinafter. Examples of the sulfo $C_{1-6}$ alkyl group include sulfomethyl and 2-sulfoethyl.

The alkanoyl group and the alkyl group in "alkanoylalkyl group" is desirably the $C_{2-6}$ alkanoyl group described below and the $C_{1-6}$ alkyl group described above, respectively and therefore "alkanoylalkyl group" is sometimes abbreviated as "$C_{2-6}$ alkanoyl $C_{1-6}$ alkyl group" hereinafter. Examples of the $C_{2-6}$ alkanoyl $C_{1-6}$ alkyl group include acetylmethyl, 1-acetylethyl and 2-acetylethyl.

The alkanoyloxy group and the alkyl group in "alkanoyloxyalkyl group" is desirably the $C_{2-6}$ alkanoyloxy group described below and the $C_{1-6}$ alkyl group described above, respectively, and therefore "alkanoyloxyalkyl group" is sometimes abbreviated as "$C_{2-6}$ alkanoyloxy $C_{1-6}$ alkyl group" hereinafter. Examples of the $C_{2-6}$ alkanoyloxy $C_{1-6}$ alkyl group include acetoxymethyl, 1-acetoxyethyl and 2-acetoxyethyl.

The alkoxycarbonyl group and an alkyl group in "alkoxycarbonylalkyl group" is desirably the $C_{1-10}$ alkoxy-carbonyl group described below and the $C_{1-6}$ alkyl group described above, respectively, and therefore "alkoxycarbonylalkyl group" is sometimes abbreviated as "$C_{1-10}$ alkoxy-carbonyl-$C_{1-6}$ alkyl group. Examples of the $C_{1-10}$ alkoxy-carbonyl-$C_{1-10}$ alkyl group include methoxycarbonylmethyl, ethoxycarbonylmethyl and tert-butoxycarbonylmethyl.

The alkyl group in "carbamoylalkyl group" is desirably the $C_{1-6}$ alkyl group described above, and therefore "carbamoyalkyl group" is sometimes abbreviated as "carbamoyl $C_{1-6}$ alkyl group" hereinafter. An example of the carbamoyl $C_{1-6}$ alkyl group includes carbamoylmethyl.

The alkyl group in "carbamoyloxyalkyl group" is desirably the $C_{1-6}$ alkyl group described above, and therefore "carbamoyloxyalkyl group" is sometimes abbreviated as "carbamoyloxy $C_{1-6}$ alkyl group" hereinafter. An example of the carbamoyloxy $C_{1-6}$ alkyl group includes carbamoyloxymethyl.

"Halogen atom" is fluorine, chlorine, bromine or iodine.

"Alkanoyl group" is desirably an aliphatic acyl group having 1 to 6 carbon atoms (hereinafter sometimes abbreviated as "$C_{1-6}$ alkanoyl group"), such as formyl, acetyl, propionyl, butyryl, isobutyryl, valeryl, isovaleryl and pivaloyl. These alkanoyl groups except formyl are sometimes written as "$C_{2-6}$ alkanoyl group".

"Alkenoyl group" is desirably an alkenoyl group having 3 to 5 carbon atoms (hereinafter sometimes abbreviated as "$C_{3-5}$ alkenoyl group"), such as acryloyl, crotonoyl or maleoyl.

The cycloalkyl group in "acycloalkylcarbonyl group" is desirably the $C_{3-10}$ cycloalkyl group described above, and therefore "cycloalkylcarbonyl group" is sometimes abbreviated as "$C_{3-10}$ cycloalkenyl-carbonyl group" hereinafter. Examples of the $C_{3-10}$ cyclocalkyl-carbonyl group include cyclopropylcarbonyl, cyclobutylcarbonyl, cyclopentylcarbonyl, cyclohexylcarbonyl, cycloheptylcarbonyl and adamantylcarbonyl.

The cycloalkenyl group in "cycloalkenylcarbonyl group" is desirably the $C_{5-6}$ cycloalkyl group described above, and therefore "cycloalkenylcarbonyl group" is sometimes abbreviated as "$C_{5-6}$ cycloalkenyl-carbonyl group" hereinafter. Examples of the $c_{5-6}$ cycloalkenyl-carbonyl group include cyclopentenylcarbonyl, cyclopentadienylcarbonyl, cyclohexenylcarbonyl and cyclohexadienylcarbonyl.

The aryl group in "arylcarbonyl group" is desirably the $C_{6-10}$ aryl group described above, and therefore "arylcarbonyl group" is sometimes abbreviated as "$C_{6-10}$ aryl-carbonyl group" hereinafter. Examples of the $C_{6-10}$ aryl-carbonyl group include benzoyl and naphthoyl.

The aralkyl group in "aralkylcarbonyl group" is desirably the $C_{7-19}$ aralkyl group described above, and therefore "aralkylcarbonyl group" is sometimes abbreviated as "$C_{7-19}$ aralkyl-carbonyl group" hereinafter. Examples of the $C_{7-19}$ aralkyl-carbonyl group include phenylacetyl, phenylpropionyl, α,α-diphenylacetyl and α,α,α-triphenylacetyl.

The alkyl group in "alkoxycarbonyl group" herein is defined to include not only a lower alkyl gorup having 1 to 8 carbon atoms but also the $C_{3-10}$ cycloalkyl group described above. Therefore "alkoxycarbonyl group" is sometimes abbreviated as "$C_{1-10}$ alkoxy-carbonyl group" hereinafter. Examples of the $C_{1-10}$ alkoxy-carbonyl group include methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl and norbornyloxycarbonyl.

The aryloxy group in "aryloxycarbonyl group" is desirably the $C_{6-10}$ aryloxy group described above, and therefore "aryloxycarbonyl group" is sometimes abbreviated as "$C_{6-10}$ aryloxy-carbonyl group" hereinafter. Examples of the $C_{6-10}$ aryloxy-carbonyl group include phenoxycarbonyl and naphthyloxycarbonyl.

The aralkyloxy group in "aralkyloxycarbonyl group" is desirably the $C_{7-19}$ aralkyloxy group described above. Examples of the $C_{7-19}$ aralkyloxy group include benzyloxycarbonyl, benzhydryloxycarbonyl and trityloxycarbonyl.

"Substituted oxycarbonyl group" means the $C_{1-10}$ alkoxy-carbonyl group, $C_{6-10}$ aryloxy-carbonyl group or $C_{7-19}$ aralkyloxy-carbonyl group described above.

The alkylthio group in "alkylthiocarbonyl group" is desirably the $C_{1-6}$ alkylthio group described above, and therefore "alkylthiocarbonyl group" is sometimes abbreviated as "$C_{1-6}$ alkylthio-carbonyl group" hereinafter. Examples of the $C_{1-6}$ alkylthio-carbonyl group include methylthiocarbonyl, ethylthiocarbonyl, n-propylthiocarbonyl and n-butylthiocarbonyl.

The alkanoyl group in "alkanoyloxy group" is desirably the $C_{1-6}$ alkanoyl group described above, and therefore "alkanoyloxy group" is sometimes abbreviated as "$C_{1-6}$ alkanoyloxy group" hereinafter. Examples of the $C_{1-6}$ alkanoyloxy group include formyloxy, acetoxy, propionyloxy, butyryloxy, valeryloxy and pivaloyloxy. The alkanoyloxy groups except formyloxy are sometimes written as "$C_{2-6}$ alkanoyloxy group".

The alkenoyl group in "alkenoyloxy group" is desirably the $C_{3-5}$ alkenoyl group described above, and therefore "alkenoyloxy group" is sometimes abbreviated as "$C_{3-5}$ alkenoyloxy group" hereinafter. Examples of the $C_{3-5}$ alkenoyloxy group include acryloyloxy and crotonoyloxy.

The alkyl group in "mono-alkylcarbamoyl group" is desirably the $C_{1-6}$ alkyl group described above, and therefore "monoalkylcarbamoyl group" is sometimes abbreviated as "mono-$C_{1-6}$ alkylcarbamoyl group" hereinafter. Examples of the mono-$C_{1-6}$ alkylcarbamoyl group include N-methylcarbamoyl and N-ethylcarbamoyl.

The alkyl group in "di-alkylcarbamoyl group" is desirably the $C_{1-6}$ alkyl group described above, and therefore "di-alkylcarbamoyl group" is sometimes abbreviated as "di-$C_{1-6}$ alkylcarbamoyl group" hereinafter. Examples of the di-$C_{1-6}$ alkylcarbamoyl group include N,N-dimethylcarbamoyl and N,N-diethylcarbamoyl.

The mono-alkylcarbamoyl group in "mono-alkylcarbamoyloxy group" is desirably the mono-$C_{1-6}$ alkylcarbamoyl group described above, and therefore "monoalkylcarbamoyloxy group" is sometimes abbreviated as "mono-$C_{1-6}$ alkylcarbamoyloxy group" hereinafter. Examples of the mono-$C_{1-6}$ alkylcarbamoyloxy group include N-methylcarbamoyloxy and N-ethylcarbamoyloxy.

The di-aralkylcarbamoyl group in "di-alkylcarbamoyloxy group" is desirably the di-$C_{1-6}$ alkylcarbamoyl group described above, and therefore "di-alkylcarbamoyloxy group" is sometimes abbreviated as "di-$C_{1-6}$ alkylcarbamoyloxy group" hereinafter. Examples of the di-$C_{1-6}$ alkylcarbamoyloxy group include N,N-dimethylcarbamoyloxy and N,N-diehtylcarbamoyloxy.

The alkyl group in "alkylsulfonyl group" is desirably the $C_{1-6}$ alkyl group described above, and therefore "alkylsulfonyl group" is sometimes abbreviated as "$C_{1-6}$ alkylsulfonyl group" hereinafter. Examples of the $C_{1-6}$ alkysulfonyl gorup include methanesulfonyl and ethanesulfonyl.

The aryl group in "arylsulfonyl group" is desirably the $C_{6-10}$ aryl group described above, and therefore "arylsulfonyl group" is sometimes abbreviated as "$C_{6-10}$ arylsulfonyl group" hereinafter. An example of the $C_{6-10}$ arylsulfonyl group includes benzenesulfonyl.

The aralkyl group in "aralkylsulfonyl group" is desirably the $C_{7-19}$ aralkyl group described above, and therefore "aralkylsulfonyl group" is sometimes abbreviated as "$C_{7-19}$ aralkylsulfonyl group" hereinafter. Examples of the $C_{7-19}$ aralkylsufonyl group include phenylmethanesulfonyl and diphenylmethanesulfonyl.

The alkylsulfonyl group in "alkylsulfonyloxy group" is desirably the $C_{1-6}$ alkylsufonyl group described above, and therefore "alkylsulfonyloxy group" is sometimes abbreviated as "$C_{1-6}$ alkylsulfonyloxy group" hereinafter. Examples of the $C_{1-6}$ alkylsulfonyloxy group include methanesulfonyloxy and ethanesulfonyloxy.

The arylsulfonyl group in "arylsulfonyloxy group" is desirably the $C_{6-10}$ arylsulfonyl group described above, and therefore "arylsulfonyloxy group" is sometiems abbreviated as "$C_{6-10}$ arylsulfonyloxy group" hereinafter. An example of the $C_{6-10}$ arylsulfonyloxy group include benzenesulfonyloxy.

The aralkylsulfonyl group in "aralkylsulfonyloxy group" is desirably the $C_{7-19}$ aralkylsulfonyl group described above, and therefore "aralkylsulfonyloxy group" is sometimes abbreviated as "$C_{7-19}$ arylkylfulsonyloxy group" hereinafter. Examples of the $C_{7-19}$ aralkylsulfonyloxy group include phenylmethanesulfonyloxy and diphenylmethanuesulfonyloxy.

"Amino acid residue" is an acyl group formed by removing a hydroxyl group from the carboxyl group in a usual amino acid, which is exemplified by glycyl, alanyl, valyl, leucyl, isoleucyl, seryl, threonyl, cysteinyl, cystyl, methionyl, asparaginyl, glutamyl, lysyl, arginyl, phenylglyclyl, phenylalanyl, tyrosyl, histidyl, tryptophyl or prolyl. The amino acid in such an amino acid residue includes not only L-form but also D-form.

"Nitrogen-containing heterocyclic ring" is a 5- or 8-membered ring containing one to several, preferably one to four nitrogen atoms (which may be oxidized) or a condensed ring thereof. Such a nitrogen-containing heterocyclic ring may contain, in addition to the nitrogen atom, one to several, preferably one or two hetero atoms, such as oxygen atom(s) or sulfur atom(s).

"Nitrogen-containing heterocyclic group" is a group formed by removing one of the hydrogen atoms attached to the ring-constituting carbon atoms of the nitrogen-containing heterocyclic ring described above.

"Heterocyclic group" is a group formed by removing one of the hydrogen atoms attached to the carbon atoms of the heterocyclic ring. Such a heterocyclic ring is a 5- or 8-membered ring containing one to several, preferably one to four hetero atoms, such as nitrogen atoms (which may be oxidized), oxygen atoms and sulfur atoms, or a condensed ring thereof. Examples of the heterocyclic group include 2- or 3-pyrrolyl, 3-, 4-, or 5-pyrazolyl, 2-, 4- or 5-imidazolyl, 1,2,3- or 1,2,4-triazolyl, 1H- or 2H-tetrazolyl, 2- or 3-furyl, 2- or 3-thienyl, 2-, 4- or 5- oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiadizol-4- or 5-yl, 1,2,4-thiadiazol-3- or 5-yl, 1,2,5- or 1,3,4-thiadiazolyl, 2- or 3-pyrrolidinyl, 2-, 3- or 4-pyridyl, 2-, 3- or 4-pyridyl-N-oxido, 3- or 4-pyridazinyl, 3- or 4-pyridazinyl-N-oxido, 2-, 4- or 5-pyrimidinyl, 2-, 4- or 5-pyrimidinyl-N-oxido, pyrazinyl, 2-, 3- or 4-piperidinyl, piperazinyl, 3H-indol-2- or 3-yl, 2-, 3- or 4-pyranyl, 2-, 3- or 4-thiopyranyl, benzopyranyl (e.g. benzopyran-3-yl), quinolyl (e.g. 2-quinolyl), pyrido[2,3-d]pyrimidinyl (e.g. pyrido[2,3-d]pyrimidin-2-yl), 1,5-, 1,6-, 1,7-, 1,8-, 2,6- or 2,7-naphthyridinyl (e.g. 1,8-naphthyridin-2-yl), thieno [2,3-d]pyridyl (e.g. thieno[2,3-d]pyridin-2-yl), pyrimidopyridyl (e.g. pyrimidopyridin-2-yl), and pyrazinoquinolyl (e.g. pyrazinoquinolin-2-yl).

The heterocyclic group in "heterocyclic oxy", "heterocyclic thio", "heterocyclic amino", "heterocyclic carbonyl", "heterocyclic acetyl" and "heterocyclic carboxamido" group is preferably the "heterocyclic group" described above.

"Quaternary ammonium group" is formed when the unpaired electron on a tertiary nitrogen atom (a member of the nitrogen-containing heterocyclic ring described above) is used to form a bond. Therefore the group is always accompanied by a corresponding anion. Examples of the quaternary ammonium group include oxazolium, thiazolium, isoxazolium, isothiazolium, pyridinium and quinolinium. Examples of the anion include hydroxide, halide (chloride, bromide or iodide ion), sulfate, nitrate, carbonate, an organic carboxylate (e.g. an oxalate or trifluoroacetate ion) or an oganic sulfonate ion (e.g. a p-toluenesulfonate ion). An organic carboxylate ion and organic sulfonate ion may be intramolecular.

The groups marked with * on the right shoulder are "the groups which may be substituted". For example, the alkyl* group means "alkyl group which may be substituted". The number of the substituents is not necessarily limited to one, but, according to the kind of the substituent, there may be two to several, preferably 2 or 3, which may be the same or defferent.

"$C_{6-10}$ aryl*", "$C_{7-19}$ aralkyl*", "$C_{6-10}$ aryl*oxy" and "$C_{7-19}$ aralkyl*oxy" groups are preferably "phenyl*", "benzyl*", "phenoxy*", and "benzyl*oxy" groups, respectively.

In the compound (I) of this invention, the substituent $R^0$ is hydrogen, a nitrogen-containing heterocyclic group, an acyl group or an amino-protective group. Among these, the compounds (I) wherein the substituent $R^0$ is a nitrogen-containing heterocyclic group or the compounds (I) wherein $R^0$ is an acyl group are antibacterial compounds which have strong and broad antibacterial activities and also a strong antibacterial activity particulary against cephalosporin-resistant bacteria. The compounds (I) wherein the substituent $R^0$ is hydrogen or the compounds (I) wherein $R^0$ is an aminoprotective group are useful as the intermediates in the production of the compounds (I) described above wherein the substituent $R^0$ is a nitrogen-containing heterocyclic group or an acyl group.

The nitrogen-containing heterocyclic group as the substituent $R^0$ (hereinafter sometimes represented by the symbol $R^a$) is the "nitrogen-containing heterocyclic group" described above, such as 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,3-triazolyl, 1,2,4-triazolyl, 1H-tetrazolyl (e.g. 1H-tetrazol-5-yl), 2H-tetrazolyl (e.g. 2H-tetrazol-5-yl), 2-oxazolyl, 4-oxazolyl, 5-oxazolyl, 3-isoxazolyl, 4-isoxazolyl, 5-isoxazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazolyl, 1,3,4-oxadiazolyl, 2-thiazolyl, 4-thiazolyl, 5-thiazolyl, 3-isothiazolyl, 4-isothiazolyl, 5-isothiazolyl, 1,2,3-thiadiazol-4-yl, 1,2,3-thiadiazol-5-yl, 1,2,4-thiadiazol-3-yl, 1,2,4-thiadiazol-5-yl, 2,5-thiadiazolyl, 1,3,4-thiadiazolyl, 2-pyrrolidinyl, 3pyrrolidinyl, 2-pyridiyl, 3-pyridyl, 4-pyridyl, 2-pyridyl-N-oxido, 3-pyridyl-N-oxido, 4-pyridyl-N-oxido, 3-pyridazinyl, 4-pyridazinyl, 3-pyridazinyl-N-oxido, 4-pyridazinyl-N-oxido, 2-pyrimidinyl, 4-pyrimidinyl, 5-pyrimidinyl, 2-pyrimidinyl-N-oxido, 4-pyrimidinyl-N-oxido, 5-pyrimidinyl-N-oxido, pyrazinyl, 2-piperidinyl, 3-piperidinyl, 4-piperidinyl, piperazinyl, 3H-indol-2-yl or 3H-indol-3-yl. Among them, 2-pyridyl, 3-pyridyl, 4-pyridyl, 2-imidazolyl, 4-imidazolyl or 5-imidazolyl is preferable.

The nitrogen-containing heterocyclic group described above may be substituted on the ring. The number of the substituents is not necessarily limited to one, but there may be two to several, preferably 2 or 3 substituents, which may be the same or different. Examples of the substituent on the nitrogen-containing heterocyclic ring include an alkyl group, a cycloalkyl group, an aryl group, an aralkyl group, hydroxyl, an alkoxy group, mercapto, an alkylthio group, amino, a monoalkyl amino group, a dialkylamino group, halogen, nitro, azido, cyano, carboxyl, an alkoxycarbonyl group, an alkanoyl group, an alkanoyloxy group, carbamoyl, a mono-alkylcarbamoyl group, a di-alkylcarbamoyl group, carbamoyloxy, a mono-alkylcarbamoyloxy group and a di-alkylcarbamoyloxy group.

As for the substituted nitrogen-containing heterocyclic groups, a 2-imidazolyl group substituted by an alkyl group, an aryl group or halogen as described above, or a N-substituted pyridinium-4-yl group which is derived from a 4-pyridyl group by substitution at the nitrogen atom with an alkyl or aralkyl group or the like described above and thereby the nitrogen atom itself is quaternized is preferable. Examples of the 2-imidazolyl group include 1-methyl-2-imidazolyl and 4-chloro-2-imidazolyl, and examples of the N-substituted pyridinium-4-yl group include N-methylpyridinium-4-yl, N-ethylpyridinium-4-yl, N-benzylpyridinium-4-yl and N-(p-fluorobenzyl)pyridinium-4-yl.

The acyl group as the substituent $R^0$ (hereinafter sometimes represented by the symbol $R^b$) means the acyl group substituting the amino group at the 6 position in the known penicillin derivatives, and the acyl group substituting the amino group at the 7 position in the known cephalosporin derivatives, and the like. Examples of the acyl group include an alkanoyl group, an alkenoyl group, cycloalkylcarbonyl group, a cycloalkenylcarbonyl group, an arylcarbonyl group and a heterocyclic carbonyl group; more specifically they are a $C_{1-6}$alkanoyl* group, a $C_{3-5}$alkenoyl* group, a $C_{3-10}$ cycloalkyl-carbonyl group, a $C_{5-6}$ cycloalkenylcarbonyl group, a $C_{6-10}$ aryl*carbonyl group and a heterocyclic*-carbonyl group, respectively.

Examples of the $C_{1-6}$ alkanoyl group include formyl, acetyl, propionyl, butyryl, isobutyryl, valeryl, isovaleryl and pivaloyl.

Examples of the substituents in "$C_{1-6}$ alkanoyl group which may be substituted" represented by a $C_{1-6}$alkanoyl* group include a heterocyclic* group in the case of a $C_1$ alkanoyl group (i.e. formyl), and "substituent $S^1$" described below in the case of a $C_{2-6}$ alkanoyl group (i.e. acetyl, propionyl, butyryl, isobutyryl, valeryl, isovaleryl or pivaloyl). The "substituent $S^1$" is a $C_{3-10}$ cycloalkyl* group, a $C_{5-6}$ cycloalkenyl* group, a $C_{6-10}$ aryl* group, hydroxyl, a $C_{1-6}$ alkoxy group, a $C_{3-10}$ cycloalkyloxy group, a $C_{6-10}$ aryl*oxy group, a $C_{7-19}$ aralkyl*oxy group, mercapto, a $C_{1-6}$ alkyl*thio group, an amino$C_{1-6}$ alkylthio group, a $C_{2-6}$ alkenyl*thio group, a $C_{3-10}$-cycloalkylthio group, a $C_{6-10}$ aryl*thio group, a $C_{7-19}$ aralkyl*thio group, amino, a mono-$C_{1-6}$alkylamino group, a di-$C_{1-6}$ alkylamino group, a $C_{3-10}$ cycloalkylamino group, a $C_{6-10}$ aryl*amino group, a $C_{7-19}$ aralkyl*amino group, a cyclic amino* group, halogen, nitro, azido, cyano, carboxyl, an acyl+ group, a substituted oxycarbonyl group, a $C_{1-6}$ alkylthio-carbonyl group, an acyl+ amino group, an acyl+ aminoalkylthio group, carbamoyl, a mono-$C_{1-6}$-alkylcarbamoyl group, a di-$C_{1-6}$ alkylcarbamoyl group, carbamoyloxy, a mono-$C_{1-6}$alkylcarbamoyloxy group, a di-$C_{1-6}$ alkylcarbamoyloxy group, sulfo, hydroxysulfonyloxy, a $C_{1-6}$-alkylsulfonyl group, a $C_{6-10}$aryl*sulfonyl group, a $C_{7-19}$-aralkyl*sulfonyl group, a $C_{1-6}$ alkylsulfonyloxy group, a $C_{6-10}$-aryl*sulfonyloxy group, a $C_{7-19}$-aralkyl*sulfonyloxy group, ureido*, sulfamoyl*, a heterocyclic* group, a heterocyclic*oxy group, a heterocyclic*thio group, a heterocyclic*amino, a heterocyclic*carbonyl group, heterocyclic*carboxamido group or a quaternary ammonium* group. The number of the substituents is not restricted to one, preferably one to four and when there are two to four substituents, the substituents may be the same or different. Two of these substituents may form together a C=C bond or a C=N bond described later.

Examples of the substituents in "a $C_{3-5}$alkenoyl group which may be substituted" represented by a $C_{3-5}$ alkenoyl* group (hereinafter described as "a substituent $S_2$") include a $C_{3-10}$ cycloalkyl group, a $C_{6-10}$aryl* group, a $C_{1-6}$alkoxy group, a $C_{6-10}$ aryl*oxy group, a $C_{7-19}$ aralkyl*oxy group, halogen, cyano, carboxyl, an acyl+ group, a substituted oxycarbonyl group, an acyl+ oxy group, a heterocyclic* group, and a quaternary ammonium* group.

The substituents in "$C_{6-10}$ aryl-carbonyl group which may be substituted" represented by $C_{6-10}$ aryl*carbonyl group and the substituents in "heterocyclic carbonyl group which may be substituted" represented by heterocyclic*carbonyl group (hereinafter, both substituents are represented by substituent $S^3$") include a $C_{1-6}$ alkyl group, a $C_{2-6}$ alkenyl group, a $C_{6-10}$ aryl group, a $C_{7-12}$ aralkyl group, a di-$C_{6-10}$-aryl-methyl group, a tri-$C_{6-10}$arylmethyl group, hydroxyl, a $C_{1-6}$alkoxy group, a $C_{6-10}$ aryloxy group, a $C_{7-19}$ aralkyloxy group, mercapto, a $C_{1-6}$ alkylthio group, a $C_{6-10}$arylthio group, a $C_{7-19}$ aralkylthio group, amino, a mono-$C_{1-6}$alkylamino group, a di-$C_{1-6}$alkylamino group, a hydroxy$C_{1-6}$ alkyl group, a mercapto$C_{1-6}$alkyl group, a halogeno$C_{1-6}$alkyl group, a carbox$C_{1-6}$ alkyl group, halogen, nitro, azido, cyano, carboxyl, a substituted oxycarbonyl, an acyl+ group, an acyl+ oxy group, acyl+ amino group, carbamoyl, thiocarbamoyl, a $C_{1-6}$ alkylsulfonyl group, a $C_{6-10}$ arylsulfonyl group and a $C_{7-19}$ aralkylsulfonyl group.

To the substituents ($S^1$, $S^2$ and $S^3$) described above for the $C_{1-6}$ alkanoyl group, $C_{3-5}$ alkenoyl group, $C_{6-10}$ aryl-carbonyl group and heterocyclic carbonyl group, except the groups described below, the same definition as described before are also applicable.

The substituent $S^3$ described above is also applicable as the substituent of $C_{6-10}$ aryl group in a $C_{6-10}$ aryl* group, phenyl* group, a $C_{6-10}$ aryl*oxy group, phenoxy*, a $C_{6-10}$ aryl*thio group, a $C_{6-10}$ aryl*amino group, a $C_{6-10}$ aryl*sulfonyl group and a $C_{6-10}$ aryl*sulfonyloxy group.

The substituent $S^3$ described above is also applicable as the substituent of the aromatic ring in $C_{7-12}$ or $C_{7-19}$ aralkyl group in the $C_{7-12}$ aralkyl* group, benzyl* group, $C_{7-19}$ aralkyl*oxy group, benzyl*oxy group, $C_{7-19}$ aralkyl* sulfonyl group and $C_{7-19}$ aralkyl*sulfonyloxy group.

The substituent $S^3$ described above is also applicable as the substituent of the heterocyclic group in the heterocyclic* group, heterocyclic*oxy group, heterocyclic*thio group, heterocyclic*amino group, heterocyclic*acetyl group and heterocyclic*carboxyamido group.

The substituent $S^3$ described above is also applicable as the substituent of the nitrogen-containing heterocyclic ring in a quaternary ammonium* group.

The substituent $S^1$ described above is also applicable as the substituent of the $C_{1-6}$ group in the $C_{1-6}$ alkyl* group which may be substituted represented by $C_{1-6}$-alkyl* group.

The substituent $S^3$ described above is also applicable as the substituent of "the $C_{3-10}$ cycloalkyl group which may be substituted" and "the $C_{5-6}$ cycloalkenyl group which may be substituted" represented respectively by $C_{3-10}$ cycloalkyl group* and by $C_{5-6}$ cycloalkenyl* group.

The substituents of the $C_{1-6}$ alkylthio group in "$C_{1-6}$ alkylthio group which may be substituted" represented by $C_{1-6}$ alkylthio* group (hereinafter represented by "substituent $S^4$") include hydroxyl, a $C_{1-6}$ alkoxy group, a $C_{3-10}$ cycloalkyloxy group, a $C_{6-10}$ aryloxy group, a $C_{7-19}$ aralkyloxy group, mercapto, a $C_{1-6}$ alkylthio group, a $C_{3-10}$ cycloalkylthio group, a $C_{6-10}$ arylthio group, a $C_{7-19}$ aralkylthio group, amino, a mono-$C_{1-6}$ alkylamino group, a di-$C_{1-6}$ alkylamino group, a cyclic amino group, halogen, cyano, carboxyl, carbamoyl, an acyl+oxy group, sulfo, and a quaternary ammonium group.

The substituents of the $C_{2-6}$ alkenylthio group (hereinafter represented by "substituent $S^5$) in $C_{2-6}$ alkenylthio group which may be substituted" represented by a $C_{2-6}$ alkenylthio group include halogen, cyano, carboxyl, carbamoyl, a mono-$C_{1-6}$ alkylcarbamoyl group, a di-$C_{1-6}$ alkylcarbamoyl group and thiocarbamoyl.

The "acyl+ group" is the above mentioned $C_{1-6}$ alkanoyl group, $C_{6-10}$ aryl* carbonyl group, $C_{7-19}$ aralkyl carbonyl group, heterocyclic carbonyl group or heterocyclic* acetyl group. Representative examples of the acyl+ group include formyl, acetyl, propionyl, n-butyryl, isobutyryl, valeryl, pivaloyl, n-hexanoyl, chloroacetyl, dichloroacetyl, trichloroacetyl, 3-oxobutyryl, 4-chloro-3-oxobutyryl, 3-carboxypropionyl, 4-carboxybutyryl, 3-ethoxycarbamoylpropionyl, benzoyl, naphthoyl, p-methylbenzoyl, p-hydroxybenzoyl, p-methoxybenzoyl, p-chlorobenzoyl, p-nitrobezoyl, o-carboxybenzoyl, o-(ethoxycarbonylcarbamoyl)benzoyl, o-(ethoxycarbonylsulfamoyl)benzoyl, phenylacetyl, p-methylphenylacetyl, p-hydroxyphenylacetyl, p-methoxyphenylacetyl, 2,2-diphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl and (5-amino-1,2,4-thiadiazol-3-yl)acetyl.

The acyl+ group in "acyl+ oxy group" and "acyl+ amino group" means the acyl+ group described above, and examples of the "acyl+ oxy group" include formyloxy, acetoxy, propionyloxy, butyryloxy, valeryloxy, pivaloyloxy, chloroacetoxy, dichloroacetoxy, trichloracetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl) benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy and furylacetyloxy. Examples of the "acyl+ amino group" include acetamido (CH$_3$CONH—), benzamido(C$_6$H$_5$CONH—), phenylacetamido (C$_6$H$_5$CH$_2$CONH—) and 2-thienylacetamido

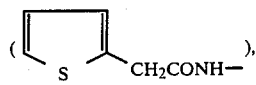

The acyl+ amino and alkylthio groups in "acyl+ aminoalkylthio group" mean the acyl+ amino group and the C$_{1-6}$ alkylthio group described above, respectively and examples of the "acyl+ amino C$_{1-6}$ alkylthio group" include acetamidomethylthio and 2-acetamidoethylthio.

"Arylacyl+ group" is desirably "C$_{6-10}$ aryl-acyl+ group", such as benzoyl, phthaloyl, naphthoyl or phenylacetyl group.

"Arylacyl+oxy group" is desirably "C$_{6-10}$ aryl-acyl+ oxy group", such as benzoyloxy, naphthoyloxy or phenylacetyloxy.

The substituent of the ureido group in the "ureido group which may be substituted" represented by "ureido* group" includes a C$_{1-6}$ alkyl group, a C$_{6-10}$ aryl* group, a C$_{7-19}$ aralkyl* group, an acyl+ group, carbamoyl, sulfo (which may form a salt with sodium or potassium), sulfamoyl and amidino.

The substituent of the sulfamoyl group in "sulfamoyl group which may be substituted" represented by "sulfamoyl* group" includes a C$_{1-6}$ alkyl group and amidino.

The substituent of the "carbamoyl group which may be substituted" represented by the "carbamoyl*group" and "carbamoy*oxy" includes a C$_{1-6}$ alkyl group, a C$_{6-10}$ aryl*group, a C$_{7-12}$ aralkyl*group and an acyl+ group, including the case where the carbamoyl nitrogen atom is the ring constituting nitrogen atom of the nitrogen-containing heterocyclic ring.

The substituent of the "thiocarbamoyl group which may be substituted" represented by "thiocarbamoyl*group" includes a C$_{1-6}$ alkyl, C$_{6-10}$ aryl*, C$_{7-12}$ aralkyl* and acyl+ groups, including the case where the thiocarbamoyl-nitrogen atom is the ring constituting nitrogen atom of the nitrogen-containing heterocyclic ring.

The substituent of the cyclic amino group in the "cyclic amino group which may be substituted" represented by "cyclic amino*group" (hereinafter, represented by "substituent S$^6$") includes a C$_{1-6}$ alkyl group, a C$_{2-6}$ alkenyl group, a C$_{3-10}$ cycloalkyl group, a C$_{6-10}$ aryl*group, a C$_{7-12}$ aralkyl*group, a di-C$_{6-10}$ aryl-methyl group, a tri-C$_{6-10}$ aryl-methyl group, hydroxy, a C$_{1-6}$ alkoxy group, a C$_{6-10}$ aryl*oxy group, a C$_{7-19}$ aralkyl*oxy group, mercapto, a C$_{1-6}$ alkylthio group, a C$_{6-10}$ aryl*thio group, a C$_{7-19}$ aralkyl*thio group, amino, a mono-C$_{1-6}$ alkylamino group, a di-C$_{1-6}$ alkylamino group, a C$_{6-10}$ aryl*amino group, a C$_{7-19}$ aralkyl*amino group, halogen, nitro, azido, oxo, thioxo, cyano, carboxyl, an acyl+ group, a substituted oxycarbonyl group, an acyl+ oxy group, an acyl+ amino group, carbamoyl, carbamoyloxy, thiocarbamoyl and sulfo.

The formyl group substituted with the heterocyclic* carbonyl group described above as a C$_{1-6}$ alkanoyl*-group is an acyl group having the formula of heterocyclic* ring —CO—CO— wherein the heterocyclic* group described above is also applicable here, oxazolyl group, thiazolyl group, oxadiazolyl group and thiadiazolyl group, all of which may be substituted being more desirable. Examples of the "heterocyclic*-CO-CO- group" include 2-(2-, 4- or 5-oxazolyl)-2-oxoacetyl, 2-(2-, 4- or 5-thiazolyl)-2-oxoacetyl, 2-(2-amino-4-thiazolyl)-2-oxoacetyl, 2- (1,2,4-oxadiazol-3- or 5-yl)-2-oxoacetyl, 2-(1,2,4-thiadiazol-3- or 5-yl)-2-oxoacetyl and 2-(5-amino-1,2,4-thiadiazol-3-yl)-2-oxoacetyl.

A C$_{2-6}$ alkanoyl*group is most desirably a substituted acetyl group. The number of the substituents in the substituted acetyl group is one to three, and the substituent S$_1$ described above is also applicable as the substituent of the C$_{1-6}$ alkanoyl group. When 2 or 3 substituents are present, these substituents may be the same of different, and two of them may combine to form a double bond. The mono-substituted acetyl group and di-substituted acetyl group are represented respectively by R$^{15}$CH$_2$CO—, and by

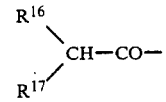

The tri-substituted acetyl group is desirably those where two of the substituents are combined to form a C=C bond or a C=N bond, which are represented respectively by

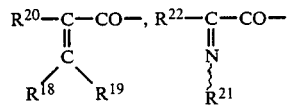

The symbols R$^{15}$, R$^{16}$, R$^{17}$, R$^{20}$ and R$^{22}$ mean the substituent (S$^1$) described above. The symbols R$^{18}$, R$^{19}$ and R$^{21}$ are described below. In the follwoing, acetyl groups having these substituents (R$^{15}$, R$^{16}$, R$^{17}$, R$^{18}$, R$^{19}$, R$^{20}$, R$^{21}$ and R$^{22}$) are described in detail.

(i) R$^{15}$CH$_2$CO—

The symbol R$^{15}$ means the substituent (S$^1$) of the C$_{1-6}$ alkyl group described above, among which a C$_{5-6}$ cycloalkenyl, a C$_{6-10}$ aryl*group, a C$_{6-10}$ aryl*oxy group, a C$_{1-6}$ alkyl*thio group, a C$_{2-6}$ alkenyl*thio group, a C$_{6-10}$ aryl*thio group, amino, a cyclic amino group, cyano, an acyl+ group, an acyl+ oxy group, a heterocyclic*-group, a heterocyclic*thio group, and a quaternary ammonium*group is frequently used. Examples of the "acyl group represented R$^{15}$CH$_2$CO—" include 1,4-cyclohexadienylacetyl, phenylacetyl, p-tolylacetyl, p- hydroxyphenylacetyl, p-methoxyphenylacetyl, p-chlorophenylacetyl, o-aminomethylphenylacetyl, phenoxyacetyl, p-hydroxypheoxyacetyl, p-chlorophenoxyacetyl, cyanomethylthioacetyl, difluoromethylthioacetyl, trifluoromethiolthioacetyl, (2-carboxyethyl)thioacetyl, (2-amino-2-carboxyethyl) thioacetyl, (2-chlorovinyl)thioacetyl, (2-carboxyvinyl)thioacetyl, (2-fluoro-2-carbamoylvinyl)thioacetyl, (1,2-dichlorovinyl)thioacetyl, (2-chloro-2-carboxyvinyl)thioacetyl, phenylthioacetyl, p-hydroxyphenylthioacetyl, phenylthioacetyl, p-hydroxyphenylthioacetyl, phenylglycyl, 1H-tetrazol-1-ylacetyl, 3,5-dichloro-4-oxo-1,4-dihydopyridin-1-ylacetyl, cyanoacetyl, acetoacetyl, benzoylacetyl, furylcarbonylacetyl, thienylcarbonylacetyl, 1H-tetrazol-5-yl acetyl, 1-methyl-1H-tetrazol-5-ylacetyl, (2-furyl)acetyl, (2-thienyl)acetyl, (3-thienyl)acetyl, (4-oxoazolyl)acetyl, (4-thiazolyl)acetyl, (2-amino-4-thiazolyl)acetyl, (1,2,4-thiadiazol-3-yl)acetyl, (5-amino-1,2,4-thiadiazol-3-yl)acetyl, (2-pyridyl)acetyl, (4-pyridyl)acetyl, 2-imidazolyl)thioacetyl, (2-pyridyl)thioacetyl, (4-pyridyl)thioacetyl, (2-thienyl)thioacetyl, hydroxypyridylthioacetyl, (5-isothiazolyl)thioacetyl, 3-methylthio-5-isothiazolyl)thioacetyl, (4-cyano-5-isothiazolyl)thioacetyl, (4-cyano-2-methyl-3-oxo-2,3-dihydroisothiazol-5-yl)thioacetyl, pyridiniumacetyl and quinoliniumacetyl.

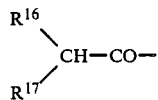

(ii)

The symbol $R^{16}$ means the substituent ($S^1$), among which a $C_{5-6}$ cycloalkenyl group, a $C_{6-10}$ aryl* group, a $C_{6-10}$ aryl*oxy group, a $C_{1-6}$ alkyl*thio group, a $C_{2-6}$ alkenyl*thio group, a $C_{6-10}$ aryl*thio group, a cyclic amino group, cyano, a heterocyclic* group, a heterocyclic*thio group, a heterocyclic*carboxamide group or a quaternary ammonium* group is also here frequently used. The symbol $R^{17}$ means also the substituent ($S^1$) described above, among which hydroxyl, mercapto, amino, an amino group substituted with an amino acid residue, hydrazino, azido, ureido*, an acyl+ oxy group, an acyl+-amino group, carboxyl, a substituted oxycarbonyl group, sulfo, sulfamoyl, carbamoyl and a heterocyclic* carboxamido group are preferable. Among these, the groups having an amino group as the substituent $R^{17}$ (i.e.,

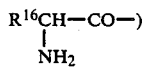

are sometimes especially classified as "amino acid residues". The acyl group represented by the formula

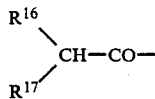

include 2-amino-2-(1,4-cyclohexadienyl)acetyl, mandelyl, α-azidophenylacotyl, α-carboxyphenylacetyl, α-(phenoxycarbonyl)phenylacetyl, α-(o-hydroxyphenyl)oxycarbonylphenylacetyl, α-(p-tolyloxycarbonyl)phenylacetyl, α-sulfophenylacetyl, α-sulfo-p-hydroxyphenylacetyl, α-ureidophenylacetyl, α-(Nγ-sulfoureido)phenylacetyl, α-carboxy-p-hydroxyphenylacetyl, α-(formyloxy)phenylacetyl, α-(2-amino-3-carboxypropionamido)phenylacetyl, α-(3-amino-3-carboxypropionamido)phenylacetyl, α-(3,4-dihydroxybenzamido)phenylacetyl, α-(5-carboxy-4-imidazolylcarboxamido)phenylacetyl, α-(1,3-dimethyl-4-pyrazolylcarboxamido)phenylacetyl, 5-phenyl-3-isoxazolylcarboxamido)phenylacetyl, α-[1-(p-methoxyphenyl)-4-chloro-1,2,3-triazol-5-ylcarboxamido]phenylacetyl, α-(4-oxo-1,4-dihydropyridin-3-ylcarboxamido) phenylacetyl, α-[2-oxo-5-(3,4-dihydroxyphenyl)-1,2-dihydropyridin-3-ylcarboxamido]phenylacetyl, α-(4-oxo-4H-1-thiopyran-3-ylcarboxamido)phenylacetyl, α-(4-hydroxy-1,5-naphthylidin-3-ylcarboxamido)phenylacetyl, α-(4-ethyl-2,3-dioxopiperazinocarboxamido)phenylacetyl, α-(4-ethyl-2,3-dioxopiperazinocarboxamido)-p-hydroxyphenylacetyl, α-(4-ethyl-2,3-dioxopieradinocarboxamido)-p-benzyloxyphenylacetyl, α-(4-ethyl-2,3-dioxopiperazinocarboxamido)-p-sulfophenylacetyl, α-(4-ethyl-2,3-dioxopiperazinocarboxamido)-p-methoxyphenylacetyl, α-(2-oxoimidazolidinocarboxamido)phenylacetyl, α-(2-oxo-3-methanesulfonylimidazolidinocarboxamido)phenylacetyl, α-(6,7-dihydroxy-4-oxo-4H-benzopyran-3-ylcarboxamido)phenylacetyl, α-(6,7-dihydroxy-2-oxo-2H-benzopyran-3-ylcarboxamido)phenylacetyl, α-hydroxy-2-thienylacetyl, α-hydroxy-3-thienylacetyl, α-carboxy-3-thienylacetyl, α-amino-α-(2-aminothiazol-4-yl) acetyl, α-formamido-α-(2-aminothiazol-4-yl)acetyl, α-acetamido-α-(2-aminothiazol-4-yl)acetyl, α-formamido-α-(2-amino-5-chlorothiazol-4-yl)acetyl, α-acetamido-α-(2-amino-5-chlorothiazol-4-yl)acetyl, α-formamido-α-(5-amino-1,2,4-thiadiazol-3-yl)acetyl, α-acetamido-α-(5-amino-1,2,4-thiadiazol-3-yl)acetyl, α-hydrazino-α-(2-aminothiazol-4-yl)acetyl, α-hydroxy-α-(2-aminothiazol-4-yl)acetyl, α-ureido-α-(2-aminothiazol-4-yl) acetyl, α-[Nγ-(m-hydroxyphenyl)ureido]phenylacetyl, α-[Nγ-(2-methyl-6-hydroxypyrimidin-5-yl)ureido]phenylacetyl, α-[Nγ-(3,4-diacetoxybenzoyl)ureido]phenylacetyl, α-[Nγ-(3,4-dihydroxycinnamoyl)ureido]phenylacetyl, α-[Nγ-(3,4-diacetoxybenzamidoacetyl)ureido]phenylacetyl, α-[Nγ-(2-furylcarbonyl)ureido phenylacetyl, α-[Nγ-(6,7-dihydro-4-oxo-4H-benzopyran-3-ylcarbonyl)ureido]phenylacetyl, α-(2-chlorovinylthio)phenylacetyl, α-carbamoyl-α-(2-chlorovinylthio)acetyl, α-(4-ethyl-2,3-dioxopiperazinocarboxamido)-α-(2-chlorovinylthio)acetyl, α,α-bis-(4-ethyl-2,3-dioxo-1-piperazinocarboxamido)acetyl, α-(2-amino-4-thiazolyl)-α-(4-ethyl-2,3-dioxo-1-piperazinocarboxamido)acetyl, α-(4-hydroxy-6-methylnicotinamido)-α-phenylacetyl, α-(4-hydroxy-6-methylnicotinamido)-α-(4-hydroxypehnyl)acetyl, α-(5,8-dihydro-2-(4-formyl-1-piperazinyl)-5-oxopyrido[2,3-d]pyrimidin-6-carboxamido]-α-phenylacetyl, α-(3,5-dioxo-1,2,4-triazin-6-carboxamido)-α-(4-hydroxyphenyl) acetyl, α-(3-furfurydenamino-2-oxoimidazolidin-1-carboxamido)-α-phenylacetyl, α-(coumarin-3-carboxyamido)-α-phenylacetyl, α-(4-hydroxy-7-methyl-1,8-naphthylidin-3-carboxamido)-α-phenylacetyl, α-(4-hydroxy-7-trifluoromethylquinoline-3-carboxamido)-α-phenylacetyl, N-[2-(2-amino-4-thiazolyl)acetyl]-D-phenylglycyl, α-(6-bromo-1-ethyl-1,4-dihydro-4-oxo-thieno[2,3-b]pyridin-3-carboxamido)-α-phenylacetyl, α-(4-ethyl-2,3-dioxo-1-piperazinocarboxamido)-α-thienylacetyl, α-(4-n-pentyl-2,3-dioxo-1-piperazinocarboxamido)-α-thienylacetyl, α-(4-n-octyl-2,3-dioxo-1-piperazinocarboxamido)-α-thienylacetyl, α-(cyclohexyl-2,3-dioxo-1-piperazinocarboxamido)-α-thienylacetyl, α-[4-(2-phenylethyl)-2,3-dioxo-1-piperazinocarboxamido]-α-thienylacetyl, and α-(3-furfurydeneamino-2-oxoimidazolidine-1-carboxamido)-α-(4-hydroxyphenyl-)acetyl. Examples of the amino acid residue

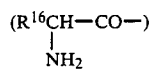

include alanyl, valyl, leucyl, isoleucyl, seryl, threonyl, cysteinyl, cystyl, methionyl, asparagyl, glutamyl, lysyl, arginyl, phenylglycyl, phenylalanyl, thyrosyl, histidyl, tryptophyl and prolyl residue. The amino group in these amino acid residues may be protected by the amino-protectic group described below. Examples of the "amino acid residue wherein the amino group is protected" include N-benzyloxycarbonylalanyl and N-benzyloxycarboxamidophenylglycyl. The amino group in the amino acid residue may be substituted by another amino acid residue. Such an acyl group is a "dipeptide residue", and examples of the acyl group include phenylglycyl-alanyl, benzyl Nα-benzyl-oxycarbonyl-γ-glutamylalanyl, alanyl-phenylglycyl, γ-aspartyl-phenylglycyl and γ-glutamyl-alanyl. The amino group in the amino acid residue may be substituted by a cyclic carbamoyl group. Such an acyl group is for example, N-(4-ethyl-2,3-dioxo-1-piperazinocarbonyl) alanyl, N-(4-ethyl-2,3-dithioxo-1-piperazinocarbonyl)phenylglycyl and N-(4-ethyl-2,3-dioxo-1-piperazinocarbonyl)-threonyl.

As one of the acyl groups represented by the formed

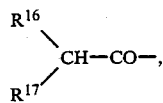

there may use an acyl group represented by the formula

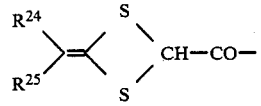

wherein $R^{24}$ and $R^{25}$ are, the same or different, hydrogen, halogen(fluorine, chlorine, bromine, iodine), hydroxymethyl, difluoromethyl, trifluoromethyl, formyl, cyano, azido, carboxyl, carbamoyl, a $C_{1-6}$ alkylthio group or a $C_{6-10}$ aryl*thio group.

Examples of such an acyl group include of a group of the formula

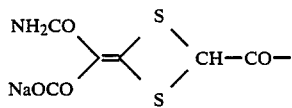

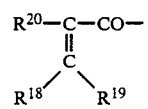

The symbol $R^{20}$ means the substituent ($s^1$) described above, among which a $C_{6-10}$ aryl* group, a $C_{6-10}$ aryl**oxy group, a $C_{6-10}$ aryl*thio group, a heterocyclic* group or a heterocyclic*thio group is frequently used. The symbol $R^{18}$ means hydrogen or a halogen (fluorine, chlorine, bromine or iodine), preferably chlorine. The symbol $R^{19}$ means a $C_{1-6}$ alkyl group, a $C_{6-10}$ aryl* group, a $C_{1-6}$ alkylthio group, halogen, cyano, amino, a $C_{1-6}$ alkylsulfonyl group, a $C_{6-10}$ aryl*sulfonyl group, carbamoyl, a $C_{1-6}$ alkoxyimidoyl group or a heterocyclic* group. The $C_{1-6}$ alkoxy group in the $C_{1-6}$ alkoxyimidoyl group is preferably the $C_{1-6}$ alkoxy group described above, and examples of the $C_{1-6}$ alkoxyimidoyl group include methoxyimidoyl

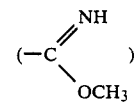

and ethoxyimidoyl. As for the other groups which are not mentioned here, the groups described before are also applicable. Therefore examples of the acyl group of the formula

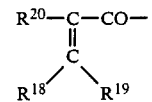

include 2-(2-amino-4-thizolyl)-3-chloroacryloyl, 2-(2-amino-4-thiazolyl) crotonoyl, 2-(2-amino-4-thiazolyl)-cinnamoyl, 2-(2-amino-4-thia-zolyl)-3-methanesulfonylacryloyl, 2-(2-amino-4-thiazolyl)-3-benzenesulfonylacryloyl, 2-(5-amino-1,2,4-thiadiazol-3-yl)-2-pentenoyl, 2-(5-amino-1,2,4-thiadiazol-3-yl)-3-chloroacryloyl,2-(5-amino-1,2,4-thiadiazol-3-yl)crotonoyl,2-(2-amino-5-chloro-4-thiazolyl)-3-chloroacryloyl and 2-(2-amino-5-chloro-4-thiazolyl)crotonoyl.

The symbol $R^{22}$ means the substituent ($s^1$) described above, among which a $C_{3-10}$ cycloalkyl* group, a $C_{5-6}$cycloalkenyl* group, a $C_{6-10}$aryl* group, a $C_{1-6}$ alkoxy group, a $C_{6-10}$aryl* oxy group, a $C_{1-6}$alkyl*thio group, an amino$C_{1-6}$alkylthio group, a $C_{6-10}$ aryl*thio group, a $C_{7-19}$aralkyl*thio group, cyano, an acyl+ group, carbamoyl or a heterocyclic* group is frequently used. Among these, a $C_{6-10}$aryl* group and a heterocyclic* group are especially preferable. The substituents for these $C_{6-10}$aryl and heterocyclic groups are preferably a $C_{1-6}$ alkyl group, hydroxyl, amino or halogen (fluorine, chlorine, bromine or iodine). Preferred examples of the substituent $R^{22}$ include phenyl, p-hydroxyphenyl, 2-furyl, 2-thienyl, 4-oxazolyl, 2-amino-4-oxazolyl, 2-amino-5-chloro-4-oxazolyl,4-thiazolyl,2-amino-4-thiazolyl, 2-amino-5-chloro-4-thiazolyl, 2-amino-5-bromo-4-thiazolyl, 2-amino-5-fluoro-4-thiazolyl, 2-amino-4-thiazolyl-3-oxido, 2-imino-3-hydroxythiazolin-4-yl, 3-isoxazolyl, 5-amino-3-isoxazolyl, 3-isothiazolyl, 5-amino-3-isothiazolyl, 1,2,4-oxadiazol-3-yl, 5-amino-1,2,4-oxadiazol-3-yl, 1,2,4-thiadiazol-3-yl, 5-amino-1,2,4-thiadiazol-3-yl, 1,3,4-oxadiazolyl, 2-amino-1,3,4-oxadiazol-5-yl, 1,3,4-thiadiazolyl, 2-amino-1,3,4-thiadiazol-5-yl, 1-($C_{1-6}$alkyl)-5-amino-1,2,4-triazol-3-yl, 4-($C_{1-6}$alkyl)-5-amino-1,2,4-triazol-3-yl, 4-($C_{1-6}$alkyl)-5-amino-1,2,4-triazol-3-yl, 1($C_{1-6}$alkyl)-2-amino-4-imidazolyl, 2-amino-6-pyridyl, 4-amino-2-pyrimidyl, 2-amino-5-pyrimidyl, 3-pyrazolyl and 4-pyrazolyl.

The symbol $R^{21}$ is a group of the formula $OR^{23}$, $R^{23}$ being or a hydrocarbon residue which may be substituted.

The group represented by the formula

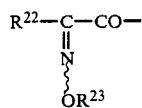

is a syn isomer represented by the formula

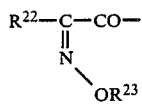

or an anti isomer represented by the formula

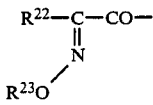

or a mixture thereof, among which a syn isomer having a heterocyclic* group as the substituent $R^{22}$ is preferable. Such an acyl group is represented by the formula

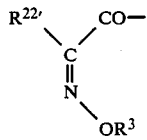

wherein $R^{22'}$ is a heterocyclic* group and $R^3$ is hydrogen or a hydrocarbon residue which may be substituted. Most preferred examples of the heterocyclic* group $R^{22'}$ include a substituted thiazolyl or thiadiazolyl group, i.e. a group of the formula

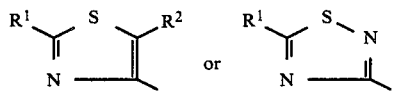

wherein $R^1$ is an amino group which may be protected and $R^2$ is hydrogen, a halogen or nitro. The most desirable $R^b$ group is represented by the formula

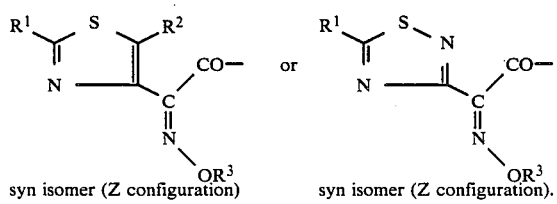

syn isomer (Z configuration)  syn isomer (Z configuration).

That is, among the compounds (I) having an acyl group $R^b$ as the substituent $R^0$ is a compound of the formula:

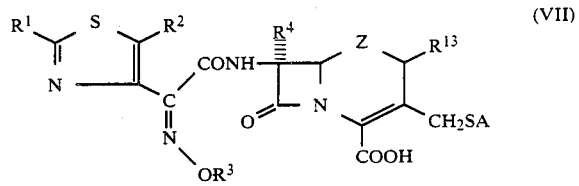

(including a salt or ester thereof)

or

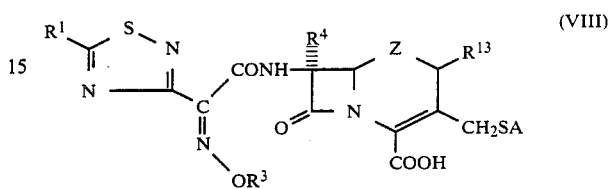

(including a salt or ester thereof)

wherein the symbols are the same meaning as defined above. In the following the substituents $R^1$, $R^2$ and $R^3$ are described in detail.

The symbol $R_1$ is an amino group which may be protected. In the field of β-lactams and peptides, the method of protection of an amino group and the method of deprotection of an amino-protecting group have been investigated extensively and the procedures of amino-protection have already been established. Such prior art methods may be employed for protection of the amino group in this invention. Examples of the amino-protective group include a $C_{1-6}$alkanoyl* group, a $C_{3-5}$alkenoyl* group, a $C_{6-10}$aryl*carbonyl group, phthaloyl, a heterocyclic*carbonyl group, $C_{1-6}$alkyl*sulfonyl group, camphorsulfonyl, a $C_{6-10}$aryl*sulfonyl group, a substituted oxycarbonyl group, carbamoyl*, carbamoyl*oxy, thiocarbamoyl*, a $C_{6-10}$aryl*methyl group, a di-$C_{6-10}$aryl*methyl group, a tri-$C_{6-10}$aryl*methyl group, a $C_{6-10}$aryl*methylene group, a $C_{6-10}$aryl*thio group, a substituted silyl group, and a 2-$C_{1-10}$alkoxy-carbonyl-1-methyl-1-ethenyl group.

Examples of the "$C_{1-6}$alkanoyl* group" here include formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, 3-oxobutyryl, 4-chloro-3-oxobutyryl, phenylacetyl, p-chlorophenylacetyl, pheoxyacetyl and p-chlorophenoxyacetyl.

Examples of the "$C_{3-5}$alkenoyl* group" here include acryloyl, crotonoyl, maleoyl, cinnamoyl, p-chlorocinnamoyl and β-phenylcinnamoyl.

Examples of the "$C_{6-10}$aryl*carbonyl group" here include benzoyl, naphthoyl, p-toluoyl, p-tert-butylbenzoyl, p-hydroxybenzoyl, p-methoxybenzoyl, p-tert-butoxybenzoyl, p-chlorobenzoyl and p-nitrobenzoyl.

Examples of the heterocyclic*carbonyl group include each of the groups described below.

Examples of the "$C_{1-6}$alkyl*sulfonyl group" include methanesulfonyl and ethanesulfonyl.

Examples of the "$C_{6-10}$aryl*sulfonyl group" here include benzenesulfonyl, naphthalenesulfonyl, p-toluenesulfonyl, p-tert-butylbenzenesulfonyl, p-methoxybenzenesulfonyl, p-chlorobenzenesulfonyl and p-nitrobenzenesulfonyl.

Examples of the "substituted oxycarbonyl group" include, in addition to the substituted oxycarbonyl group described above, i.e. a $C_{1-10}$alkoxy-carbonyl group, a($C_{6-10}$aryloxycarbonyl group or a $C_{7-19}$aralkyloxy-carbonyl group, and also the one having substituents, such as methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethyl-silylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl.

Examples of the "carbamoyl* group" here include carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl and N-(p-methoxyphenyl)carbamoyl.

Examples of the "carbamoyl*oxy group" here include carbamoyloxy, N-methylcarbamoyloxy, N,N-dimethylcarbamoyloxy, N-ethylcarbamoyloxy and N-phenylcarbamoyloxy.

Examples of the "thiocarbamoyl* group" here include thiocarbamoyl, N-methylthiocarbamoyl and N-phenylthiocarbamoyl.

Examples of the "$C_{6-10}$aryl*methyl group" include benzyl, naphthylmethyl, p-methylbenzyl, p-methoxybenzyl, p-chlorobenzyl and p-nitrobenzyl.

Examples of the "di-$C_{6-10}$aryl*methyl group" include benzhydryl and di-(p-tolyl)methyl.

Examples of the "tri-$C_{6-10}$aryl*methyl group" include a trityl and tri(p-tolyl)methyl.

Examples of the "$C_{6-10}$aryl*methylene group" include benzylidene, p-methylbenzylidene and p-chlorobenzylidene.

An example of the "$C_{6-10}$aryl*thio group" is o-nitrophenylthio.

"The amino group protected by a "substituted silyl group" is shown by the general formula:

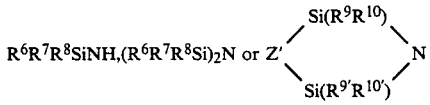

wherein $R^6$, $R^7$, $R^8$, $R^9$, $R^{10}$, $R^{9'}$, and $R^{10'}$ are a $C_{1-6}$alkyl group or $C_{1-6}$aryl* group, and these groups may be the same or different from each other, and $Z'$ is a $C_{1-3}$alkylene gruop such as a methylene, ethylene or propylene. Examples of the substituted silyl group include trimethylsilyl, tert-butyldimethylsilyl and —Si(CH$_3$)$_2$CH$_2$CH$_2$Si(CH$_3$)$_2$—groups.

The $C_{1-10}$alkoxy-carbonyl group in the 2-$C_{1-10}$alkoxycarbonyl-1-methyl-1-ethenyl group is preferably the one described before, and examples of the 2-$C_{1-10}$alkoxy-carbonyl-1-methyl-1-ethenyl group include 2-methoxycarbonyl-1-methyl-1-ethenyl, 2-ethoxycarbonyl-1-methyl-1-ethenyl, 2-tertbutoxycarbonyl-1-methyl-1-ethenyl, 2-cyclohexyloxycarbonyl-1-methyl-1-ethenyl and 2-norbornyloxycarbonyl-1-methyl-1-ethenyl.

The symbol $R^2$ is hydrogen, a halogen or nitro. Examples of the halogen include fluorine, chlorine and bromine, preferably chlorine.

The symbol $R^3$ is hydrogen or a hydrocarbon residue which may be substituted. Examples of the hydrocarbon residue include a $C_{1-6}$alkyl group, a $C_{2-6}$alkenyl group, a $C_{2-6}$ alkynyl group, a $C_{3-10}$cycloalkyl group and a $C_{5-6}$cycloalkenyl group, among which a $C_{1-3}$alkyl group, a $C_{2-3}$alkyl group or a substituted $C_{1-3}$alkyl group is preferable, and a $C_{1-3}$alkyl group or a substituted $C_{1-3}$alkyl group is more preferable. Such a $C_{1-6}$alkyl group is also here preferably the $C_{1-6}$alkyl group described above, such as methyl, ethyl, n-propyl, isopropyl, n-butyl, isobutyl, sec-butyl, tert-butyl, n-pentyl or n-hexyl, among which a $C_{1-3}$alkyl group such as methyl, ethyl or n-propyl is more preferable. The $C_{2-6}$alkenyl group is also here preferably the $C_{2-6}$alkenyl group described above, such as vinyl, allyl, isopropenyl, emthallyl, 1,1-dimethylallyl, 2-butenyl or 3-butenyl. Specific examples of the $C_{2-6}$alkynyl group include ethynyl, 1-propynyl, 2-propynyl, propargyl and 3-butynyl. Among them, a $C_{2-3}$alkynyl group, such as ethynyl, 1-propynyl, 2-propynyl or propargyl is preferable. The $C_{3-10}$cycloalkyl group is also here preferably the $C_{3-8}$cycloalkyl group, such as cyclopropyl, cyclobutyl, cyclopentyl, cyclohexyl, cycloheptyl or adamantyl. Specific examples of the $C_{5-6}$cycloalkenyl group include 2-cyclopentenyl, 3-cyclopentenyl, 2-cyclohexenyl, 3-cyclohexenyl, cyclopentadienyl and cyclohexadienyl.

Examples of the substituent of these hydrocarbon residues include hydroxyl, a $C_{1-6}$alkyl group, a $C_{2-6}$alkenyl group, a $C_{2-6}$alkynyl group, a $C_{3-10}$cycloalkyl group, a $C_{5-6}$cycloalkenyl group, a $C_{6-10}$aryl group, a $C_{7-19}$aralkyl group, a heterocyclic group, a $C_{1-6}$alkoxy group, a $C_{3-10}$cycloalkyloxy group, a $C_{6-10}$aryloxy group, a $C_{7-19}$aralkyloxy group, a heterocyclic oxy group, mercapto, a $C_{1-6}$alkylthio group, a $C_{3-10}$cycloalkylthio group, a $C_{6-10}$arylthio group, a $C_{7-19}$aralkylthio group, a heterocyclic thio group, amino, a mono-$C_{1-6}$alkylamino, a di-$C_{1-6}$alkylamino group, a tri-$C_{1-6}$alkylammonium group, a $C_{3-10}$cycloalkylamino group, a $C_{6-10}$arylamino group, a $C_{7-19}$aralkylamino group, a heterocyclic amino group, a cyclic amino group, azido, nitro, halogen, cyano, carboxyl, a $C_{1-10}$alkoxycarbonyl, a $C_{6-10}$aryloxy-carbonyl group, a $C_{7-19}$aralkyloxycarbonyl, a $C_{6-10}$aryl-acyl+ group, a $C_{1-6}$alkanoyl group, a $C_{3-5}$alkenoyl group, a $C_{6-10}$aryl-acyl+oxy group, a $C_{2-6}$alkanoyloxy group, a $C_{3-5}$alkenoyloxy group, carbamoyl*, thiocarbamoyl*, carbamoyl*oxy, phthalimido, a $C_{1-6}$alkanoylamino group, a $C_{6-10}$aryl-acyl+amino group, carboxyamino, a $C_{1-10}$alkoxy-carboxamido group, a $C_{6-10}$aryloxy-carboxamido group and a $C_{7-19}$aralkyloxy-carboxamido group, preferably hydroxy, a $C_{1-6}$alkoxy group and di-$C_{1-6}$alkylamino group. One to three of these substituents which may be the same or different may be present in each hydrocarbon residue described above. As for the substituent of the hydrocarbon residue, the $C_{1-6}$alkyl group means the one described above, such as methyl, ethyl, n-propyl, isopropyl, n-butyl, isobutyl, sec-butyl, tert-butyl, n-pentyl or nhexyl; the $C_{2-6}$alkenyl group means the one described above, such as vinyl, allyl, isopropenyl, methallyl, 1,1-dimethylallyl, 2-butenyl or 3-butenyl, the $C_{2-6}$alkynyl group means the one described above, such as ethynyl, 1-propynyl, 2-propynyl or propargyl, the $C_{3-10}$cycloalkyl group means the one described above, such as cyclopropyl, cyclobutyl, cyclopentyl, cyclohexyl, cycloheptyl or adamantyl, the $C_{5-6}$cycloalkenyl group means the one described above, such as cyclopropenyl, 2-cyclopentenyl, 3-cyclopentenyl, 2-cyclohexenyl, 3-cyclohexenyl, cyclopentadienyl or cyclohexadienyl, the $C_{6-10}$aryl group means the one described above, such as phenyl, naphthyl or biphenyl group, the $C_{7-19}$aralkyl group means the one described above, such as benzyl, 1-phenylethyl, 2-phenylethyl, phenylpropyl, naphthylmethyl or benzhydryl, the $C_{1-6}$ alkoxy group means the one described above, such as methoxy, ethoxy, n-propoxy, isopropoxy, n-butoxy, tert-butoxy, n-pentyloxy or n-hexyloxy, the $C_{3-10}$cycloalkyloxy group means the one described above, such as cyclopropyloxy or cyclohexyloxy group, the $C_{6-10}$aryloxy group means the one described above, such as phenoxy or naphthyloxy, the $C_{7-19}$aralkyloxy group means the one described above, such as benzyloxy, 1-phenylethyloxy, 2-phenylethyloxy or benzhydryloxy, the $C_{1-6}$alkylthio group means the one described above, such as methylthio, ethylthio, n-propylthio or n-butylthio, the $C_{3-10}$cycloalkylthio group means the one described above, such as cyclopropylthio cyclohexylthio, the $C_{6-10}$arylthio group means the one described above, such as phenylthio or naphthylthio, the $C_{7-19}$aralkylthio group means the one described above, such as benzylthio, phenylethylthio or benzhydrylthio, the mono-$C_{1-6}$alkylamino group means the one described above, such as methylamino, ethylamino, n-propylamino or n-butylamino; the di-$C_{1-6}$ alkylamino group means the one described above, such as dimethylamino, diethylamino, methylethylamino, di-(n-propyl)amino or di-(n-butyl)amino, the tri-$C_{1-6}$alkylammonium group means the one described above, such as trimethylammonium or triethylammonium, the $C_{3-10}$cycloalkylamino group means the one described above, such as cyclopropylamino, cyclopentylamino or cyclohexylamino, the $C_{6-10}$arylamino group means the one described above, such as anilino or N-methylanilino, the $C_{7-19}$aralkylamino group means the one described above, such as benzylamino, 1-phenylethylamino, 2-phenylethylamino or benzhydrylamino, the cyclic amino group means the one described above, such as pyrrolidino, piperidino, piperazino, morpholino or 1-pyrrolyl, the halogen means fluorine, chlorine, bromine or iodine, the $C_{1-10}$alkoxycarbonyl group means the one described above, such as methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl, the $C_{6-10}$aryloxy-carbonyl group means the one described above, such as phenoxycarbonyl or naphthyloxycarbonyl, the $C_{7-19}$aralkyloxy-carbonyl group means the one described above, such as benzyloxycarbonyl or benzhydryloxycarbonyl, the $C_{6-10}$aryl-acyl+ group means the one described above, such as benzoyl, naphthoyl, phthaloyl or phenylacetyl group, the $C_{1-6}$alkanoyl group means the one described above, such as a formyl, acetyl, propionyl, butyryl, valeryl, pivaloyl, succinyl or glutaryl, the $C_{3-5}$alkenoyl group means the one described above, such as acryloyl, crotonoyl or maleoyl, the $C_{6-10}$aryl-acyl+oxy group means the one described above, such as benzoyloxy naphthoyloxy or phenylacetoxy, the $C_{2-6}$alkanoyloxy group means the one described above, such as acetoxy, propionyloxy, butyryloxy, valeryloxy or pivaloyloxy, the $C_{3-5}$alkenoyloxy group means the one described above, such as acryloyloxy or crotonoyloxy, the carbamoyl* group means the one described above, such as carbamoyl, N-methylcarbamoyl, N-ethylcarbamoyl, N,N-dimethylcarbamoyl, N-phenylcarbamoyl, N-acetylcarbamoyl, N-benzoylcarbamoyl or N-(p-methoxyphenyl)carbamoyl, and also pyrrolidinocarbonyl, piperidinocarbonyl, piperazinocarbonyl or morpholinocarbonyl is also applicable; the thiocarbamoyl* group means the one described above, such as thiocarbamoyl, N-methylthiocarbamoyl or N-phenylthiocarbonyl; the carbamoyl*oxy group means the one described above, such as carbamoyloxy, N-methylcarbamoyloxy, N,N-dimethylcarbamoyloxy, N-ethylcarbamoyloxy or N-phenylcarbamoyloxy, the $C_{1-6}$alkanoylamino group includes acetamido, propionamido, butyroamido, valeroamido or pivaloamido. Examples of the "$C_{6-10}$aryl-acyl+amino group" include benzamido, naphthoylamido and phthalimido. Examples of the "$C_{1-10}$alkoxy-carboxamido group" include methoxycarboxamido ($CH_3OCONH-$), ethoxycarboxamido and ert-butoxycarboxamido. Examples of the "$C_{6-10}$aryloxy-carboxamido group" include phenoxycarboxamido($C_6H_5OCONH-$), and examples of the "$C_{7-19}$aralkyloxy-carboxamido group" include benzyloxycarboxamido ($C_6H_5CH_2OCONH-$) and benzhydryloxycarboxamido. The heterocyclic group and the heterocyclic group in the heterocyclic oxy, heterocyclic thio or heterocyclic amino group means the group formed by removing one of the hydrogen atoms attached to the carbon atoms of the heterocyclic ring, and examples of the heterocyclic ring include a 5- to 8-membered ring containing one to several, preferably one to four hetero atoms, such as nitrogen (which may be oxidized), oxygen or sulfur atom and a condensed ring thereof. Such heterocyclic groups mean those described above, such as 2-pyrrolyl. Examples of the "heterocyclic oxy group" include thiazolyloxy, and examples of the "heterocyclic thio group" include thiazolylthio. Examples of the "heterocyclic amino group" include thiazolylamino and thiadiazolylamino.

Preferable examples of the substituted hydrocarbon residue include a $C_{1-3}$alkyl group (the $C_{1-3}$alkyl group means methyl, ethyl, n-propyl or isopropyl) which is substituted by one to three groups, such as hydroxyl, a cycloalkyl group, an alkoxy group, an alkylthio group, amino, trialkylammonium group, a halogen, carboxyl, an alkoxycarbonyl group, carbamoyl, cyano, azido or a heterocyclic group and more specifically, cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-(trimethylammonium)ethyl, 2-(triethylammonium)-ethyl, fluoromethyl, difluoromethyl, trifluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, 2-azidoethyl, 2-(pyrazolyl)ethyl, 2-(imidazolyl)ethyl, 2-(2-oxopyrrolidin-3-yl)ethyl, 2-amino-4-thiazolylmethyl, 5-amino-1,2,4-thiadiazol-3-ylmethyl, 1-carboxy-1-(2,3,4-trihydroxyphenyl)methyl, 2-oxo-3-pyrrolidyl, and many others. The most preferred hydrocarbon residues among these described above are a straight-chain $C_{1-}$ 3alkyl group, such as methyl, ethyl or n-propyl and a straight-chain or branched $C_{1-3}$alkyl group substituted by halogen, hydroxyl, an alkoxy group, carboxyl, an alkoxycarbonyl group or cyano, such as 2-fluoroethyl, 2-chloroethyl, 2-methoxyethyl, cyanomethyl, carboxymethyl, tert-butoxycarbonylmethyl, 1-carboxy-1-methylethyl or 1-tert-butoxycarbonyl-1-methylethyl; and allyl and propagyl.

When the symbol $R^{3'}$ represents one of the most preferred hydrocarbon residues described above or hydrogen, the compound (I) of this invention having the acyl group of the formula:

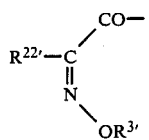

wherein $R^{22'}$ is a heterocyclic* group, as the substituent $R^0$ shows particularly potent antibacterial activity, and exerts excellent bactericidal action especially against resistant bacteria. As described above, the heterocyclic* group $R^{22}$ is most preferably the one having the formula:

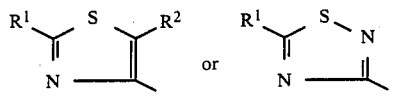

wherein $R^1$ is an amino grup which may be protected, and $R^2$ is hydrogen, a halogen or nitro, preferably hydrogen and therefore the most preferred compound (I) is the one having the formula:

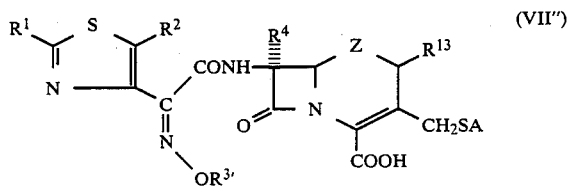

(VII")

or

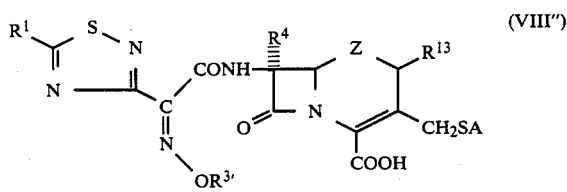

(VIII")

wherein the symbols are the same meaning as defined above (including a salt or ester thereof). Between them, the compound (V") is desirable.

Preferred examples of the acyl group of the formula:

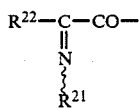

include 2-(2-aminothiazol-4-yl)-2(Z)-(hydroxyimino)acetyl, 2-(2-aminothiazol-4-yl)-2(Z)-(methoxyimino)acetyl, 2-(2-chloroacetamidothiazol-4-yl)-2(Z)-(methoxyimino)acetyl, 2-(2-aminothiazol-4-yl)-2(Z)-(ethoxyimino)acetyl, 2-(2-aminothiazol-4-yl)-2(Z)-(n-propoxyimino)acetyl, 2-(2-aminothiazol-4-yl)-2(Z)-(isopropoxyimino)acetyl, 2-(2-aminothiazol-4-yl)-2(Z)-(n-butoxyimino)acetyl, 2-(2-aminothiazol-4-yl)-2(Z)-(n-hexyloxyimino)acetyl, 2-(2-aminothiazol-4-yl)-2(Z)-(cyclopropylmethyloxyimino)acetyl, 2-(2-aminothiazol-4-yl)-2(Z)-(benzyloxyimino)acetyl, 2-(2-aminothiazol-4-yl)-2(Z)-(allyloxyimino)acetyl, 2-(aminothiazol-4-yl)-2(Z)-(propargyloxyimino)acetyl, 2-(2-aminothiazol-4-yl)-2(Z)-(methoxymethyloxyimino)acetyl, 2-(2-aminothiazol-4-yl)-2(Z)-(ethoxymethyloxyimino)acetyl, 2-(2-aminothiazol-4-yl)-2(Z)-[(1-methoxyethyl) oxyimino]acetyl, 2-(2-aminothiazol-4-yl)-2(Z)-[(2-methoxyethyl) oxyimino]acetyl, 2-(2-aminothiazol-4-yl)-2(Z)-[(2-ethoxyethyl) oxyimino]acetyl, 2-(2-aminothiazol-4-yl)-2(Z)-[(1-ethoxyethyl) oxyimino]acetyl, 2-(2-aminothiazol-4-yl)-2(Z)-[(2-hydroxyethyl) oxyimino]-acetyl, 2-(2-aminothiazol-4-yl)-2(z)-(methylthiomethyloxyimino)acetyl, 2-(2-aminothiazol-4-yl)-2(Z)-[(2-aminoethyl)oxyimino]acetyl, 2-(2-aminothiazol-4-yl)-2(Z)-(fluoromethyloxyimino)acetyl, 2-(2-aminothiazol-4-yl)-2(Z)-(difluoromethyloxyimino)acetyl, 2-(2-aminothiazol-4-yl)-2(Z)-(trifluoromethyloxyimino)acetyl, 2-(2-aminothiazol-4-yl)-2(Z)-[(2-fluoroethyl)oxyimino]acetyl, 2-(2-aminothiazol-4-yl)-2(Z)-[(2,2-difluoroethyl)oxyimino]acetyl, 2-(2-aminothiazol-4-yl)-2(Z)-(chloromethyloxyimino)acetyl, 2-(2-aminothiazol-4-yl)-2(Z)-[2-chloroethyl)oxyimino]acetyl, 2-(2-aminothiazol-4-yl)-2(Z)-[(2,2-dichloroethyl)oxyimino)acetyl, 2-(2-aminothiazol-4-yl)-2(Z)-[(2,2,2-trichloroethyl)oxyimino]acetyl, 2-(2-aminothiazol-4-yl)-2(Z)-[(2-bromoethyl)oxyimino]acetyl, 2-(2-aminothiazol-4-yl)-2(Z)-[(2-iodoethyl)oxyimino]acetyl, 2-(2-aminothiazol-4-yl)-2(Z)-[(2,2,2-trifluoroethyl)oxyimino]acetyl, 2-(2-aminothiazol-4-yl)-2(Z)-(carboxymethyloxyimino)acetyl, 2-(2-aminothiazol-4-yl)-2(Z)-(1-carboxyethloxyimino)acetyl, 2-(2-aminothiazol-4-yl)-2(Z)-[(2-carboxyethyl)oxyimino]acetyl, 2-(2-aminothiazol-4-yl)-2(Z)-(1-carboxypropyloxyimino)acetyl, 2-(2-aminothazol-4-yl)-2(Z)-[(3-carboxypropyl)oxyimino]acetyl, 2-(2-aminothiazol-4-yl)-2(Z)-[(1-carboxybutyl)oxyimino]acetyl, 2-(2-aminothiazol-4-yl)-2(Z)-(cyanomethyloxyimino)acetyl, 2-(2-aminothiazol-4-yl)-2(Z)-[(1-carboxy-1-methylethyl)oxyimino]acetyl, 2-(2-aminothiazol-4-yl)-2(Z)-(methoxycarbonylmethyloxyimino)acetyl, 2-(2-aminothiazol-4-yl)-2(Z)-(ethoxycarbonylmethyloxyimino)acetyl, 2-(2-aminothiazol-4-yl)-2(Z)-[(tert-butoxycarbonylmethyl)oxyimino]acetyl, 2-(2-aminothiazol-4-yl)-[1-(tert-butoxycarbonyl)ethoxyimino]acetyl, 2-(2-aminothiazol-4-yl)-2(Z)-[(1-methoxycarbonyl-1-methylethyl) oxyimino]acetyl, 2-(2-aminothiazol-4-yl)-2(Z)-[(1-ethoxycarbonyl-1-methylethyl)oxyimino]acetyl, 2-(2-aminothiazol-4-yl)-2(Z)-[(1-tert-butoxycarbonyl-1-methylethyl)oxyimino]acetyl, 2-(2-aminothiazol-4-yl)-2(Z)-[1-(tert-butoxycarbonyl) propoxyimino]acetyl, 2-(2-aminothiazol-4-yl)-2(Z)-[(1-benzyloxycarbonyl-1-methylethyl)oxyimino]acetyl, 2-(2-aminothiazol-4-yl)-2(Z)-[(1-pivaloyloxycarbonyl-1-methylethyl)oxyimino]acetyl, 2-(2-aminothiazol-4-yl)-2(Z)-(carbamoylmethyloxyimino) acetyl, 2-(2-aminothiazol-4-yl)-2(Z)-[1-(1-carbamoyl-1-methyl) ethyloxyimino]acetyl, 2-(2-aminothiazol-4-yl)-2(Z)-[(2-azidoethyl)oxyimino]acetyl, 2-(aminothiazol-4-yl)-2(Z)-(phenoxycarbonyloixyimino)acetyl, 2-(2-amino-5-chlorothiazol-4-yl)-2(Z)-(hydroxyimino)acetyl, 2-(2-amino-5-chlorothiazol-4-yl)-2(Z)-(methoxyimino)a- cetyl, 2-(2-amino-5-chlorothiazol-4-yl)-2(Z)-(ethoxyimino)acetyl, 2-(2-amino-5-chlorothiazol-4-yl)-2(z)-(n-propoxyimino)acetyl, 2-(2-amino-5-chlorothiazol-4-yl)-2(Z)-[(2-fluoroethyl)oxyimino]acetyl, 2-(2-amino-5-chlorothiazol-4-yl)-2(Z)-[(2-chloroethyl)oxyimino]acetyl, 2-(2-amino-5-chlorothiazol-4-yl)-2(Z)-(carboxymethyloxyimino)acetyl, 2-(2-amino-5-chlorothiazol-4-yl)-2(Z)-[(tert-butoxycarbonylmethyl)oxyimino]acetyl, 2-(2-amino-5-chlorothiazol-4-yl)-2(Z)-[(1-carboxy-1-methylethyl)oxyimino]acetyl, 2-(2-amino-5-chlorothiazol-4-yl)-2(Z)-[(1-tert-butoxycarbonyl-1-methylethyl) oxyimino]acetyl, 2-(2-amino-5-bromothiazol-4-yl)-2(Z)-(ethoxyimino)acetyl, 2-(2-amino-5-bromothiazol-4-yl)-2(Z)-(ethoxyimino)acetyl, 2-(5-amino-1,2,4-thiadiazol-3-yl)-2(Z)-(hydroxyimino)acetyl, 2-(5-amino-1,2,4-thiadiazol-3-yl)-2(Z)-(methoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-[(2-fluoroethyl)oxyimino]acetyl, 2-(5-amino-1,2,4-thiadiazol-3-yl)-2(Z)-[(2-chloroethyl)oxyimino]acetyl, 2-(5-amino-1,2,4-thiadiazol-3-yl)-2(Z)-(carboxymethyloxyimino)acetyl, 2-(5-amino-1,2,4-thiadiazol-3-yl)-2(Z)-[(1-carboxy-1-methylethyl) oxyimino]acetyl, 2-(5-amino-1,2,4-thiadiazol-3-yl-2(Z)-[(1-tert-butoxycarbonyl-1-methylethyl)oxyimino]acetyl, 2-(5-aminoisoxazol-3-yl)-2(Z)-(ethoxyimino)acetyl, 2-(5-amino-1,2,4-oxadiazol-3-yl)-2(Z)-(ethoxyimino)acetyl, 2-(2-imino-3-hydroxythiazolin-4-yl)-2(Z)-(ethoxyimino)acetyl, 2-(2-amino-3-oxidothiazol-4-yl)-2(Z)-(ethoxyimino)acetyl, 2-thienyl-2(Z)-(methoxyimino)acetyl, 2-thienyl-2(Z)-(ethoxyimino)acetyl, 2-furyl-2(Z)-(methoxyimino)acetyl, 2-furyl-2(Z)-(ethoxyimino)acetyl, 2-(1,3,4-thiadiazolyl)-2(z)-(ethoxyimino)acetvl, 2-(p-hydroxyphenyl)-2(Z)-(ethoxyimino)acetyl, 2-phenyl-2(Z)-(ethoxyimino)acetyl, 2-phenyl-2(Z)-(hydroxyimino)acetyl, 2-[p-(γ-D-glutamyloxy)phenyl]-2(Z)-(hydroxyimino)acetyl, 2[p-(3-amino-3-carboxypropoxy)phenyl]-2(Z)-(hydroxyimino)acetyl, 2-(2-aminothiazol-4-yl)-2(Z)-[(2-aminothiazol-4-yl-methyl)oxyimino]acetyl, 2-(2-aminothiazol-4-yl)-2(Z)-[(5-amino-1,2,4-thiadiazol-5-ylmethyl)oxyimino]acetyl, 2-(2-aminothiazol-4-yl)-2(Z)-[1-carboxy-1-[(2,3,4-trihydroxy)-phenyl]methyloxyimino)acetyl, and 2-(2-aminothiazol-4-yl)-2(Z)-[(2-oxo-3-pyrrolidylmethyl)oxyimino]acetyl.

Examples of the $C_{1-6}$alkanoyl* group described above as an acyl group ($R^b$) include, in addition to the $C_{1-6}$alkanoyl group described above, a heterocycle.*-CO—CO—, $R^{15}CH_2$ a group of the formula:

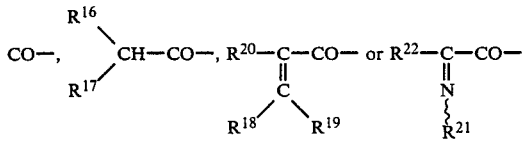

trifluoroacetyl, 4-carboxybutyryl, 5-amino-5-carboxyvaleryl, 5-oxo-5-carboxyvaleryl, N-[2-(2-amino-4-thiazolyl-2-(2)-(methoxyimino)acetyl]-D-alanyl, N-[2-(2-amino-4-thiazolyl-2(Z)-(methoxyimino)acetyl]-D-phenylglycyl and 2-(2-amino-4-thiazolyl)-2-[2-(2-amino-4-thiazolyl)-2(Z)-(methoxyimino)acetamido]acetyl.

As an acyl group ($R^b$), except the $C_{1-6}$alkanoyl* group, there may be mentioned a $C_{3-5}$alkenoyl* group, such as acryloyl, crotonoyl, maleoyl, cinnamoyl, p-chlorocinnamoyl or β-phenylcinnamoyl; a $C_{3-10}$cycloalkyl-carbonyl group, such as cyclopropylcarbonyl, cyclobutylcarbonyl, cyclopentylcarbonyl, cyclohexylcarbonyl, cycloheptylcarbonyl or adamantylcarbonyl as described above; a $C_{5-6}$cycloalkenylcarbonyl group, such as cyclopentenylcarbonyl, cyclopentadienylcarbonyl, cyclohexenylcarbonyl or cyclohexadienylcarbonyl as described above; a $C_{6-10}$aryl*carbonyl group, such as benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl as described above; and "a heterocyclic*carbonyl group", such as 2- or 3-pyrrolylcarbonyl, 3-, 4- or 5-pyrazolylcarbonyl, 2-, 4- or 5-imidazolylcarbonyl, 1,2,3- or 1,2,4-triazolylcarbonyl, 1H- or 2H-tetrazolylcarbonyl, 2- or 3-furylcarbonyl, 2- or 3-thienylcarbonyl, 2-, 4- or 5-oxazolylcarbonyl, 3-, 4- or 5-isoxazolylcarbonyl, 1,2,3-oxadiazol-4- or 5-ylcarbonyl, 1,2,4-oxadiazol-3- or 5-ylcarbonyl, 1,2,5- or 1,3,4-oxadiazolylcarbonyl, 2-, 4- or 5-thiazolylcarbonyl, 2-amino-4-thiazolylcarbonyl, 3-, 4- or 5-isothiazolylcarbonyl, 1,2,3-thiadiazol-4- or 5-ylcarbonyl, 1,2,4-thiadiazol-3- or 5-ylcarbonyl, 5-amino-1,2,4-thiadiazol-3-ylcarbonyl, 1,2,5- or 1,3,4-thiadiazolylcarbonyl, 2- or 3-pyrrolidinylcarbonyl, 2-, 3- or 4-pyridylcarbonyl, 2-, 3- or 4-pyridylcarbonyl-N-oxido, 3- or 4-pyridazinylcarbonyl, 3- or 4-pyridazinylcarbonyl-N-oxido, 2-, 4- or 5-pyrimidinylcarbonyl, 2-, 4- or 5-pyrimidinylcarbonyl-N-oxido, pyrazinylcarbonyl, 2-, 3- or 4-piperidinylcarbonyl, piperazinylcarbonyl, 3H-indol-2- or 3-ylcarbonyl, 2-, 3- or 4-pyranylcarbonyl, 2-, 3- or 4-thiopyranylcarbonyl, benzopyranylcarbonyl, quinolylcarbonyl, pyrido[2,3-d]pyrimidylcarbonyl, 1,5-, 1,6-, 1,7-, 1,8-, 2,6- or 2,7-naphthylidylcarbonyl, thieno[2,3-b]pyridylcarbonyl, pyrimidopyridylcarbonyl, pyrazinoquinolylcarbonyl or 3-(2,6-dichlorophenyl-5-methylisoxazol-4-ylcarbonyl.

The protective group for the amino group as the substituent $R^0$ (hereinafter sometimes represented by the symbol $R^c$) is also here the protective group described above for the amino group which may be protected and is represented by the symbol $R^1$, such as phthaloyl, a $C_{1-6}$alkyl*sulfonyl group, camphorsulfonyl, a $C_{6-10}$aryl*sulfonyl group, a substituted oxycarbonyl group, carbamoyl*, thiocarbamoyl*, a $C_{6-10}$aryl*methyl group, a di-$C_{6-10}$aryl*methyl group, a tri-$C_{6-10}$aryl*methyl group, a $C_{6-10}$aryl*methylene group, a $C_{6-10}$aryl*thio group, a substituted silyl group or a 2-$C_{1-10}$alkoxy-carbonyl-1-methyl-1-ethenyl group, among which phthaloyl group, a substituted oxycarbonyl group, a $C_{6-10}$aryl*methyl group, a di-$C_{6-10}$aryl*methyl group or a tri-$C_{6-10}$aryl*methyl group is preferable. Examples of the protective group for the amino group as the substituent $R^0$ include, phthaloyl, methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-tri-methylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorpheoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl, cyclohexyloxycarbonyl, benzyl, naphthylmethyl, p-methylbenzyl, p-methoxybenzyl, p-chlorobenzyl, p-nitrobenzyl, benzhydryl, di-(p-tolyl)-methyl and trityl.

The substituent $R^4$ in the compound (I) of this invention is hydrogen, methoxy or formamido (HCONH—), preferably hydrogen.

The substituent $R^{13}$ in the compound (I) of this invention is hydrogen, methyl, hydroxyl or a halogen, preferably hydrogen. The halogen is fluorine, chlorine, bromine or iodine.

The substituent A in the compound (I) means an optionally substituted condensed cyclic group formed by combining an imidazole or pyrazole ring with a 5- or 6-membered nitrogen-containing aromatic heterocyclic ring to share a C-N bond with each other. The condensed cyclic group formed by combining an imidazole or pyrazole ring with a 5- or 6-membered nitrogen-containing aromatic heterocyclic ring to share a C-N bond with each other (hereinafter abbreviated as the condensed cyclic group $A^0$) is a group formed by removing one of hydrogen atoms attached to carbon atoms which constitute a ring formed by condensation of an imidazole ring or a pyrazole ring with a 5- or 6-membered nitrogen-containing aromatic heterocyclic ring to share a C-N bond with each other. The 5- or 6-membered nitrogen-containing aromatic heterocyclic ring which constitutes the condensed rin $A^0$ (hereinafter abbreviated as ring B or simply B) means a 5- or 6-membered aromatic heterocyclic ring which may contain, in addition to carbon atom and nitrogen atom, also oxygen atom and/or sulfur atom as the ring constituting atom. Therefore the condensed ring $A^0$ may be represented by the following general formula $A^1$, $A^2$ or $A^3$.

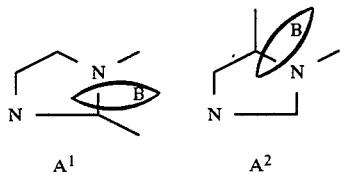

$A^1 \qquad A^2 \qquad A^3$

The figure ⌬ in the condensed rings $A^1$ to $A^3$ means that the said condensed rings are aromatic. Condensed cyclic group $A^0$ is a group formed by removing one of hydrogen atoms bound to the carbon atoms which constitute the said condensed rings $A^1$, $A^2$, $A^3$, which are sometimes hereinafter abbreviated as condensed cyclic group $A^1$, condensed cyclic group $A^2$ and condensed cyclic group $A^3$, respectively. As described above, a substituent A is a condensed cyclic group $A^0$ which may be substituted. That is, the substituent A means a condensed cyclic group $A^1$, a condensed cyclic group $A^2$, or a condensed cyclic group $A^3$, all of which may be substituted. The substituent on the condensed cyclic group $A^1$, $A^2$ or $A^3$ is a substituent which is bound to the carbon atom which constitutes the condensed ring and which has no chemical bond. Examples of the substituents on the condensed group $A^0$, i.e. condensed cyclic groups $A^1$, $A^2$ and $A^3$ are described below. the binding arm of the condensed cyclic group may be present at a carbon atom on the imidazole ring or pyrazole ring, or at a carbon atom on the ring B.

Examples of the condensed ring $A_1$ constituting the condensed cyclic group $A^1$ include the following.

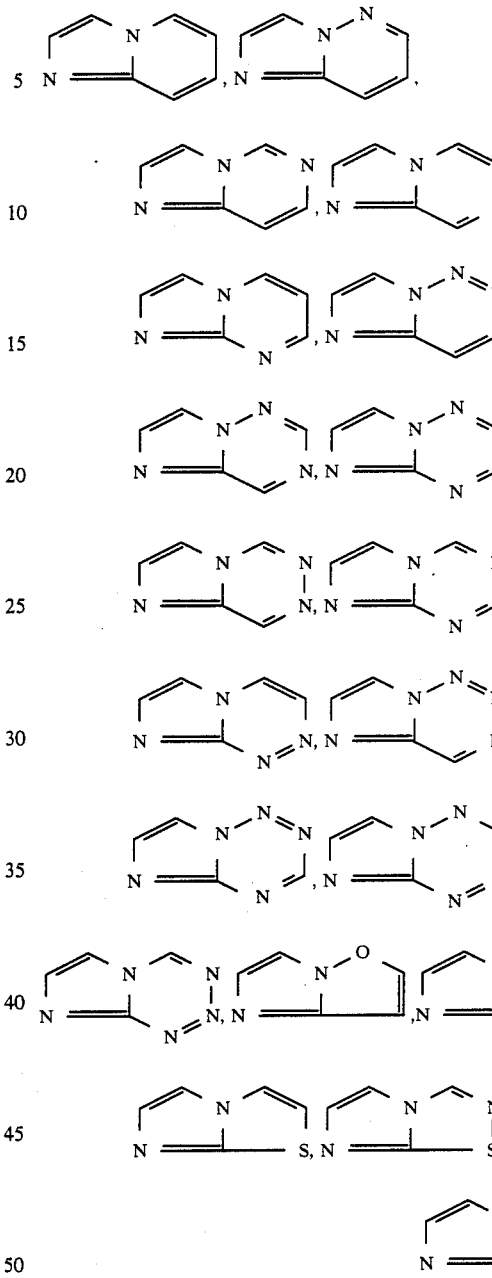

Examples of the condensed ring $A^2$ constituting the condensed cyclic group $A^2$ include the following.

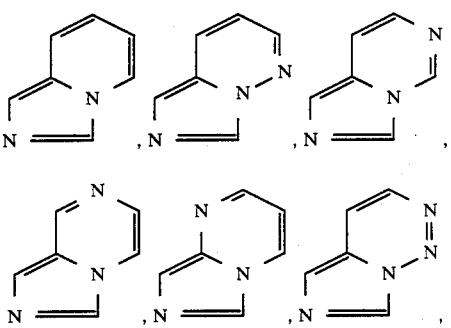

-continued

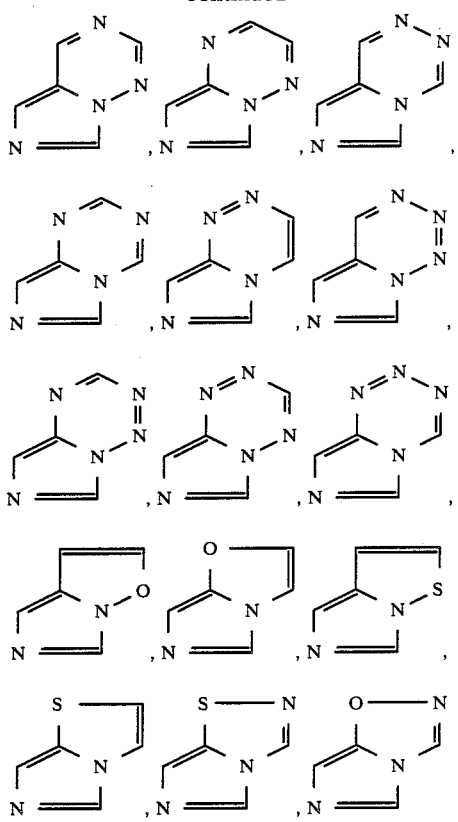

Examples of the condensed ring $A^3$ constituting the condensed cyclic group $A^3$ include the following.

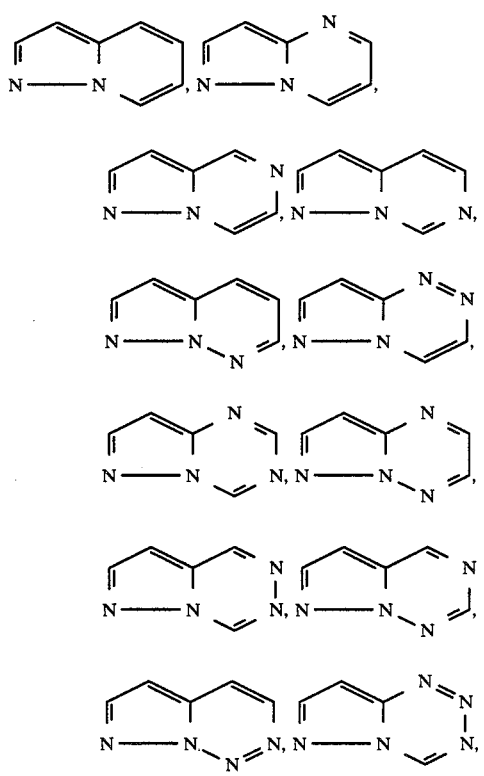

-continued

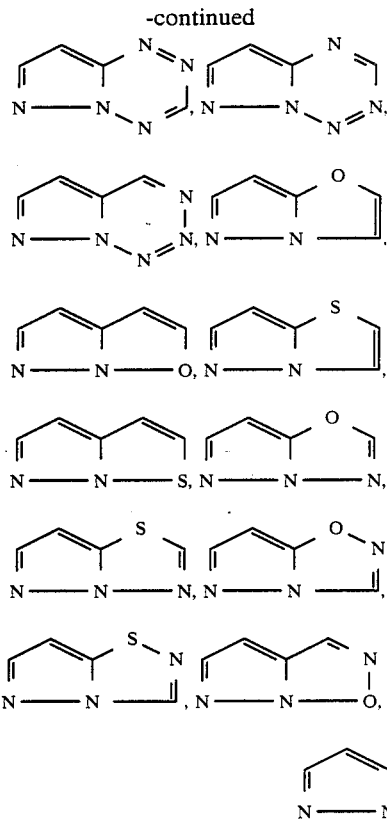

Examples of the substituent on the condensed cylic groups $A^1$, $A^2$ and $A^3$ include hydroxyl, a hydroxyC$_{1-6}$ alkyl group, a C$_{1-6}$ alkyl group, a C$_{2-6}$ alkenyl group, a C$_{2-6}$alkynyl group, a C$_{4-6}$ alkadienyl group, a C$_{3-10}$ cycloalkyl group, a C$_{5-6}$ cycloalkenyl group a C$_{3-10}$ cyclalkylC$_{1-6}$ alkyl group, a C$_{6-10}$ aryl group, a C$_{7-12}$aralkyl group, a di-C$_{6-10}$arylmethyl group, a tri-C$_{6-10}$arylmethyl group, a heterocyclic group, a C$_{1-6}$alkoxy group, a C$_{1-6}$alkoxyC$_{1-6}$alkyl group, a C$_{3-10}$cycloalkyloxy group, a C$_{6-10}$aryloxy group, a C$_{7-19}$aralkyloxy, mercapto, a mercaptoC$_{1-6}$alkyl group, sulfo, a sulfoC$_{1-6}$alkyl group, a C$_{1-6}$alkylthio group, a C$_{1-6}$alkylthioC$_{1-6}$alkyl group, a C$_{3-10}$cycloalkylthio group, a C$_{6-10}$arylthio group, a C$_{7-19}$aralkylthio group, amino, an aminoC$_{1-6}$alkyl group, a mono-C$_{1-6}$alkylamino group, a di-C$_{1-6}$alkylamino group, a mono-C$_{1-6}$alkylaminoC$_{1-6}$alkyl group, a di-C$_{1-6}$alkylaminoC$_{1-6}$alkyl group, a C$_{3-10}$cycloalkylamino group, a C$_{6-10}$arylamino group, a C$_{7-19}$aralkylamino group, a cyclic amino group, a cyclic aminoC$_{1-6}$alkyl group, a cyclic amino C$_{1-6}$alkylamino group, azido, nitro, a halogen, a halogenoC$_{1-6}$alkyl group, cyano, a cyanoC$_{1-6}$alkyl group, carboxyl group, a carboxyC$_{1-6}$alkyl group, a C$_{1-10}$alkoxy-carbonyl group, a C$_{1-10}$alkoxycarbonyl C$_{1-6}$alkyl group, a C$_{6-10}$aryloxy-carbonyl group, a C$_{7-19}$aralkyloxycarbonyl group, a C$_{6-10}$aryl-acyl+ group, a C$_{1-6}$ alkanoyl group, a C$_{2-6}$alkanoylC$_{1-6}$alkyl group, a C$_{3-5}$alkenoyl group, a C$_{6-10}$aryl-acyl+oxy group, a C$_{2-6}$alkanoyloxy group, a C$_{2-6}$alkanoyloxy C$_{1-6}$alkyl group, a C$_{3-5}$alkenoyloxy group, a carbamoyl C$_{1-6}$alkyl group, carbamoyl*, thiocarbamoyl*, carbamoyl*oxy, a carbamoyloxC$_{1-6}$alkyl group, a C$_{1-6}$alkanoylamino group, a C$_{6-10}$aryl-acyl+amino group, sulfonamido, carboxyamino, a C$_{1-10}$alkoxycarboxamido group, a C$_{6-10}$aryloxy-carboxamido group and a C$_{7-19}$aralkyloxy-carboxamido group.

Among the substituents described above, the "C4-6alkadienyl group" is for example a 1,3-butadienyl, the "C3-10cycloalkylC1-6alkyl group" is for example cyclopentylmethyl or cyclohexylmethyl, and the halogen is for example, fluorine, chlorine or bromine. All other groups include those described before.

Preferable examples of the substituent on the condensed cyclic groups $A^1$, $A^2$ and $A^3$ include a C1-6alkyl group, an aminoC1-6alkyl group, a mono-C1-6alkylamino group, a di-C1-6alkylamino group, a mono-C1-6alkylaminoC1-6alkyl group, a di-C1-6alkylaminoC1-6alkyl group, nitro, cyano, carboxyl, carbamoyl and a halogen. More preferable one includes a C1-6alkyl group.

There may be the same or different two or more (up to 5) of these substituents. Preferably the number of the substituents is one to two. Two adjacent substituents may combine to form an alicylic ring, an aromatic ring, or an heterocyclic ring. Examples of the substituents are following.

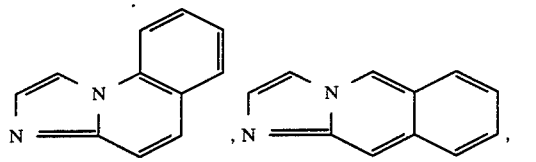

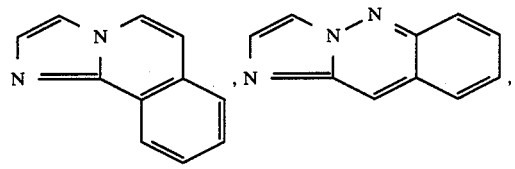

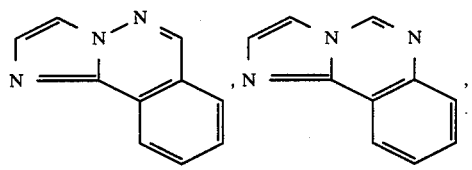

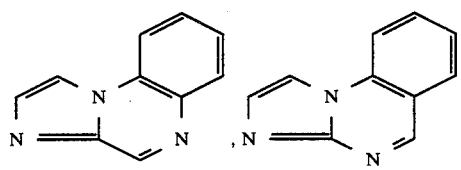

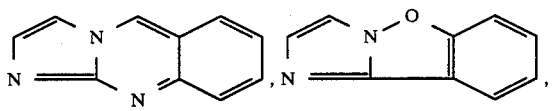

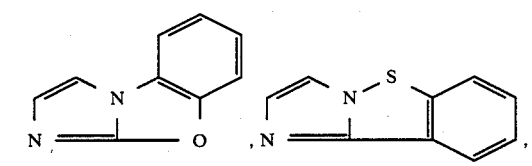

-continued

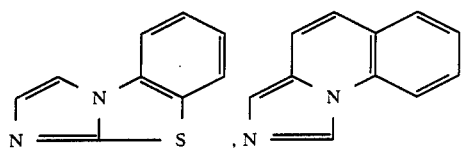

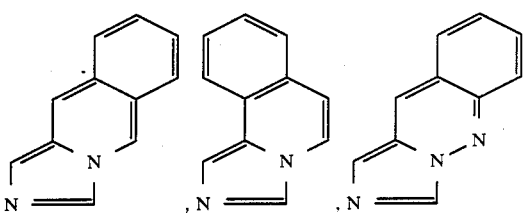

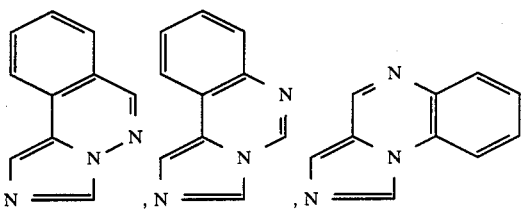

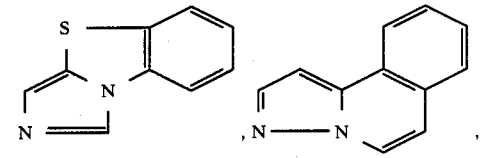

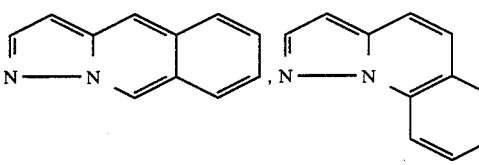

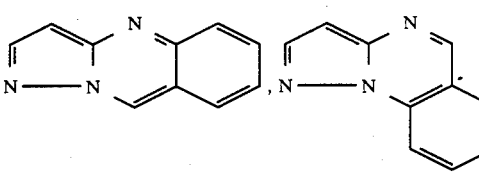

-continued
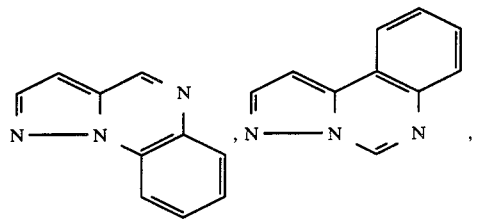
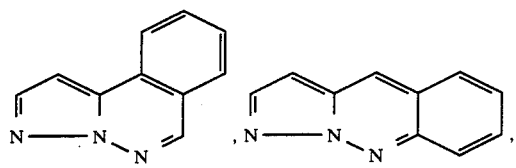
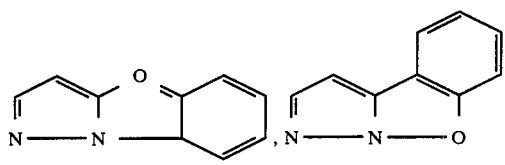
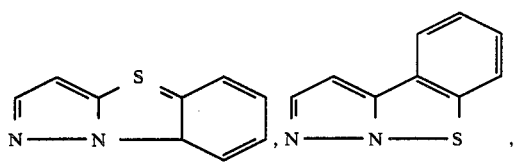
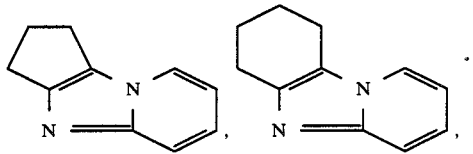
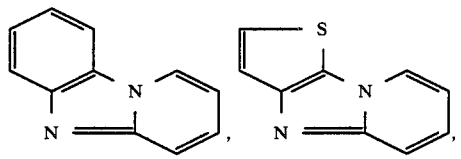
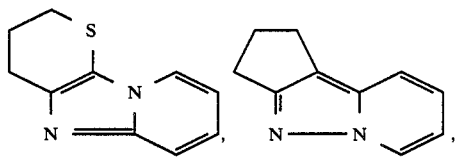
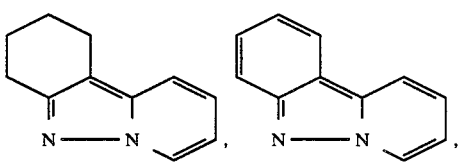
-continued
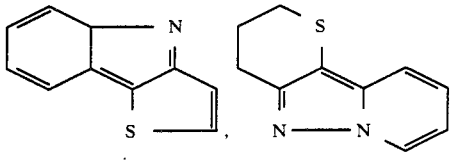
Ring B which constitutes the condensed ring $A^0$ is preferably a pyridine ring, a pyridazine ring, a pyrimidine ring or a pyrazine ring. Preferred condensed ring $A^1$ includes
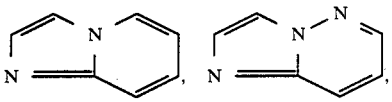
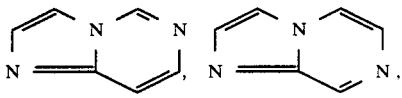
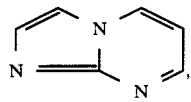
More preferred condensed ring $A^2$ includes
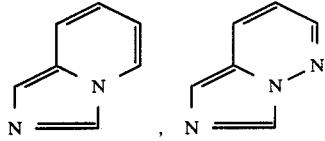
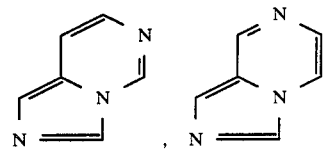
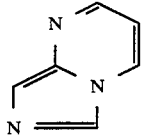
and more preferred condensed ring $A^3$ includes
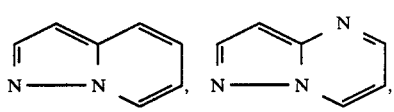
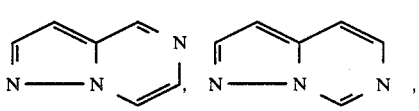

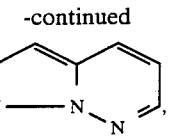

Among these condensed rings, most preferable ones are

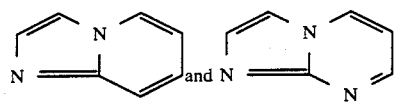

The condensed cyclic group $A^0$ is a group formed by removing one of hydrogen atoms attached to carbon atoms which constitute the condensed ring $A^0$. For example, the condensed cyclic group with corresponds to the condensed ring

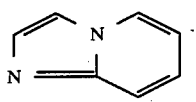

includes

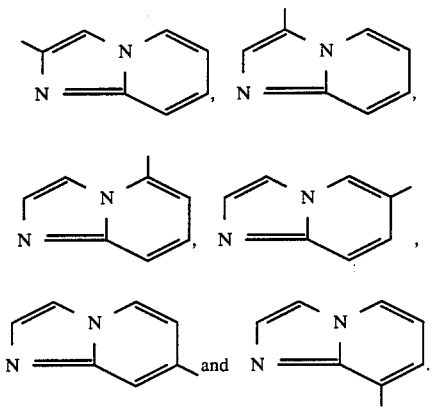

The compound (I) may be a salt or ester thereof. Among the salts of the compound (I), especially pharmaceutically acceptable salts thereof are used when the compound (I) is applied as an antimicrobial agent, and other salts re utilzied as intermediates for synthesis.

Examples of the salt of the compound (I) include the inorganic base salts, ammonium salts, organic base salts, inorganic acid addition salts, organic acid addition salts, and basic amino acid salts. Inorganic bases that can form the inorganic base salt include alkali metals (e.g. sodium, potassium), and alkaline earth metals (e.g. calcium); organic bases that can form the organic base salts include procaine, 2-phenylethylbenzylamine, dibenzylethylenediamine, ethanolamine, diethanolamine, trishydroxymethylaminomethane, polyhydroxyalkylamine and N-methylglucosamine; inorganic acids that can form the inorganic acid addition salts include hydrochloric acid, hydrobromic acid, sulfuric acid, nitric acid and phosphoric acids; organic acids that can form the organic acid addition salts include p-toluenesulfonic acid, mehtanesulfonic acid, formic acid, trifluoroacetic acid, and maleic acid; and basic amino acids that can form the basic amino acid salts include lysine, arginine, ornithine and histidine. Among these salts, the base salts (i.e. inorganic base salts, ammonium salts, organic base salts and basic amino acid salts) mean base salts which can be formed at the carboxyl group at the 4 position of the compound (I) or base salts which can be produced when an acid group, such as carboxyl or sulfo group is present in the substituent $R^0$ or in the substituent A, and the acid addition salts (i.e. inorganic acid addition salts and organic addition salts) means acid addition salts which can be formed when a basic group, such as amino, an mono-alkylamino group, a di-alkylamino group, a cycloalkylamino group, an arylamino group, an aralkylamino group, a cyclic amino group or a nitrogen-containing heterocyclic group, is present in the substituent $R^0$ in the substituent A of the compound (I).

The ester derivatives of the compound (I) mean esters which can be formed by esterification of the carboxyl group(s), particulary the carboxyl group at the 4 position, and are ① the esters which can be utilized as intermediates for synthesis and ① esters which are metabolically unstable, nontoxic and suitable for the oral administration. Esters which can be utilized as the intermediates for synthesis include $C_{1-6}$alkyl* $C_{2-6}$alkenyl, $C_{3-10}$cycloalkyl, $C_{3-10}$cycloalkylC$_{1-6}$alkyl, $C_{6-10}$aryl*, $C_{7-12}$aralkyl*, di-$C_{6-10}$aryl-methyl, tri-$C_{6-10}$arylmethyl and substituted silyl esters. Examples of the "$C_{1-6}$alkyl* group" which constitutes the $C_{1-6}$alkyl*-ester include methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2-trichloroechyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-1-oxido-2-methyl, methylsulfinylmethyl and 2-cyano-1,1-dimethylethyl; examples of the $C_{2-6}$alkenyl group which constitutes the $C_{2-6}$alkenyl ester include also here those described above, such as vinyl, allyl, 1propenyl, isopropenyl, 1-butenyl, 2-butenyl, 3-butenyl, methallyl, 1,1-dimethylallyl or 3-methyl-3-butenyl; examples of the $C_{3-10}$cycloalkyl group which constitutes the $C_{3-10}$cycloalkyl ester include also here those described above, such as cyclopropyl, cyclobutyl, cyclopentyl, cyclohexyl, cycloheptyl, norbornyl or adamantyl; examples of the $C_{3-10}$cycloalkylC$_{1-6}$alkyl group which constitutes the $C_{3-10}$cycloalkyl $C_{1-6}$alkyl ester include also here those described above, such as cyclopropylmethyl, cyclopentylmethyl or cyclohexylmethyl; examples of the "$C_{6-10}$aryl* group" which constitutes the $C_{6-10}$aryl* ester include phenyl, α-naphthyl, β-naphthyl, biphenylyl, p-nitrophenyl and p-chlorophenyl; examples of the $C_{7-12}$aralkyl* group which constitutes the $C_{7-12}$aralkyl* ester include benzyl, 1-phenylethyl, 2-phenylethyl, phenylpropyl, naphthylmethyl, p-nitrobenzyl, p-methoxybenzyl, 1-indanyl, phenacyl and 3,5-di-tert-butyl-4-hydroxybenzyl; examples of the di-$C_{6-10}$aryl-methyl group which constitutes the di-$C_{6-10}$aryl-methyl ester include also here those described above, such as benzhydryl or bis(p-methoxyphenyl)-methyl; examples of the tri-$C_{6-10}$aryl-methyl group which constitutes the tri-$C_{6-10}$aryl-methyl ester include also here those described above, such as trityl; examples of the substituted silyl group which constitutes the substituted silyl ester include also here those described above, such a trimethylsilyl, tert-butyldimethylsilyl or —Si(CH$_3$)$_2$CH$_2$CH$_2$Si(CH$_3$)$_2$—.

As the metabolically unstable, nontoxic esters, those which have already been established in the field of penicillin and cephalosporin especially for the purpose of the oral administration are conveniently applicable also to this invention. Examples of the metabolically unstable, nontoxic esters include $C_{2-6}$alkanoyloxy $C_{1-6}$alkyl, 1-($C_{1-6}$alkoxy)$C_{1-6}$alkyl, 1- alkylthio)$C_{1-6}$alkyl and 1-($C_{1-6}$alkoxycarbonyloxy)$C_{1-6}$alkyl esters. Examples of the $C_{2-6}$alkanoyloxy $C_{1-6}$alkyl ester include acetoxymethyl, 1-acetoxyethyl, 1-acetoxybutyl, 2-acetoxyethyl, propionyloxymethyl, pivaloyloxymethyl and 1-(2-methyl-2-methoxypropionyloxy)ethyl esters. Examples of 1-($C_{1-6}$alkoxy)$C_{1-6}$alkyl ester include methoxymethyl, ethoxymethyl, isopropoxymethyl, ethoxymethyl, isopropoxymethyl, 1-methoxyethyl and 1-ethoxyethyl esters. Examples of the 1-($C_{1-6}$alkylthio)$C_{1-6}$alkyl ester include methylthiomethyl and ethylthiomethyl esters. The examples of the 1-($C_{1-6}$alkoxycarbonyloxy)$C_{1-6}$alkyl ester include 1-(ethoxycarbonyloxy)ethyl and 1-(tert-butoxycarbonyloxy)ethyl esters. In addition to those descirbed above, phthalidyl esters are also applicable. This invention includes, in addition to the ester derivatives described above, pharmaceutically acceptable compounds which are able to be converted into the compound (I) in the organism. Among them, a $C_{2-6}$alkanoyloxy$C_{1-6}$alkyl ester is preferable.

When the compound (I) has a hydroxyl group, the hydroxyl group may be protected. As the hydroxyl-protective groups, all of those that are usable for protection of a hydroxyl group in the field of β-lactam and in the field of organic chemistry are applicable, and a $C_{2-6}$akanoyl group, a substituted oxycarbonyl, tert-butyl, $C_{7-12}$aralkyl*, di-$C_{6-10}$arylmethyl, tri-$C_{6-10}$arylmethyl, 1-($C_{1-6}$alkoxy)$C_{1-6}$alkyl, 1($C_{1-6}$alklthio)$C_{1-6}$alkyl, and substituted silyl group as described above, or an acetal residue, such as 2-tetrahydropyranyl or 4-methoxy-4-tetrahydropyranyl is used.

When the compound (I) has another amino group in addition to the amino group described above, the former amino group may be also protected. The protective groups for the said amino group are the same as described as the aminoprotective groups described before.

Among the compound (I), those having a nitrogen-containing heterocyclic group ($R^a$) or an acyl group ($R^b$) as the substituent $R^0$ have a broad spectrum of antibacterial activity and can be used for prevention and treatment of various diseases due to pathogenic bacteria in man and animals, such as a respiratory tract and urinary tract infection. The antibacterial spectrum of the antimicrobial compound (I) or ($R^0=R^a$ or $R^b$, or a pharmaceutically acceptable salt, thereof, or a metabolically unstable nontoxic ester thereof is characterized by;

(1) a very high activity against many kinds of Gram-negative bacteria, (2) a very high activity against Gram-positive bacteria, such as *Staphylococcus aureus, Corynebacterium diphtheriae,*

(3) a remarkable antibacterial action against *Pseudomonas aeruginosa* which is not sensitive to the usual treatment with an antibiotic agent of cephalosporin series, and (4) a high activity against many β-lactamase-producing Gram-negative bacteria such as the genus Escherichia, the genus Enterobacter, the genus Serratia or the genus Proteus.

The antimicrobial compound (I) or ($R^0=R^a$ or $R^b$) of this invention or a pharmaceutically acceptable salt thereof, or° a metabolically unstable, nontoxic ester thereof is also characterized by an excellent stability, high blood level, long duration of the effect and remarkable distribution in the tissues.

How to make the compound (I) of this invention, or a salt or ester thereof is described in detail in the following. The processes described hereafter may be all conventional as reactions per se, and conventional procedures and analogous ones thereto may be applied.
Method of Production (1): Synthesis of the compound (II), [(I), $R^0=$hydrogen]

For example, a 7-amino compound (II) [(I), $R^0=$hydrogen] or a salt or ester thereof can be synthesized by reacting a compound of the general formula,

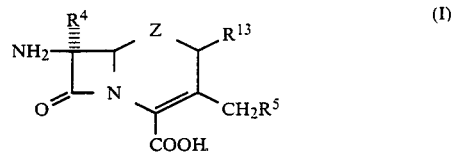

wherein the symbol $R^5$ is hydroxyl, an acyloxy group, carbamoyloxy, a substituted carbamoyloxy group or a halogen, and other symbols are of the same meaning as defined above, or a salt or ester thereof, with a thiol compound of the general formula ASH wherein A is an optionally substituted condensed cyclic group formed by combining an imidazole or pyrazole ring with a 5- or 6-membered nitrogen-containing aromatic heterocyclic ring to share a C-N bond with each other, or a salt thereof. That is, this reaction is shown by the following reaction formula.

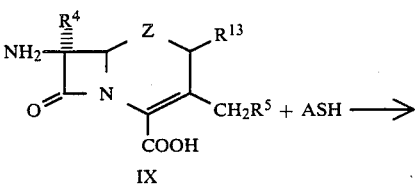

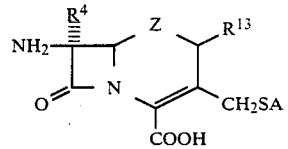

(II) ((I), $R^0$ = hydrogen.
(including a salt or ester thereof)

wherein the symbols are of the same meaning as defined above.

The starting compound (IX) or a salt or ester thereof is easily obtained by usihg a known method or one analogous thereto. As salt and ester of the compound (IX), those of the compound (II) described below are also here applicable.

Examples of the acyloxy group represented by $R^5$ described above include the acyl+oxy group described above, among which acetoxy, chloroacetoxy, propionyloxy, butyryloxy, pivaloyloxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, o-carboxybenzoyloxy, o-(ethoxycarbonylcarbamoyl) benzoyloxy and o-(ethoxycarbonylsulfamoyl)benzoyloxy are particularly preferable. Examples of the substituted carbamoyloxy group represented by the symbol $R^5$ include those described above, among which methylcarbamoyloxy and N,N-dimethylcarbamoyloxy are partiuclarly preferable. The halogen represented by the symbol $R^5$ is preferably chlorine, bromine, or iodine. The thiol compound ASH and the salt thereof are described below in detail.

This reaction proceeds in the same way as described above, even when the amino group at the 7 position is protected to yield the same compound as that synthesized by Method of Production (4), and followed by, if necessary, removal of the protective group to produce the 7-amino compound (II) [(I), $R^0$=hydrogen].

Method of Production (2): Synthesis of the compound ($I^a$) ($R^0 = R^a$; $R^a$ is a nitrogen-containing heterocyclic group).

(2-1): The compound ($I^a$) ($R^0 = R^a$) can be synthesized for example, by reacting the 7-amino compound (II) obtained according to the Method of Production (1), or a salt or ester thereof (the salt and ester are described below) with a compound of the general formula $R^aHal$ ($R^a$ is a nitrogen-containing heterocyclic group; and Hal is halogen, such as fluorine, chlorine, bromine or iodine), or a salt thereof. This reaction is written by the following reaction formula.

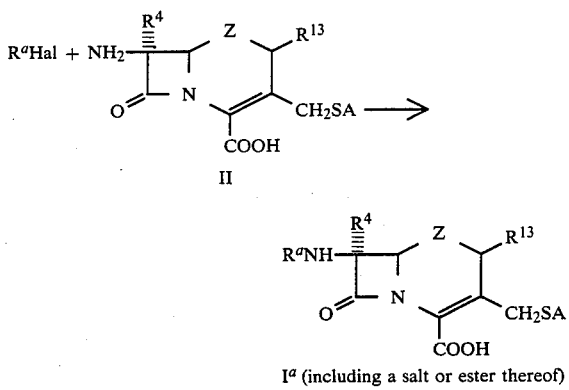

$I^a$ (including a salt or ester thereof)

wherein the symbol $R^a$ is a nitrogen-containing heterocyclic group and the other symbols are of the same meaning as defined above.

A fluorine atom is most frequently used as the halogen (Hal) of the compound $R^aHal$. Examples of the salt of the compound $R^aHal$ include inorganic acid addition salts, such as hydrochlorides, hydrobromides, sulfates, nitrates or phosphates and organic acid addition salts, such as formates, acetates, trifluoroacetaees, methanesulfonates or p-toluenesulfonates. The reaction is carried out by mixing the compound $R^aHal$ or a salt thereof with the 7-amino compound (II) or a salt or ester thereof generally in water or an aqueous solvent at room temperature (about 15° to about 30° C.; the same as in the following). To prevent hydrolysis of the compound $R^aHal$ prior to the reaction with the compound (II), adjustment of pH is 6 to 8.5. An acid-binding agent may be used to remove the hydrogen halide formed by the reaction out of the reaction system. Examples of the acid-binding agents include inorganic bases, such as sodium acid-binding agents include inorganic bases, such as sodium carbonate, potassium carbonate, calcium carbonate or sodium hydrogen carbonate; tertiary amines, such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; and alkylene oxides, such as propylene oxide or epichlorohydrin. To prevent overalkalinity, an inorganic acid, such as hydrochloric acid, hydrobromic acid, sulfuric acid, nitric acid or phosphoric acid may be sometimes used. When an aqueous solvent is used, the organic solvnts which are used by mixing with water include ethers, such as dioxane, tetrahydrofuran, diethyl ether, tert-butyl methyl ether or diisopropyl ether, amides, such as formamide, N,N-dimethylformamide or N,N-dimethylacetamide, or ketones, such as acetone, methyl ethyl ketone or methyl isobutyl ketone, dimethyl sulfoxide, sulfolane and hexamethyl phosphoramide. The compound $R^aHal$ is usually used in an amount of about 1 to 3 moles, preferably about 1 to 2 moles, per 1 mole of the 7-amino compound (II). The reaction time varies according to the species of the 7-amino compound (II) and the compound $R^aHal$, the kind of the solvent, the reaction temperature, etc., being usually about 1 minute to 48 hours, preferably about 15 minutes to 3 hours.

The compound $R^aHal$ and a salt thereof can be synthesized easily by known methods or ones analogous thereto.

For examples, by this method, the compound of the following formula can be synthesized.

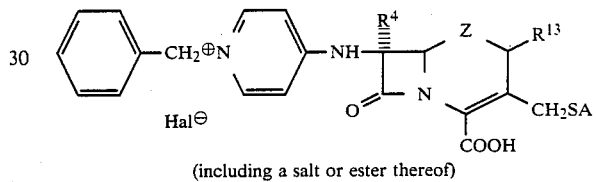

(including a salt or ester thereof)

When the compound $R^aHal$ is so reactive that the compound is susceptible to hydrolysis, the reaction may be carried out, for example, in anhydrous dimethylfulfoxide, in the presence of an organic base, such as anhydrous triethylamine. By this method, for example, the following compound can be synthesized.

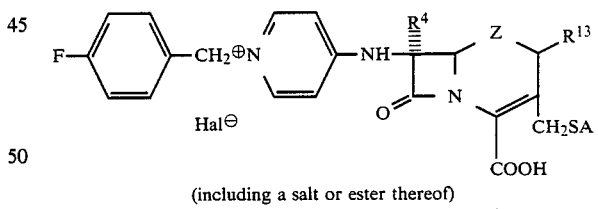

(including a salt or ester thereof)

The reaction may be carried out in the presence of an organic acid, such as p-toluenesulfonic acid, methanesulfonic acid, ethanesulfonic acid, acetic acid, butyric acid or carbonic acid, or an inorganic acid, such as hydrochloric acid or sulfuric acid. Also in these cases, fluorine is most frequently used as the halogen (Hal) in the compound $R^aHal$. The reaction is usually carried out in a solvent such as dimethylformamide, tetrahydrofuran, dioxane, chloroform, methanol, acetonitrile, benzene, acetone or water, or in a mixture thereof. The reaction temperature is about 0° to 150° C., preferably about 20° to 80° C. The reaction time is usually about 30 minutes to 20 hours. By this. method, for example, the following compound can be synthesized.

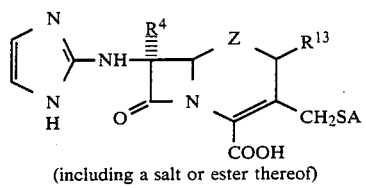

(including a salt or ester thereof)

(2-2): The compound (I$^a$) (R$^0$=R$^a$) can be also synthesized by reacting the starting compound (IX) used in the Method of Production (1) or a salt or ester thereof with the compound R$^a$Hal or a salt thereof, followed by the reaction with a thiol compound ASH wherein A is of the same meaning as defined above or a salt thereof. This reaction is written by the following reaction formula.

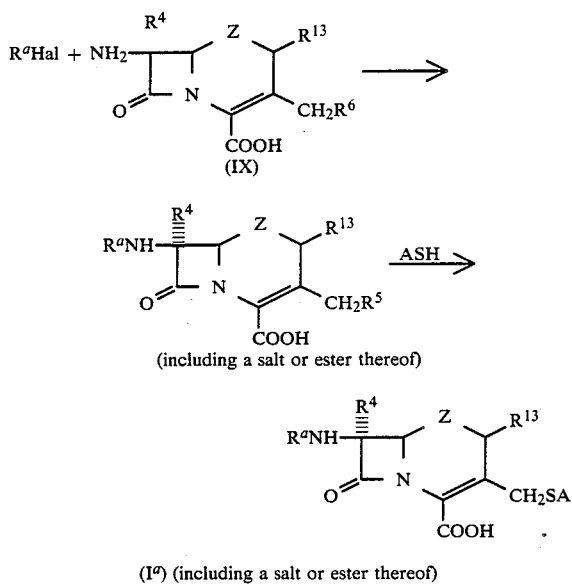

(I$^a$) (including a salt or ester thereof)

wherein the symbol R$^a$ is a nitrogen-containing heterocyclic group, and other symbols are of the same meaning as defined above. The starting compound (IX) or a salt or ester thereof and the compound R$^a$Hal or a salt thereof are also here those described above. The thiol compound ASH or a salt thereof is described below in detail. The reaction is carried out in the same way as described in the Method of Production (2-1) and the Method of Production (1). Method of Production (3): Synthesis of the compound (I$^b$) (R$^0$=R$^b$;R$^b$ is an acyl group).

(3-1) The compound (I$^b$) (R$^0$=R$^b$) can be synthesized for example, by reacting the 7-amino compound (II) or a salt or ester thereof obtained in the Method of Production (1) with a carboxylic acid of the general formula R$^b$OH wherein R$^b$ is an acyl group, or a salt or reactive derivative thereof. This reaction is written by the following reaction formula,

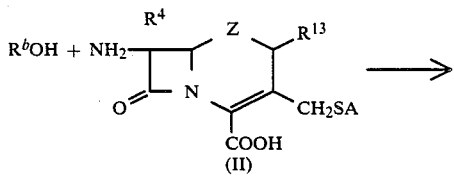

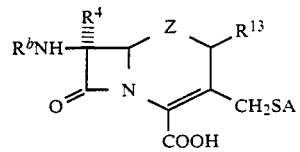

(I$^b$) (including a salt or ester thereof)

wherein the symbol R$^b$ is an acyl group, and other symbols are of the same meaning as defined above.

This method consists in acylation of the 7-amino compound (II) with a carboxylic acid R$^b$OH or a salt or reactive derivative thereof. In this method the carboxylic acid R$^b$OH is used in the free form, or as a salt or reactive derivative thereof as an acylating agent of the amino group at the 1 position of the 7-amino compound (II). That is, a free acid R$^b$OH or an inorganic or organic salt of the free acid R$^b$OH, or a reactive derivative of the free acid R$^b$OH, such as an acid halide, an acid azide, an acid anhydride, a mixed acid anhydride, an active amide, an active ester and an active thioester are used for the acylation. Examples of the inorganic salt include alkali metal salts (e.g. sodium salts, potassium salts) and alkaline earth metal salts (e.g. calcium salts). Examples of the organic salt include trimethylamine salts, triethylamine salts, tert-butyldimethylamine salts, dibenzylmethylamine salts, benzyldimethylamine salts, N,N-dimethylaniline salts, pyridine salts, and quinoline salts. Examples of the acid halide include acid chlorides and acid bromides. Examples of the mixed acid anhydride include the mono-C$_{1-6}$alkyl carbonic mixed acid anhydrides (e.g. mixed acid anhydrides of a free acid R$^b$OH with a monomethyl carbonic, monoethyl carbonic, mono-tert-butyl carbonic, monobenzyl carbonic, mono(p-nitrobenzyl)carbonic or monoallyl carbonic. acid), the C$_{1-6}$aliphatic carboxylic acid mixed acid anhydrides (e.g. mixed acid anhydrides of a free acid R$^b$OH with acetic acid, trichloroacetic acid, cyanoacetic acid, propionic acid, butyric acid, isobutyric acid, valeric acid, isovaleric acid, pivalic acid, trifluoroacetic acid, trichloroacetic acid, or acetoacetic acid, and the C$_{7-12}$aromatic carboxylic acid mixed acid anhydrides (e.g. mixed acid anhydrides of a free acid R$^b$OH with benzoic acid, p-toluic acid or p-chlorobenzoic acid), and the organic sulfonic acid mixed acid anhydrides (e.g. mixed acid anhydride of a free acid R$^b$OH with methanesulfonic acid, ethanesulfonic acid, benzenesulfonic acid or p-toluenesulfonic acid). Examples of the active amide include amides with a nitrogen-containing heterocyclic compound (e.g. acid amides of a free acid R$^b$OH with pyrazole, imidazole or benzotriazole, and these nitrogen-containing heterocyclic compounds which may be substituted by the C$_{1-6}$alkyl group, C$_{1-6}$alkoxy group, halogen, oxo, thioxo, C$_{1-6}$alkylthio group described above). As the active esters, any of those that can be used for this purpose in the field of synthesis of β-lactams and peptides are applicable including, in addition to the organic phosphoric ester (e.g. diethoxyphosphoric or diphenoxyphosphoric ester), a p-nitrophenyl, 2,4-dinitrophenyl, cyanomethyl, pentachlorophenyl, N-hydroxysuccinimido, N-hydroxyphthalimido, 1-hydroxybenzotriazole, 6-chloro-1-hydroxybenzotriazole or 1-hydroxy-1H-2-pyridone ester. Examples of the active thioester include the esters with an aromatic heterocyclic thiol compound (e.g.

2-pyridyl thiol or 2-benzothiazolyl thiol ester and these heterocyclic rings may be substituted by the $C_{1-6}$alkyl group, $C_{1-6}$alkoxy group, a halogen and $C_{1-6}$alkylthio group described above).

The 7-amino compound (II) is used in the free form or in the form of a salt or ester thereof. Examples of the salt of the 7-amino compound (II) include inorganic base salts, ammonium salts, organic base salts, inorganic acid addition salts and organic acid addition salts. The inorganic base salts include alkali metal salts (e.g. sodium and potassium salts), and alkaline earth metal salts (e.g. calcium salts), and the organic base salts include trimethylamine, triethylamine, tert-butyldimethylamine, dibenzylemthylamine, benzyldimethylamine, N,N-dimethylaniline, pyridine and quinoline salts and the inorganic acid addition salts include hydrochlorides, hydrobromides, sulfates, nitrates and phosphates, and the organic acid addition salts include formates, acetates, trifluoroacetates, methanesulfonates and p-toluenesulfonates. As the ester of the 7-amino compund (II), the ester described above as the ester derivatives of the compound (I) are applicable. That is, the esters include $C_{1-6}$alkyl*, $C_{2-6}$alkenyl, $C_{3-10}$cycloalkyl, $C_{3-6}$cycloalkylC$_{1-6}$alkyl, $C_{6-10}$aryl*, $C_{7-12}$aralkyl*, di-$C_{6-10}$arylmethyl, tri-$C_{6-10}$arylmethyl and $C_{2-6}$alkanoyloxyC$_{1-6}$alkyl esters. The starting compound $R^bOH$ or a salt or reactive derivative thereof can be produced easily with a known method or one anoalogous thereto. The reactive derivatives of the compound $R^bOH$ may be reacted with the quaternary ammonium compound (II), after isolation from the reaction mixture, or the reaction mixture containing a reactive derivative of the compound $R^bOH$ may be, without being isolated, reacted with the quaternary ammonium compound (II). When the carboxylic acid $R^bOH$ is used in the form of a free acid or a salt, an appropriate condensing agent is used. Examples of the condensing agent include a N,N'-disubstituted carbodiimide, such as N,N'-dicyclohexylcarbodiimide, an azolide, such as N,N'-carbonyldiimidazole or N,N'-thiocarbonyldiimidazole, a dehydrating agent, such as N-ethoxycarbonyl-2-ethoxy-1,2-dihydroquinoline, phosphorus oxychloride or alkoxyacetylene and a 2-halogenopyridinium salt, such as 2-chloropyridiniummethyl iodide or 2-fluoropyridiniummethyl iodine. When any of these condensing agets is used, the reaction is supposed to proceed through a reactive derivative of the carboxylic acid $R^bOH$. The reaction is generally carried out in a solvnet and a solvent which does not interfere with the reaction is selected appropriately. Examples of the solvent include ethers, such as dioxane, tetrahydrofuran, diethyl ether, tert-butyl methyl ether, diisopropyl ether or ethyleneglycol dimethyl ether, esters, such as ethyl formate, ethyl acetate or n-butyl acetate, halogenated hydrocarbons, such as dichloromethane, chloroform, carbon tetrachloride, trichlene or 1,2-dichloroethane, hydrocarbons, such as n-hexane, benzene or toluene, amides, such as formamide, N,N-dimethylformamide or N,N-dimethylacetamide, ketones, such as acetone, methylethylketone or methylisobutylketone, nitriles, such as acetonitrile or propionitrile; dimethyl sulfoxide, sulfolane, hexamethylphosphoramide and water, which ae used alone or as a mixture thereof. The acylating agent ($R^bOH$) is usually used in an amount of about 1 to 5 moles, preferably about 1 to 2 moles, per 1 mole of the 7-amino compound (II). The reaction is conducted at about $-80°$ to $80°$ C., preferably at about $-40°$ to $50°$ C., and most desirably at about $-30°$ to $30°$ C. The reaction time varies depending on the species of the 7-amino compound (II) and the carboxylic acid $R^bOH$, the kind of the solvent (also the mixing ratio if a mixed solvent is used), the reaction temperature, etc., being usually about 1 minute to 72 hours, preferably about 15 minutes to 3 hours. When an acid halide is used as the acylating agent, the reaction can be conducted in the presence of an acid binding agent to remove the liberated hydrogen halide out of the reaction system. Examples of the acid binding agent include inorganic bases, such as sodium carbonate, potassium carbonate, calcium carbonate or sodium hydrogen carbonate; tertiary amines, such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine and alkyleneoxides, such as propyleneoxide or epichlorohydrin.

The compound (VII) described above can be synthesized, for example, by the method described above. The reaction formula is written by the following formula.

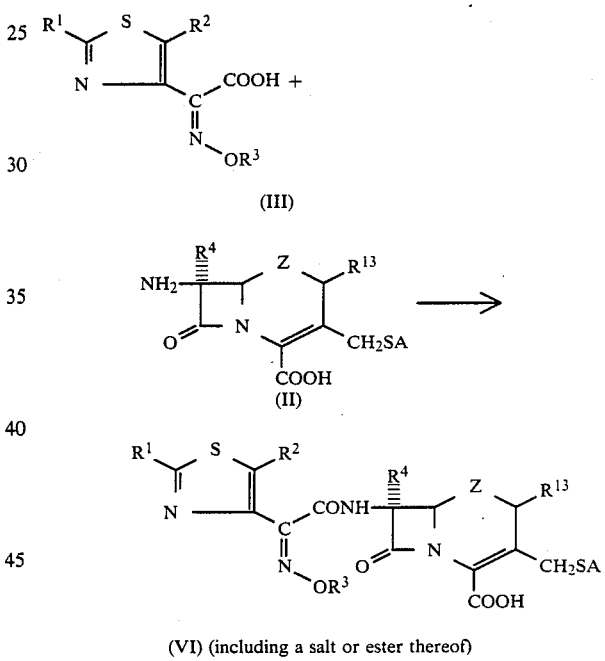

(VI) (including a salt or ester thereof)

The carboxylic acid (III) can be easily produced by a known method or one analogous thereto.

(3-2): The compound ($I^b$) ($R^0=R^b$) can be synthesized by reacting a compound of the general formula:

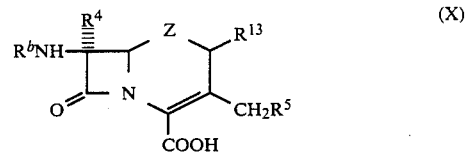

wherein $R^b$ is an acyl group and other symbols are of the same meaning as defined above, or a salt or ester thereof, with a thiol compound of the general formula ASH wherein A is of the same meaning defined above, or a salt thereof. The reaction is written by the following reaction formula.

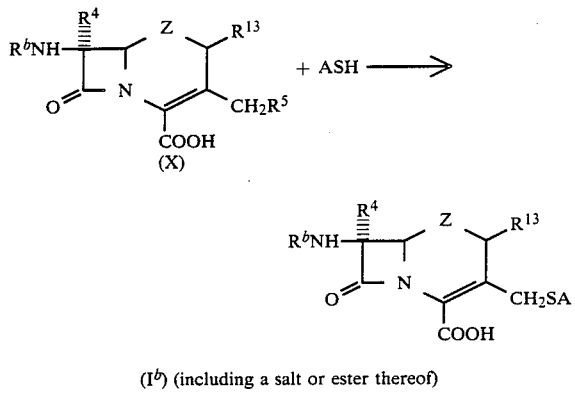

(I^b) (including a salt or ester thereof)

wherein the symbol $R^b$ is an acyl group and the symbols Z, $R^4$, $R^{13}$, $R^5$ and A are of the same meaning as defined above. This reaction is essentially the same as that described in the Method of Production (1), and by this method the compound (I^b) ($R^0=R^b$) is synthesized by a nucleophilic substitution reaction of the compound (X) or a salt or ester thereof with a thiol compound ASH or a salt thereof. In the compound (X), $R^5$ is hydroxyl, an acyloxy group, carbamoyloxy, a substituted carbamoyloxy group or halogen. The compound (X) is used in a free form or in the form of a salt or ester thereof. The salt or ester of the compound (X) used is made of the salt or ester of the 7-amino compound (II) described in the Method of Production (3-1). The compound (X) or a salt or ester thereof and the thiol compound ASH or a salt thereof can be produced easily by a known method or one analgous thereto.

For example, the thiol compound ASH or a salt thereof can be produced by the methods described in J. Med. Chem., 18, 1253(1975); Justus Liebigs Ann. Chem., 699, 127(1966); Comprehensive Heterocyclic Chemistry, Volume 5 edited by Alan R. Katritzky, published by Pergamon Press.; J. Het. Chem., 17, 1351(1980), or according to the following equation.

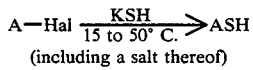
(including a salt thereof)

wherein the symbols have the same meaning as defined above. The starting compound A-Hal is known or can be produced by per se known methods (e.g. J. Med. Chem., 26, 357(1983); 27, 206(1984); J. Org. Chem., 45, 3738(1980); 49, 4021(1984); Bull. Soc. Chem. Fr., 1972, 3503., Chem. Pharm. Bull., 31, 2540 (1983); Aust. J. Chem., 36, 1215(1983); Synthesis 1981, 987; U.S. Pat. No. 4,478,835).

The thiol compound ASH may be used also in the form of a salt. Examples of the salt of the thiol compound ASH include alkali matal salts (e.g. sodium or potassium salts) and alkaline earth metal salts (e.g. calcium salts).

The nucleophilic reaction of the thiol compound ASH or a salt thereof and the compound (X) is conventional as reaction per se, which is usually conducted in a solvent. Examples of the solvent include all of the solvents used in the Method of Production (3-1), such as ethers, ester, halogenated hydrocarbons, hydrocabons, amides, ketones, nitriles or water and alcohols, such as methanol, ethanol n-propanol, isopropanol, ethylene glycol or 2-methoxyethanol.

(3-2-1): When $R^5$ is an acyloxy group, carbamoyloxy or a substituted carbamoyloxy group;

Preferable solvents are water or a mixed solvents consisting of water and an organic solvent miscible with water, and among organic solvents miscible with water, acetone, methylethylketone and acetonitrile are preferable. The thiol compound ASH or a salt thereof is usually used in an amount of about 1 to 5 moles, preferably about 1 to 3 moles, per 1 mole of the compound (X) or a salt or ester thereof. The reaction is conducted at about 10° to 100° C., preferably at about 30° to 80° C. The reaction times varies depending on the species of the compound (X) and the compound ASH, the kind of the solvent (also the mixing ratio when a mixed solvent is used), the reaction temperature, etc., being usually about 30 minutes to 5 days, preferably about 1 to 5 hours. The reaction is carried out advantageously at pH 2 to 8, preferably at a neutral region, i.e. at pH 5 to 8. This reaction proceeds more easily in the presence of usually about 2 to 30 equivalents of an iodide or a thiocyanate. Examples of the iodide or a thiocyanate include sodium iodide, potassium iodide, sodium thiocyanate and potassium thiocyanate. In addition to the salts described above, a surface-active quaternary ammonium salt, such as trimethylbenzylammonium bromide, triethylbenzylammonium bromide or triethylbenzylammonium hydroxide may be added sometimes to make the reaction proceed smoothly.

(3-2-2): When $R^5$ is hydroxyl;

According to the method described, for example, in Japanese Laid-Open Patent Application No. 43979/83, the reaction is conducted in the presence of an organic phosphorus compound. Examples of the organic phosphorus compound include o-phenylenephosphorochloridate, o-phenylenephosphorofluoridate, methyl o-phenylenephosphate, ethyl o-phenylenephosphate, propyl o-phenylenephosphate, isopropyl o-phenylenephosphate, butyl o-phenylenephosphate, isobutyl o-phenylenephosphate, sec-butyl o-phenylenephosphate, cyclohexyl o-phenylenephosphate, phenyl o-phenylenephosphate, p-chlorophenyl o-phenylenephosphate, p-acetyl o-phenylenephosphate, 2-chloroethyl o-phenylenephosphate, 2,2,2-trichloroethyl o-phenylenephosphate, ethoxycarbonylmethyl o-phenylenephosphate, carbamoylmethyl o-phenylenephosphate, 2-cyanoethyl o-phenylenephosphate, 2-methylsulfonylethyl o-phenylenephosphate, benzyl o-phenylenephosphate, 1,1-dimethyl 2-propenyl o-phenylenephosphate, 2-propenyl o-phenylenephosphate, 3-methyl-2-butenyl o-phenylenephosphate, 2-thienylmethyl o-phenylenephosphate, 2-furfurylmethyl o-phenylenephosphate, bis-o-phenylenepyrophosphate, 2-phenyl-1,3,2-benzodioxaphosphole-2-oxide, 2-(p-chlorophenyl)-1,3,2-benzodioxaphosphole-2-oxide, 2-butyl-1,3,2-benzodioxaphosphole-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2-benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-2-oxide, 4-chloro-2-methoxy-1,3,2-benzodioxaphosphole-2-oxide, 2-methoxy-4-methyl-1,3,2-benzodioxaphosphole-2-oxide, 2,3naphthalenemethylphosphate, 5,6-dimethyl-2-methoxy-1,3,2-benzodioxaphosphole-2-oxide, 2,2-dihydro-4,5,6,7-tetrachloro-2,2,2-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-2-benzyl-2,2-dimethoxy-1,3,2-benzodioxaphosphole, 2,2-dihydro-4,5-benzo-2,2,2-trimethoxy-1,3,2-benzodioxaphosphole, 2,2-dihydro-2,2,2-triphenoxy-1,3,2-benzodioxaphosphole, 2,2-dihydro-2,2-(o-phenylenedioxy)-2-phenoxy-1,3,2-benzodioxaphosphole, 2-chloro-2,2-dihydro-2,2-(o-phenylenedioxy)-1,3,2-benzodioxaphosphole, 2,2-dihydro-2-methoxy-2,2-(o-phenylenedioxy)-1,3,2-benzodioxaphosphole, 2,2-dihydro-2,2,2-trichloro-1,3,2-benzodioxaphosphole, 9,10-phenanthrenedioxytrimethoxyphosphorus, o-phenylenephosphochloridite, o-phenylenephosphorobromidite, o-phenylenephosphorofluoridite, methyl o-phenylenephosphite, butyl o-phenylenephosphite, methoxycarbonylmethyl o-phenylenephosphite, phenyl o-phenylenephosphite, p-chloro (or p-nitro)phenyl o-phenylenephosphite, 2-phenyl-1,3,2-benzodioxaphosphole, bis-o-phenylenepyrophosphite, 2-methoxy-5-methyl-1,3,2-benzodioxaphosphole, 5-acetyl-2-phenoxy-1,3,2-benzodioxaphosphole, 9,10-phenanthrenephosphorochloridite, 2-chloro-4-methyl-1,3,2-benzodioxaphosphole, 5-ethoxycarbonyl-2-phenyl-1,3,2-benzodioxaphosphole, 2-chloro-2-thioxo-1,3,2-benzodioxaphosphole, 2-phenoxy-2-oxo-1,3,2-benzodiazaphosphole, 2-phenoxy-1,3,2-benzodioxaazaphosphole, 2,2-dihydro-2-oxo-2-methoxy-4,5-dimethyl-1,3,2-dioxaphosphole, 2,2-dihydro-2-oxo-2-chloro-4,5-dimethyl-1,3,2-dioxaphosphole, 2,2-dihydro-2-oxo-2-(1-imidazolyl)-4,5-dimethyl-1,3,2-dioxaphosphole, 2,2-dihydro-2,2-ethylenedioxy-2-methoxy-4,5-dimethyl-1,3,2-dioxaphosphole, 2,2-dihydro-2,2-dimethoxy-2-phenoxy-4,5-dimethyl-1,3,2-dioxaphosphole, 2,2-dihydro-2,2,2-trimethoxy-4,5-dimethyl-1,3,2-dioxaphosphole, 2,2-dihydro-2,2,2-triphenoxy-4,5-dimethyl-1,3,2-dioxaphosphole, 2,2-dihydro-2,2,2-triethoxy-4,5-diphenyl-1,3,2-dioxaphosphole, 2,2-dihydro-2,2,2-trimethoxy-4,5-diphenyl-1,3,2-dioxaphosphole, 2,2-dihydro-2-oxo-2-methoxy-4,5-diphenyl-1,3,2-dioxaphosphole, 2,2-dihydro-2,2,2-trimethoxy-1,3,2-dioxaphosphole, 2,2-dihydro-2,2,2-trimethoxy-4-phenyl-1,3,2-dioxaphosphole, 2,2-dihydro-2,2,2-trimethoxy-4-methyl-1,3,2-dioxaphosphole, 2,2-dihydro-2,2,2-trimethoxy-4-methyl-5-phenylcarbamoyl-1,3,2-dioxaphosphole, 2,2,4,5,6,7-hexahydro-2,2,2-trimethoxy-1,3,2-benzodioxaphosphole, 2,2'-oxybis(4,5-dimethyl-2,2-dihydro-1,3,2-dioxaphosphole) and 2,2'-oxybis-(4,5-dimethyl-2,2-dihydro-1,3,2-dioxaphosphole-2-oxide.)

The reaction is usually carried out in a solvent which does not interfere with the reaction. Preferable examples of the solvent include the ethers, the esters, the halogenated hydrocarbons, the hydrocarbons, the amides, the ketones and the nitriles described above , which may be used alone or in a mixture thereof. Especially dichloromethane, acetonitrile, formamide, a mixture of formamide and acetonitrile, and a mixture of dichlormethane and acetonitrile bring about a good result. The amount of the thiol compound ASH or a salt thereof and the amount of the organic phosphorus compound are about 1 to 5 moles and about 1 to 10 moles, per 1 mole of the compound (X) or a salt or ester thereof, respectively, preferably 1 to 3 moles and 1 to 6 moles, respectively. The reaction is conducted at about −80° to 50° C., preferably at about −40° to 40° C. The reaction time is usually about 1 minute to 15 hours, preferably about 5 minutes to 2 hours. An organic base may be added to the reaction system. Examples of the organic base include amines, such as triethylamine, tri(n-butyl)amine, di(n-butyl)amine, diisobutylamine, dicyclohexylamine, diisobutylamine, dicyclohexylamine and 2,6-lutidine. The base is preferably used in an amount of about 1 to 5 moles per 1 mole of the compound (X) or a salt or ester thereof.

(3-2-3): When $R^5$ is a halogen:

Preferable solvents are the ethers, esters, halogenated hydrocarbons, hydrocarbons, amides, ketones, nitriles, alchohols and water described above. The thiol compound ASH or a salt thereof is usually used in an amount of about 1 to 5 moles, preferably about 1 to 3 moles per 1 mole of the compound (X) or a salt or ester thereof. The reaction is conducted at about 0° to 80° C., preferably at about 20° to 60° C. The reaction time is usually about 30 minutes to 15 hours, preferably about 1 to 5 hours. The reaction can be conducted in the presence of an acid binding agent to accelerate the reaction. As the acid binding agent use is made of the acid binding agents described in the Method of Production (3-1), such as inorganic bases, tertiary amines or alkylene oxides. The halogen represented by $R^5$ is chlorine, bromine or iodine, among which iodine is preferable. The compound (X) in which $R^5$ is iodine can be produced easily, for example, by the method described in Japanese Laid-Open Patent Application No. 57390/83 or by a method analogous thereto. By the method described above, for example, the compound (VII) or (VIII) described above can be synthesized. The reaction is written by the following formulas.

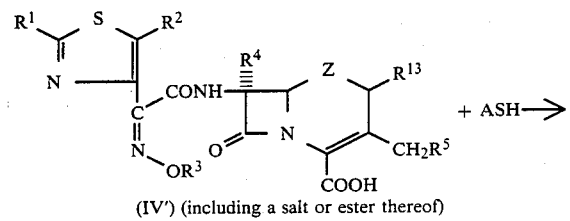
(IV') (including a salt or ester thereof)

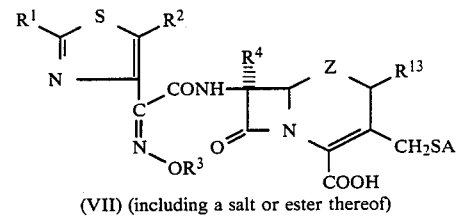
(VII) (including a salt or ester thereof)

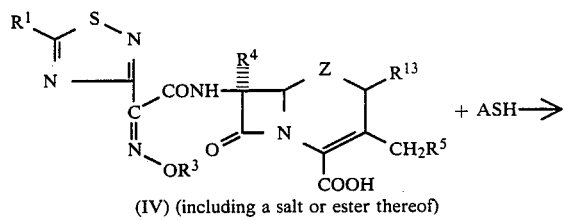
(IV) (including a salt or ester thereof)

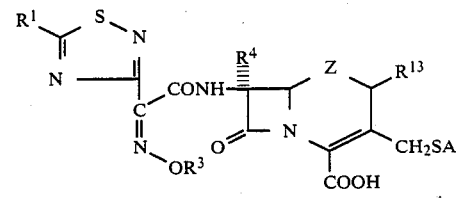

-continued
(VIII) (including a salt or ester thereof)

The compound (IV') and the compound (IV) can be easily produced with a known method or one analogous thereto. The compound (XI) described below including the compound (VII) and (VIII) can be produced not only by the Method of Production (3-1) and (3-2), but also by the Method (3-3) described below. The compound (VII) can be also produced by Method of Production (3-4) described below, in addition to the Methods (3-1), (3-2) and (3-3)

(3-3): The reaction is written by the following formula.

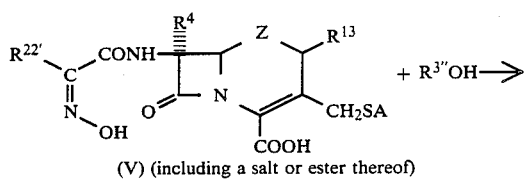

(V) (including a salt or ester thereof)

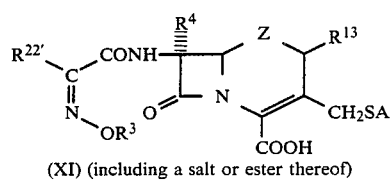

(XI) (including a salt or ester thereof)

wherein the symbol $R^{22'}$ is a heterocyclic group which may be substituted, and other symbols are of the same meaning as defined above.

This method consists in synthesis of the compound (XI) reacting a hydroxymino compound (V) with a compound of the general formla $R^{3''}OH$ or a reactive derivative thereof, which is a conventional ether-formation reaction. When $R^{22'}$ is a group of the formula:

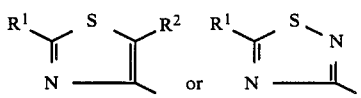

the product (XI) is the compound (VII) or (VIII), respectively. $R^{3''}$ is a hydrocarbon residue which may be substituted. The hydrocabon residues which may be substituted as described before as $R^3$, are also here applicable. The compound $R^{3''}OH$ may be used in a free form or as a reactive derivative thereof. The reactive derivative of the compound $R^{3''}OH$ means the derivative of $R^{3''}OH$ having a group which is removed together with the hydrogen atom of hydroxymino compound (V), that is, a compound of the general formula $R^{3''}Y$. The group Y which is removed together with the hydrogen atom is halogen, sulfo or a mono-substituted sulfonyloxy group. The halogen is chlorine, bromine or iodine. Examples of the mono-substituted sulfonyloxy group include $C_{1-6}$ alkylsulfonyloxy group and $C_{6-10}$ arylsulfonyloxy group, such as methanesulfonyloxy, ethanesulfonyloxy, benzenesulfonyloxy or p-toluenesulfonyloxy. Especially when $C_{1-4}$ alkyl ether derivatives of the compound (V) are produced, not only the reactive derivative described above, but also $C_{1-4}$ diazoalkane, such as diazomethane and diazoethane, and di-$C_{1-4}$ alkyl sulfate, such as dimethyl sulfate and diethyl sulfate may be used.

The compound (V) can be synthesized by the acylation described in the Method of Production (3-1) or by the nuclephilic substitution described in the Method of Production (3-2). That is, the reactions are shown by the following reaction formulas, respectively.

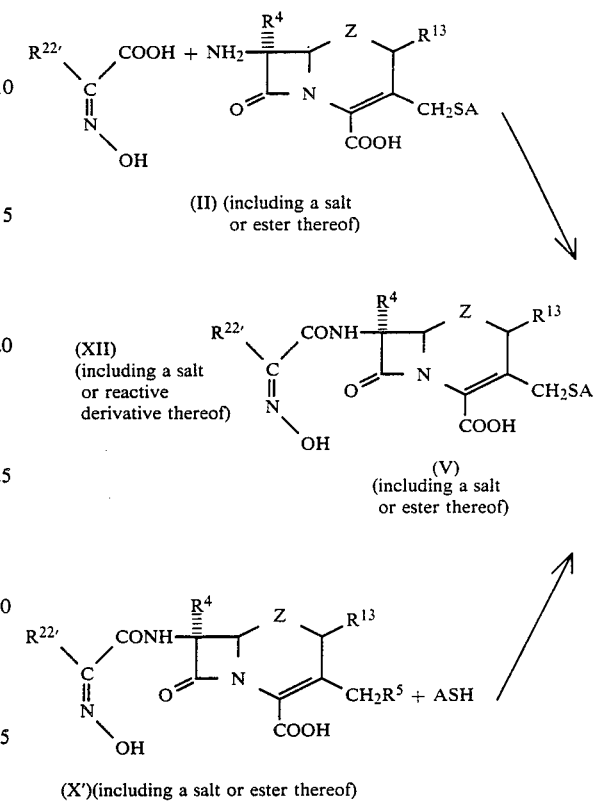

The starting compoudns (XII) and (X') can be synthesized also easily by a known method or one analogous thereto. Also the compound $R^{3''}OH$ or a reactive derivatives thereof can be easily synthesized by a known method or one analogous thereto.

(3-3-1): When $R^{3''}OH$ is used:

The compound (XI) is synthesized by reacting the hydroxymino compound (VI) with a compound $R^{3''}OH$ in the presence of an appropriate dehydrating agent. Examples of the dehydrating agent include phosphorus oxychloride, thionyl chloride, dialkyl azodicarbonate (usually used in the presence of phosphine) and N,N-dicyclolohexylcarbodiimide, preferably diethyl azodicarbonate in the presence of triphenylphosphine. The reaction using diethyl azodicarbonate in the presence of triphenylphosphine is usually carried out in an anhydrous solvent such as ethers or hydrocarbons described above. About 1 to 1.5 moles each of the compound $R^{3''}OH$, ethyl azodicarbonate and triphenylphosphine are used per 1 mole of the hydroxyimino compound (V). The reaction takes about 1 to 4 days at about 0° to 50° C.

(3-3-2): When $R^{3''}Y$ is used:

The reaction of the compound $R^{3''}Y$ with the hydroxyimino compound (V) is a usual ether-formation reaction, which is carried out in a solvent. The solvents are the ethers, esters, halogenated hydrocarbons, hydrocarbons, amides, ketones, nitriles, alchohols and water as described in the Method of Production (3-1), which are used alone or in a mixture thereof, preferably a mixed solvent consisting of a solvent miscible with water and water (e.g., aqueous methanol, aqueous ethanol, aqueous acetone or aqueous dimethylsulfoxide). This reaction may be carried out smoothly in the presence of an appropriate base. Examples of the base include inorganic bases, such as alkalimetal salts exemplified by sodium carbonate, sodium hydrogen carbonate or potassium carbonate and alkalimetal hydroxides exemplified by sodium hydroxide or potassium hydroxide. This reaction may be conducted in a buffer solution of pH 7.5 to 8.5. The reagent $R^{3\prime\prime}Y$ is used in an amount of about 1 to 5 moles, preferably about 1 to 3 moles, per 1 mole of the starting compound (V) and the base is used in an amount of about 1 to 10 moles, preferably about 1 to 5 moles, per 1 mole of the starting compound (V). The reaction temperature is about $-30°$ to $100°$ C., preferably about $0°$ to $80°$ C. The reaction time is about 10 minutes to 15 hours, preferably about 30 minutes to 5 hours.

(3-3-3): When $C_{1-4}$ diazoalkane is used:

The reaction is usually conducted in a solvent. As the solvent, the ethers and hydrocarbons described above are used. The reaction proceeds when a solution of a diazoalkane compound is added to the solution of the hydroxyimino compound (V). About 1 to 10 moles, preferably about 1 to 5 moles of the reagent is used per 1 mole of the compound (V). The reaction is carried out at a relatively low temperature, i.e., at about $-50°$ to $20°$ C., preferably at about $-30°$ to $0°$ C. The reaction time is about 1 minute to 5 hours, preferably about 10 minutes to 1 hour.

(3-3-4): When di-$C_{1-4}$ alkyl sulfate is used:

The reaction is usually conducted in water or in a mixed solvent consisting of a solvent miscible with water and water. Examples of the mixed solvent are also here the aqueous solvents described in the Method of Production (3-3-2). This reaction is usually conducted in the presence of an inorganic base, such as alkalimetal hydroxides exemplified by sodium hydroxide or potassium hydroxide. Per one mole of the compound (V), about 0.5 to 10 moles, preferably about 1 to 2 moles of the reagent are used. The reaction temperature is about $20°$ to $100°$ C., preferably about $50°$ to $100°$ C. The reaction time is about 10 minutes to 5 hours, preferably about 30 minutes to 3 hours.

(3-4): The reaction is written by the following formula:

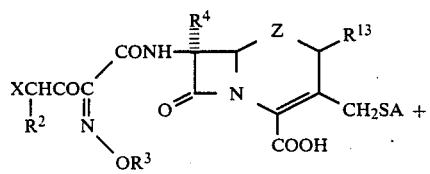

(VI)(including a salt or ester thereof)

$R^1C(=S)NH_2 \longrightarrow$

-continued

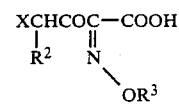

(VII)(including a salt or ester thereof)

wherein X is a halogen; and other symbols are of the same meaning as defined above.

This is a process for preparing the desired compound (VII) by reacting the compound (VI) with thiourea or a thiourea derivative of the general formula $R^1C(=S)NH_2$. The compound (VI) may be used in a free form or in the form of a salt or ester thereof. In the compound (VI), X is a halogen, such as chlorine, bromine or iodine. Examples of the salt of the compound (VI) are the salt of the 7-amino compound (II) described in the Method of Production (3-1) (for example, inorganic base salts, ammonium salts, organic base slats, inorganic acid addition salts or organic acid addition salts). Examples of the ester of the compound (VI) are the ester of the 7-amino compound (II) described in the Method of Production (3-1) (for example, the $C_{1-6}$ alkyl*, $C_{2-6}$ alkenyl, $C_{3-10}$ cycloalkyl, $C_{3-6}$ cycloalkyl$C_{1-6}$alkyl, $C_{6-10}$ aryl*, $C_{7-12}$ aralkyl*, di-$C_{6-10}$ aryl-methyl, tri-$C_{6-10}$ aryl-methyl and $C_{2-6}$ alkanoyloxy $C_{1-6}$ alkyl esters. The starting compound (VI) can be easily synthesized by reacting a compound of the general formula:

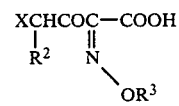

wherein the symbols are of the same meaning as defined above, or a salt or reactive derivative thereof, with the 7-amino compound (II) or a salt or ester thereof described above, according to the method described in the Method of Production (3-1). The compound of the general formula:

$$\underset{R^2}{\text{XCHCOC}}-\underset{\substack{N \\ \diagdown \\ OR^3}}{\overset{\text{O}}{\parallel}}\text{COOH}$$

or a reactive derivative thereof can be easily prepared by a per se known method or by one analogous thereto. The reaction of the compound (VI) with the compound $R^1C(S=)NH_2$ is usually carried out in a solvent. As the solvent, ethers, such as dioxane, tetrahydrofuran or diethylether, alcohols, such as methanol, ethanol or n-propanol, and amides, such as dimethylformamide or dimethylacetamide are used. The amount of thiourea or a derivative thereof $R^1C(S=)NH_2$ is usually about 1 to 5 moles, preferably about 1 to 3 moles, per 1 mole of the compound (VI). The reaction may be conducted at about $0°$ to $100°$ C., preferably about $20°$ to $60°$ C. The reaction time is usually about 30 minutes to 15 hours, preferably about 1 to 5 hours.

When a hydroxyimino group (or a substituted hydroxyimino group) is present in the substituent $R^b$ of the compound ($I^b$) produced by the Methods of Production (3-1) to (3-4) (for example, the compound (VII) and the compound (VIII)), the compound ($I^b$) is sometimes obtained as a mixture of the syn(Z)- and anti(E)-isomers. The desired syn-isomer may be isolated from the mixture by a per se known method or one analogous thereto, such as fractionation by taking advantage of the difference of solubility or crystalinity, chromatographic separation and separation by taking advantage of the difference of rate of hydrolysis of the ester derivatives.

Method of Production (4): Synthesis of the compound (I) ($R^0 = R^c$; $R^c$ is an amino-protective group)

For example, the compound can be synthesized by reacting the 7-amino compuodn (II) ((I), $R^0 =$ hydrogen) or a salt or ester thereof synthesized in the Method of Production (1), with an amino-protective reagent. In the following some examples are shown.

(4-1): When $R^c$ is phthaloyl:

As the phthaloylating reagent, phthalic anhydride or a phthaloyl halide (e.g., phthaloyl chloride) is used. The reaction is generally conducted in a solvent.

An anhydrous solvent is more preferable when phthaloyl halide is used. Examples of the solvent include ethers, such as dioxane, tetrahydrofuran, diethyl ether, tertbutyl methyl ether, diisopropyl ether or ethylene glycol dimethyl ether, halogenated hydrocarbons, such as dichloroethane, chloroform, carbon tetrachloride, trichlene or 1,2-dichloroethane and hydrocarbons, such as n-hexane, benzene or toluene. These solvents are used alone or in a mixture thereof. The amount of reagent used is usually about 1 to 3 moles, preferably about 1 to 1.5 moles per 1 mole of the 7-amino compound (II). The reaction may be carried out at about −80° to 150° C., but when phthalic anhydride is used, the reaction temperature is about 30° to 150° C., preferable about 70° to 140° C., and when phthaloyl halide is used, the reaction temperature is about −80° to 100° C., preferably about -30 to 80° C. The reaction time varies depending on the species of the 7-amino compound (II) and the phthaloylating reagent, the kind of the solvent, the reaction temperature etc., being usually about 1 minute to 24 hours, preferably about 10 minute to 4 hours.

When phthalic anhydride is used, the reaction may sometimes proceed more effectively by removing water formed in the reaction out of the reaction system. When a phthaloyl halide is used, the reaction may be conducted in the presence of an acid binding agent to remove the liberated hydrogen halide out of the reaction system. Examples of the acid binding agent include inorganic bases, such as sodium carbonate, potassium carbonate, calcium carbonate or sodium hydrogen carbonate, tertiary amines, such as triethylamine, tri(n-propyl)amine, tri(n-butyl)amine, diisopropylethylamine, cyclohexylmethylamine, pyridine, lutidine, γ-collidine, N,N-dimethylaniline, N-methylpiperidine, N-methylpyrrolidine or N-methylmorpholine, and alkylene oxides, such as propylene oxide or epichlorohydrine.

(4-2): When $R_c$ is a substitutd oxycarbonyl group:

As the substituted oxycarbonylating agent, for example, substituted oxycarbonyl halides (in which halogen is chlorine, bromine or iodine etc.), substituted oxycarbonyl azides, substituted oxycarbonic anhydrides, substituted oxycarbonyl sulfides, and substituted oxycarobnyl azolides (in which azoles are imidazole, N-methylimidazole, triazole, 2-thiooxazolidine, 2-oxooxazolidine) are used. The reaction is generally carried out in a solvent, and an anhydrous solvent is preferable. Examples of the solvent include ethers, such as dioxane, tertrahydrofuran, diethyl ether, tert-butyl methyl ether, diisopropyl ether and ethylene glycol-dimethyl ether, halogenated hydrocarbons, such as dichloroethane, chloroform, carbon tetrachloride, trichlene or 1,2-dichloroethane, nitriles, such as acetonitrile, alcohols, such as methanol, ethanol, propanol and butanol, hydrocarbons, such as n-hexane, benzene or toluene, amides, such as dimethylformamide, dimethylacetamide or hexamethylphosphorus triamide and sulfoxides, such as dimethylsulfoxide. These solvents are used alone or in a mixture thereof. The amount of the substituted oxycarbonylating agent is usually about 1 to 5 moles, preferably about 1 to 2 moles, per 1 mole of the 7-amino compound (II). The reaction is conducted at about −80° to 80° C., preferably at about −40° to 50° C., and most desirably at about −30° to 30° C. The reaction time varies depending on the species of the 7-amino compound (II) and the substituted oxycarbonylating agent, the kind of the solvent, the reaction temperature, etc., being usually about 1 minute to 48 hours, preferably about 10 minutes to 2 hours. When a substituted oxycarbonyl halide is used as the substituted oxycarbonylating agent, the reaction may be conducted in the presence of an acid binding agent to remove the liberated hydrogen halide out of the reaction system. Examples of the acid binding agent include inorganic bases, such as sodium carbonate, potassium carbonate, calcium carbonate or sodium hydrogen carbonate, tertiary amines, such as triethylamine, tri(n-propyl)amine, tri(n-butyl)amine, diisopropylehtylamines, cyclohexyldimethylamine, pyridine, lutidine, γ-collidine, N,N-dimethylaniline, N-methylpiperidine, N-methylpyrrolidine or N-methylmorpholine and alkylene oxides, such as propylene oxide or epichlorohydrine.

(4-3): When $R^c$ is a $C_{6-10}$ aryl*methyl, di-$C_{6-10}$ aryl*methyl, or tri-$C_{6-10}$ aryl*methyl group:

As the reagents, the corresponding halides, i.e., $C_{6-10}$ aryl*methyl halides, di-$C_{6-10}$ aryl*methyl halides, and tri-$C_{6-10}$ aryl methyl*halides are used. Among those halides, iodides, bromides and chlorides are preferable. As the solvent, use is made of those described in the Method of Production (4-2). The amount of the reagent is usually about 1 to 3 moles, preferably about 1 to 1.5 moles, per 1 mole of the 7-amino compound (II). The reaction is conducted at about −80° to 100° C., preferably at about −30° to 70° C. The reaction time varies depending on the species of the 7-amino compound (II) and the substituted-oxycarbonylating agent, the kind of the solvent, the reaction temperature, etc., being usually about 1 minute to 24 hours, preferably about 10 minutes to 5 hours. This reaction may be conducted in the presence of an acid-binding agent to remove the hydrogen halide formed out of the reaction system. As the acid binding agent use is made of those described in the Method of Production (4-1).

After the reaction described in the Methods of Production (1)–(4), the desired compuond (I) of this invention can be obtained by removal of the protective group and purification, if necessary. In the following the method of removal of the protective group and the purification are explained.

Method of Removal of the Protective Group: As described above, amino-protective groups have been extensively investigated and the methods of protection have been established in the fields of synthesis of β-lactams and peptides. Also the methods of removal of amino-protective groups have been established, and the known procedures of removal of the protective groups are applicable also to the present invention. For example, a monohalogenoacetyl group (such as chloracetyl or bromoacetyl) can be removed with thiourea, an alkoxycarbonyl group (such as methoxycarbonyl, ethoxycarbonyl or tert-butoxycarbonyl) with an acid (such as hydrochloric acid), an aralkyloxycarbonyl group (such as benzyloxycarbonyl, p-methylbenzyloxycarbonyl, or pnitrobenzyloxycarbonyl) by catalytic reduction, and the 2,2,2-trichloroethoxycarbonyl group with zinc and an acid (such as acetic acid). When the compound (I) is esterified, the ester residue can be also removed by a per se known procedure or one analogous thereto. For example, the 2-methyl-sulfonyl ethyl ester group can be removed with an alkali, the aralkyl ester group (such as a benzyl, p-methoxybenzyl, or p-nitrobenzyl ester) with an acid (such as trifluoroacetic acid) or by catalytic reduction, the 2,2,2-trichloroethyl ester group with zinc and an acid (such as acetic acid), and the silyl ester group (such as a tri-methylsilyl, or tert-butyl dimethylsilyl ester) with water alone.

Purification of the Compound (I): Method of the compound (I) produced in the reaction mixture by the methods described in detail in the Methods of Production (1) to (4), followed by, if necessary, the removal of the protective group according to the method described above, can be isolated and purified by a known procedure, such as extraction, column chromatography, precipitation or/and recrystallization. When thus isolated compound (I) is not a salt or ester, the product can be converted into a desired pharmaceutically aceptable salt or a metabolically unstable, non-toxic ester by known procedure or one analogous thereto.

The sulfoxide ((I), $Z=S \rightarrow O$) of cephem compounds ((I), $Z=S$) is obtained by oxidation of the compound ((I), $Z=S$). Such oxidation is conventional. Oxidizing agents suitable for the oxidation of the sulfur atom in the cephem ring include oxygen, peracids, hydroperoxides and hydrogen peroxide, and the peracids can be easily produced by mixing an acid with a peroxide during the reaction. As the peracids, peracetic acid, perbenzoic acid and p-chloroperbenzoic acid are frequently used. The reaction is usually conducted in a solvent. Examples of the solvent used for this reaction include ethers, such as dioxane or tetrahydrofuran, halogenated hydrocarbons, such as dichloromethane, chloroform or chlorobenzene, organic acids, such as formic acid, acetic acid or trifluoroacetic acid, and amides, such as dimethylformamide or dimethylacetamide. The reaction is conducted at about $-20°$ to $80°$ C., preferably at a temperature as low as possible, desirably about $-20°$ to $30°$ C. It is generally known that a sulfoxide of S-configuration is predominantly produced by oxidation of a cephem compound ((I), $Z=S$). R- and S-sulfoxides are fractionated by taking advantage of the difference in their solubility or mobility in chro matographic separation. The oxidation reactions to produce the sulfoxides described above may be conducted prior to or subsequently to the reactions described in the Methods of Production (1) to (4).

The compound (I) of this invention including the compounds (VII) and (VIII) or a pharmaceutically acceptable salt or metabolically unstable, nontoxic ester thereof is able to be administered parenterally or orally in the form of injections, capsules, tablets, and granules, as the known penicillins and cephalosporins. The dose is 0.5 to 80 mg/day/kg body weight of a man or an animal infected with a pathogenic bacteria described above, preferably 1 to 20 mg/day/kg, given 3 or 4 times a day. The excipients used for injections include distilled water and pysiological saline. For capsules, powders, granules and tablets, a known pharmaceutically aceptable excipient (e.g., starch, lactose, sucrose, calcium carbonate or calcium phosphate), a binder (e.g., starch, gum arabic, carboxymethylcellulose, hydroxypropylcellulose or crystalline cellulose), a lubricant (e.g., magnesium stearate or talc) and a disintegrating agent (e.g., carboxymethylcellulose calcium or talc) are used.

Pharmaceutical compositions containing the compound (I) or a pharmaceutically acceptable salt or metabolically unstable, nontoxic ester thereof can be produced by a per se known method. The said compositions can be produced usually by mixing at least one of the compounds (I), or pharmaceutically acceptable salts or metabolically unstable, nontoxic esters thereof with the carriers, excipients etc. described above. The ratio of the compound (I) contained in a composition is usually about 5 to 100%, preferably about 20 to 100% by weight in solid compositions, such as capsules, tablets or granules, and 5 to 30% by weight in liquid compositions, such as injections.

The compound (I) or a pharmaceutically acceptable salt or metabolically unstable, nontoxic ester thereof is given in the form of injection for treatment of urinary tract infection caused by Escherichia coli. The dose in this case is 0.5 to 80 mg/day/kg body weight of a man or an animal, preferably 1 to 20 mg/day/kg, given 3 or 4 times a day. Such injections can be produced easily, for example, by dissolving or suspending the compound (I) or a salt or ester thereof in physiological saline.

This invention is illustrated in further detail in the Reference Examples and Working Examples, which are only examples, and do not limit this inveniton. Modification within the scope of this invention are permissible.

Elution in a colum chromatography in the Reference Examples and Working Examples was conducted while monitoring with TLC (Thin Layer Chromatography). In the TLC monitoring, the TLC plate used was BOF254 manufactured by Merck Co., West Germany, and the developing solvent was the same to the one used for eluting in the column chromatography, and the detection was conducted with a UV detector. The silica gel for the column was Kieselgel 60 (230–400 mesh) manufactured by Merck Co., West Germany. "Sephadex" is a product of Pharmacia Fine Chemicals Co., Sweden. XAD-II resin is a product of Rohm & Haas Co., U.S.A. NMR spectra were measured using tetramethylsilane as in internal or external standard with a spectrometer XL-100A (10 MHz), EM360 (60 MHz), EM 390 (90 MHz) or $T_{60}$ (60 MHz) type, and all $\delta$ values are expressed in ppm. The value shown in ( ) for a mixed solvent is a mixnig ratio in volume of constituent solvents The percentage (%) for a solution indicates the grams in 100 ml of the solution. The symbols in Reference Examples and Examples mean as follows.

s: singlet
d: doublet
t: triplet
q: quartet
ABq: AB type qurtet
d.d: double doublet
m: multiplet
br.: broad
J: coupling constant
Hz: Herz DMSO: dimethyl sulfoxide

REFERENCE EXAMPLE 1

5-Mercaptoimidazol[1,2-a]pyridine

A mixture of 2.5 g of 5-chloroimidazo[1,2-a]pyridine and 30 ml of 2N-potassium hydrogen sulfide solution is stirred at room temperature for 6 hours and then at 80° C. for 3 days. The pH of the reaction mixture is adjusted to 2 with concentrated hydrochloric acid. The reaction mixture is extracted twice with 200 ml of ethyl acetate, and dried over magnesium sulfate, followed by evaporation of the solvent under reduced pressure, and the resulting powder is collected by filtration. Yield:33%.

Elemental analysis for $C_7H_6N_2S \cdot H_2O$; Calcd. (%): C, 49.98; H, 4.79; N, 16.65; Found (%): C, 50.14; H, 4.51; N, 16.72;

IR spectrum$\nu_{max}^{KBr}$ cm$^{-1}$:1625, 1480, 1360, 1350, 1200, 960, 820, 765, 740.

NMR spectrum (DMSO-$d_6$)δ: 6.8–7.5(3H,m), 7.86 and 8.35 (2H, each d, J-2 Hz).

REFERENCE EXAMPLE 2

5-Mercapto-7-methylimidazo[1,2-a]pyrimidine

In a similar way to Reference Example 1, using 5-chloro-7-methylimidazo[1,2-a]pyrimidine and potassium hydrogen sulfide, the title compound is obtained. mp. 230–237(dec.).

EXAMPLE 1

Sodium 7β-[2-(2-aminothiazol-4-yl)-2(Z)-methoxyiminoacetamido]-3-[(imidazo[1,2-a]pyridin-5-yl)thiomethyl]-3-cephem-4-carboxylate.

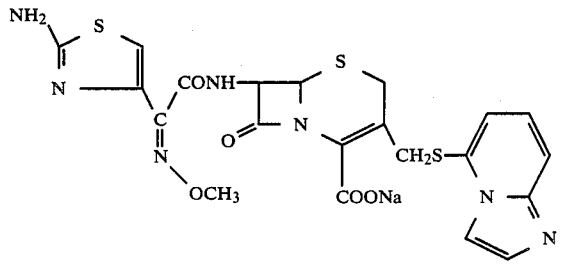

A mixture of 1.0 g of 7β- [2-(2-aminothiazol-4-yl)-2-(z)methoxyiminoacetiamido]-3-(3-oxobutyryloxy)methyl-3-cephem-4-carboxylic acid, 1.0 g of sodium iodide, 336 mg of 5-mercaptoimidazo[1,2-a]pyridine and a mixed solvent consisting of 10 ml of water and 4 ml of acetonitrile is stirred at 70° C. for 20 minutes.

The reaction mixture is cobled to room temperature, and to it is added 500 mg of sodium hydrogen carbonate. Most of the organic solvent is evaporated off. The residue is subjected to column chromatography on Diaion CHP20P (manufactured by Mitsubishi Chemical Industries Limited, Japan, high porous polymer, 150–300μ), and eluted with successive water, 10% aqueous acetonitrile solution, and 20% aqueous acetonitrile solution.

The fractions containing the object compound are collected, concentrated and lyophilized to give the title compound. Yield:40%.

Elemetal Analysis for $C_{21}H_{18}N_7O_5S_3Na \cdot 4.5H_2O$: Calcd. (%): C,38.88; H,4.20; N,15.11; Found (%): C,39.02; H,3.98; N,15.33.

IR spectrum $\nu_{max}^{KBr}$ cm$^{-1}$: 1760, 1665, 1600, 1530, 1485, 1380, 1355, 1290, 1200.

NMR spectrum ($D_2O$)δ: 3.30 and 3.69 (2H, ABq, J=18 Hz), 4.01(3H,s), 3.73 and 4.80(2H, ABq, J=14 Hz), 5.03(1H, d, J=5 Hz), 5.64(1H, d, J=5 Hz), 6.96(1H, s), 7.00–7.60 (3H,m), 7.64(1H,br.s), 7.97(1H,br.s.).

EXAMPLE 2

Sodium 7β-[2-(2-aminothiazol-4-yl)-2(Z)-ethoxyiminoacetamido]-3-[(imidazo[1,2-a]pyridin-5-yl)thiomethyl]-3-cephem-4-carboxylate

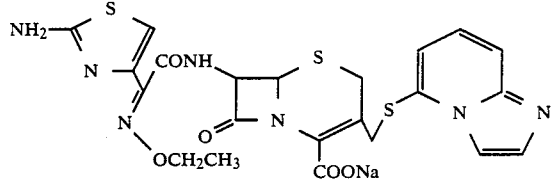

In a similar way to Example 1, using 7β-[2-(2-aminothiazol-4-yl)-2(Z)-ethoxyiminoacetamido]-3-(3-oxobutyryloxy)methyl-3-cephem-4-carboxylic acid and 5-mercaptoimidazo[1,2-a]pyridine, compound is obtained.

Elemental analysis for $C_{22}H_{20}N_7H_5S_3Na \cdot 4H_2O$: Calcd.(%): C,40.42; H,4.32; N,15.00; Found (%): C,40.70; H,4.37; N,14.71.

IR$\nu_{max}^{KBr}$cm$^{-1}$: 1760, 1660, 1610, 1525.

NMR($d_6$-DMSO)δ: 1.23(3H,t,J=7 Hz), 4.10(2H,q,J=7 Hz), 4.27 & 4.42(2H,ABq,J=12 Hz), 5.01(1H,d,J=5 Hz), 5.60 (1H,d.d,J=5 Hz & J=8 Hz), 6.70(1H,s), 6.9–7.3 (4H,m), 7.36–7.6(1H,m), 7.64(1H,s), 7.96(1H, s), 9.40(1H,d,J=8 Hz).

EXAMPLE 3

Sodium 7β-[2-(2-aminothiazol-4-yl)-2(Z)-propargyloxyiminoacetamido]-3-[(imidazo[1,2-a]pyridin-5-yl)thiomethyl]3-cephem-4-carboxylate

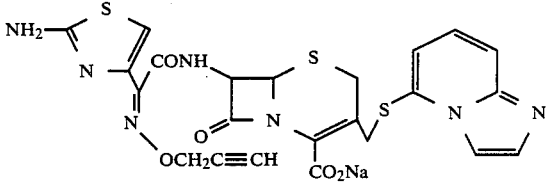

In a similar way to Example 1, using 7β-[2-(2-aminothiazol-4-yl)-2(Z)-propargyloxyiminoacetamido]-3-(3-oxobutyryloxy)methyl-3-cephem-4-carboxylic acid and 5-mercaptoimidazo[1,2-a]pyridine, the title compound is obtained.

Elemental analysis for $C_{23}H_{18}N_7O_5S_3Na \cdot 4H_2O$: Calcd.(%): C,41.62; H, 3.95; N, 14.49; Found (%): C,42.03; H, 3.86; N, 14.08.

IR$\nu_{max}^{KBr}$cm$^{-1}$: 1760, 1660, 1605, 1525.

NMR($d_6$-DMSO)δ: 4.38(2H,br,s), 3.68(2H,d,J=2 Hz), 4.98(1H,d, J=4.5 Hz), 5.56(1H,d.d, J=4.5 Hz & J=8 Hz), 6.76(1H,s), 7.0–7.35(4H,m), 7.4–7.58(1H,m), 7.64(1H,s), 7.94(1H,s), 9.49(1H,d,J=8 Hz).

EXAMPLE 4

Sodium 7β-[2-(2-aminothiazol-4-yl)-2(Z)-2-methoxyethoxy-iminoacetamido]-3-[(imidazo[1,2-a]pyridin-5-yl)thiomethyl]-3-cephem-4-carboxylate

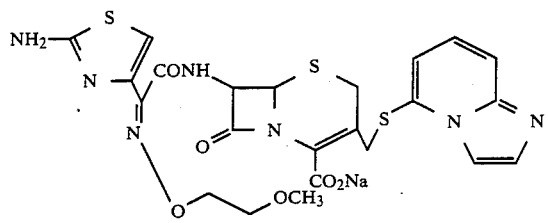

In a similar way to Example 1, using 7β-[2-(2-aminothiazol-4-yl)-2(Z)-2-methoxyethoxyiminoacetamido]-3-(3-oxobutyryloxy)methyl-3-cephem-4-carboxylic acid and 5-mercaptoimidazo[1,2-a]pyridine, the title compound is obtained.

Elemental analysis for $C_{23}H_{22}N_7O_6S_3Na.3.5H_2O$: Calcd.(%): C,40.94; H,4.33; N,14.53; Found (%): C,40.74; H, 4.14; N, 13.81.

IR$\nu_{max}^{KBr}$cm$^{-1}$: 1760, 1560, 1610, 1520.

NMR(d$_6$-DMSO)δ: 3.30(3H,s), 3.58(2H,t,J=6 Hz), 4.17(2H,t,6 Hz), 4.40(2H,br,s), 4.98(1H,d,J=5 Hz), 5.58(1H,d.d, J=5 Hz & 8 Hz), 6.73(1H,s), 6.9–7.28(4H,m), 7.35–7.6(1H,m), 7.64(1H,br-s), 7.94(S,1H), 9.40(1H,d,J=8 Hz).

EXAMPLE 5

Sodium 7β-[2-(2-aminothiazol-4-yl)-2(Z)-2-hydroxyethoxyiminoacetamido]-3-[(imidazo[1,2-a]pyridin-5-yl)thiomethyl]-3-cephem-4-carboxylate

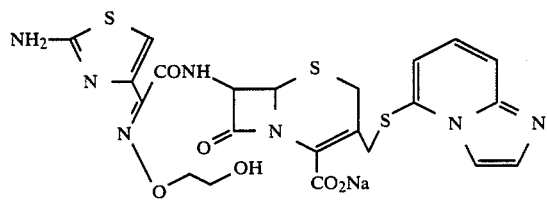

In a similar way to Example 1, using 7β-[2-(2-aminothiazol-4-yl)-2(Z)-2-hydroxyethoxyiminoacetamido]-3-(3-oxobutyryloxy) methyl-3-cephem-4-carboxylic acid and 5-mercaptoimidazo[1,2-a]pyridine, the title compound is obtained.

Elemental analysis for $C_{22}H_{20}N_7O_6S_3Na.2H_2O$: Calcd.(%): C,41.56; H, 4.12; N, 15.42; Found (%): C,41.64; H, 4.16; N, 15.33.

IR$\nu_{max}^{KBr}$cm$^{-1}$: 1760, 1660, 1600, 1530.

NMR(d$_6$-DMSO)δ: 3.54(2H×½, a half of ABq, J=18 Hz), 3.50 (2H,t,J=6 Hz), 4.09(2H,t,J=6 Hz), 4.24 & 4.40 (2H,ABq,J=12 Hz), 5.04(1H,d,J=5 Hz), 5.64(1H,d.d, J=8 Hz & 5 Hz), 6.74(1H,s), 7.0–7.35(4H,m), 7.4–7.7(2H,m), 7.97(1H,s), 9.40(1H,d,J=8 Hz)

EXAMPLE 6

Sodium 7β-[2-(2-aminothiazol-4-yl)-2(Z)-2-dimethylaminoethoxyiminoacetamido]-3-[(imidazo[1,2-a]pyridin-5-yl)thiomethyl-3-cephem-4-carboxylate

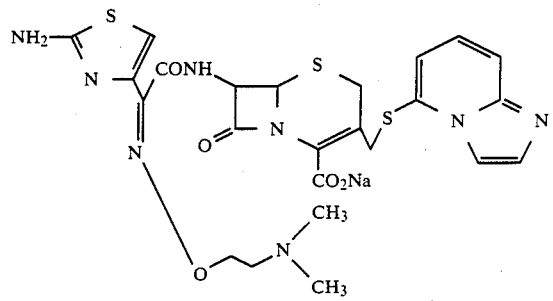

In a similar way to Example 1, using 7β-[2-(2-aminothiazol-4-yl)-2(Z)-methoxyiminoacetamido]-3-(3-oxobutyryloxy)methyl-3-cephem-4-carboxylic acid and 5-mercaptoimidazo[1,2-a]pyridine, the title compound is obtained.

Elemental analysis for $C_{24}H_{21}N_8O_5S_3Na.4H_2O$: Calcd.(%): C, 41.37; H, 4.77; N, 16.08; Found(%): C, 41.27; H, 4.13; N, 15.79.

IR$\nu_{max}^{KBr}$cm$^{-1}$: 1775, 1660, 1600, 1530.

NMR(d$_6$-DMSO)δ: 2.13(6H,s), 4.15(2H,t,J=6 Hz), 4.15 & 4.43 (2H,ABq,J=13 Hz), 4.99(1H,d,J=4 Hz), 5.32 (2H,t,J=6 Hz), 5.65(1H,d.d,J=4.5 Hz & 8 Hz), 6.67(1H,s), 6.95–7.3(4H,m), 7.4–7.6(1H,m), 7.63(1H,s), 7.98(1H,s), 9.45(1H,d,J=8 Hz).

EXAMPLE 7

Sodium 7β-[2-(2-aminothiazol-4-yl)-2(Z)-methoxyiminoacetamido]-3-[(imidazo[1,2-a]pyrazin-5-yl)thiomethyl]-3-cephem-4-carboxylate

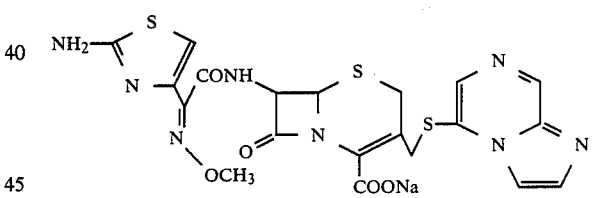

In a similar way to Example 1, using 7β-[2-(2-aminothiazol-4-yl)-2(Z)-methoxyiminoacetamido]-3-(3-oxobutyryloky) methyl-3-cephem-4-carboxylic acid and 5-mercaptoimidazo[1,2-a]pyrazine, the title compound is obtained.

Elemental analysis for $C_{20}H_{17}N_8O_5S_3Na.7/5H_2O$ Calcd.(%): C, 38.03; H, 3.83; N, 17.74; Found (%): C, 38.25; H, 3.75; N, 17.72.

IR$\nu_{max}^{KBr}$cm$^{-1}$: 1760, 1670, 1600, 1520.

NMR(d$_6$-DMSO)δ: 3.53(2H×½, a half of ABq,J=16.5 Hz), 3.84 (3H,s), 4.31(2H,br,s), 4.94(1H,d,J=4.5 Hz), 5.37–5.74(m,1H), 6.70(1H,s), 7.14(2H,br-s), 7.87(1H,s), 8.07(1H,s), 8.23(1H,s), 8.96 (1H,s), 9.48(1H,d,J=9 Hz).

EXAMPLE 8

Sodium 7β-[2-(2-aminothiazol-4-yl)-2(Z)-methoxyiminoacetamido]-3-[(7-methylimidazo[1,2-a]pyrimidin-7-yl)thiomethyl]-3-cephem-4-carboxylate

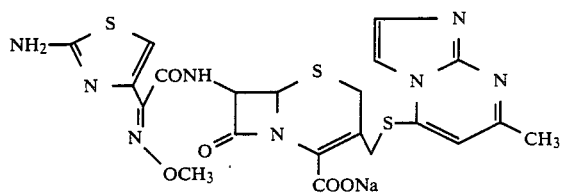

In a similar way to Example 1, using 7β-[2-(2-aminothiazol-4-yl)-2(Z)-methoxyiminoacetamido]-3-(3-oxobutyryloxy) methyl-3-cephem-4-carboxylic acid and 7-methyl-5-mercaptoimidazo[1,2-a]pyrimidine, the title compound is obtained.

Elemental analysis for $C_{21}H_{18}N_8O_5S_3Na \cdot 5H_2O$: Calcd.(%): C, 37.55; H, 4.20; N, 16.68; Found (%): C, 37.34; H, 3.96; N, 16.63.

IR$\nu_{max}^{KBr}$cm$^{-1}$: 1760, 1665, 1605, 1530.

NMR(d$_6$-DMSO)δ: 2.58(3H,s), 3.61(2H×½, a half of ABq,J=18 Hz), 3.83(3H,s), 4.28 & 4.65(2H,ABq,J=13 Hz), 5.01(1H,d,J=4.5 Hz), 5.59(1H,d.d, J=4.5 Hz & J=8 Hz), 6.71(1H,s), 6.88(2H,br-s), 7.54(1H,d,J=2 Hz), 7.69(1H,d,J=2 Hz), 9.41 (1H,d,J=8 Hz).

EXAMPLE 9

Pivaloyloxymethyl 7β-[2-(2-aminothiazol-4-yl)-2(Z)-methoxyiminoacetamido]-3-[(imidazo[1,2-a]pyridin-5-yl)thiomethyl]-3-cephem-4-carboxylate

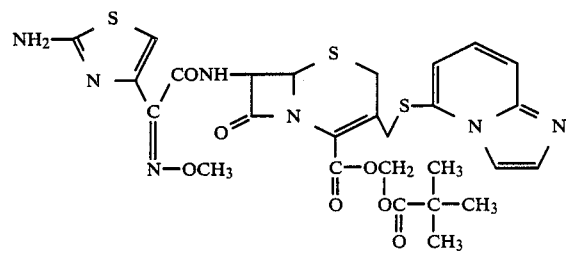

Sodium 7β-[2-(2-aminothiazol-4-yl)-2(Z)-methoxyiminoacetamido]-3-[(imidazo[1,2-a]pyridin-5-yl)thiomethyl]-3-cephem-4-carboxylate (200 mg) is suspended in 2 ml of dimethylformamide. To the mixture is added 112 mg of pivaloyloxymethyliodide under ice-cooling and stirred for 20 minutes.

To the reaction solution are added 100 ml of an aqueous saturated sodium chloride solution and 100 mg of ethyl acetate. The separated organic layer is washed with an aqueous saturated sodium chloride solution and then dried over magnesium sulfate. The solvent is evaporated off under reduced pressure and the residue is powdered by addition of a small amount of ethyl ether. The powder is collected by filtration and dried to give 160 mg of the title compound. Yield: 79%.

NMR(DMSO-d$_6$)δ: 1.14(9H,s), 4.00(3H,s), 4.22(2H,br.s), 5.20 (1H,d,J=5 Hz), 5.77(1H,m), 6.47(1H,s), 7.46 (2H,br.s), 7.6–8.7(5H,m), 9.34(1H,d,J=8 Hz).

Acetoxymethyl 7-[2-(2-aminothiazol-4-yl)-2(Z)-methoxyiminoacetamido]-3-[(imidazo[1,2-a]pyridin-5-yl)thiomethyl]-3-cephem-4-carboxylate

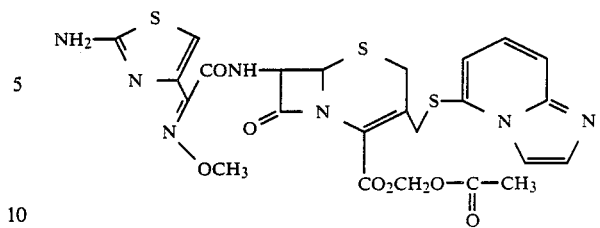

In a similar way to Example 9, using sodium 7β-[2-(2-aminothiazol-4-yl)thiomethyl]-3-cephem-4-carboxylate and 1-iodomethyl acetate, the title compound is obtained.

Elemental analysis for $C_{24}H_{23}N_7O_7S_3 \cdot 3/2H_2O$: Calcd.(%): C, 44.71; H, 4.06; N, 15.21; Found (%): C, 45.03; H, 4.43; N, 14.98.

IR$\delta_{max}^{KBr}$cm$^{-1}$: 1780, 1760, 1660, 1520.

NMR(d$_6$-DMSO)δ: 2.00(3H,s), 3.83(3H,s), 4.00 & 4.27(2H,ABq, J=13 Hz), 5.15(1H,d,J=4.5 Hz), 5.6–5.9(3H,m), 6.73(1H,s), 6.95–7.35(4H,m), 7.5–7.85(m,2H), 8.13(1H,s), 9.58(1H,d,J=8 Hz).

EXAMPLE 11

1-Acetoxyethyl 7β-[2-(2-aminothiazol-4-yl)-2(Z)-methoxyiminoacetamido]-3-[(imidazo[1,2-a]pyridin-5-yl)thiomethyl-cephem-4-carboxylate

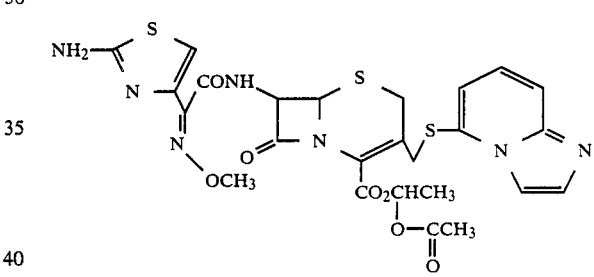

In a similar way to Example 9, using sodium 7β-[2-(2-aminothiazol-4-yl)-2(Z)-methoxyiminoacetamido]-3-[(imidaz [1,2-a]pyridin-5-yl)thiomethyl]-3-cephem-4-carboxylate and 1-iodoethyl acetate, the title compound is obtained.

Elemental analysis for $C_{25}H_{25}N_7O_7S_3 \cdot 2H_2O$: Calcd.(%): C,44.97; H,4.38; N,14.68; Found(%): C,44.59; H,3.88; N,14.96.

IR$\nu_{max}^{KBr}$cm$^{-1}$: 1775, 1760, 1625, 1520.

NMR(d$_6$-DMSO)δ: 1.45 & 1.47(2H,two d,J=6 Hz), 2.01 & 2.03 (3H,two s), 3.85(3H,s), 4.11(2H,br-s), 5.15 & 5.17(1H,two d,J=4.5 Hz), 5.5–6.0(1H,m), 6.60 & 6.62(1H,two d,J=6 Hz), 6.73(1H,s), 6.95–7.35 (4H,m), 7.4–7.8(1H,m),7.60 (1H,s), 8.05(1H,s), 9.60(1H,d,J=8 Hz).

We claim:
1. A compound of the formula

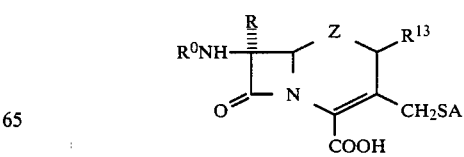

wherein R$^0$ is a group of the formula

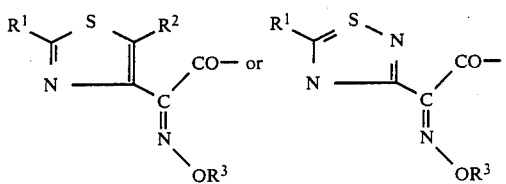

wherein R¹ is amino or an amino group which is protected by an amino protective group used in the field of β-lactams and peptides, R² is hydrogen, a halogen or nitro, R³ is hydrogen, a $C_{1-6}$ alkyl group which is unsubstituted or substituted by hydroxy, a $C_{1-6}$ alkoxy or a di-$C_{1-6}$ alkylamino, or a $C_{2-6}$ alkynyl group, Z is S or S→O, R⁴ is hydrogen, methoxy or formamido, R¹³ is hydrogen, methyl, hydroxyl or a halogen, and A is a condensed cyclic group selected from the group consisting of imidazo[1,2-a]-pyridyl, imidazo[1,2-a]pyrazinyl, imidazo[1,2-a]pyrimdinyl, imidazo[1,5-a]pyridyl and imidazo[1,5-a]-pyridazinyl group, which is unsubstituted or substituted by a $C_{1-6}$ alkyl group, the number of the substituent being 1 to 2, or pharmaceutically acceptable salt thereof or a metabolically unstable, nontoxic ester thereof.

2. A compound of claim 1 which is 7β-[2-(2-aminothiazol-4-yl)2-(Z)-methoxyiminocetamido]-3-[(imidazo[1,2-a]pyridin-5-yl)thiomethyl]-3-cephem-4-carboxylic acid, 7β-[2-aminothiazol-4-yl)-2(Z) - ethoxyiminoacetamido]-3-[(imidazo(1,2-a) pyridin-5-yl)thiomethyl]-3-cephem-4-carboxylic acid, 7β-[2-(2-aminothiazol-4-yl)-2(Z)-propargyloxyiminacetamido]-3-[(imidazo[1,2-a]pyridin-5-yl)thiomethyl]-3-cephem-4-carboxylic acid, 7β-[2-(2-aminothiazol-4-yl)-2(Z)-(2-methoxyethyiminoacetamido]-3-[(imidazo[1,2-a]pyridin-5-yl)thiomethyl]-3-cephem-4-carboxylic acid, 7β-[2-(2-aminothiazol-4-yl)-2-(Z)-(2-hydroxyethoxyiminoacetamido]-3-[(imidazo[1,2-a]pyridin-5-yl)thiomethyl]-3-cephem-3-carboxylic acid, 7β-[2-(2-aminothiazol-4-yl)-2-(Z)-(2-dimethylaminoethoxyiminoacetamido]-3-[(imidazo[1,2-a]pyridin-5-yl)thiomethyl]-3-cephem-4-carboxylic acid, 7β-[2-(2-aminothiazol-4-yl)-2(Z)-methoxyiminoacetamido]-3-[(imidazo[1,2-a]pyrazin-5-yl)thiomethyl]-3-cephem-4-carboxylic acid or 7β-[2-(2-aminothiazol-4-yl)-2(Z)-methoxyiminoacetamido]-3[(5-methylimidazo[1,2-a]pyrimidin-7-yl)thiomethyl]-3-cephem-4-carboxylic acid, or a pharmaceutically acceptable salt thereof or a metabolicallyunstable, nontoix ester thereof.

3. A compound of claim 1 in which the pharmaceutically acceptable salt is an alkali metal salt.

4. A compound of claim 1 in whihc the pharmaceutically acceptable salt is a sodium salt.

5. A compound of claim 1 in which the metabolically unstable, nontoxic ester is a $C_{2-6}$ alkanoyloxy $C_{1-6}$ alkyl ester.

6. A compound of claim 1 in which the metabolically unstable, nontoxic ester is pivaloyloxymethyl, acetoxymethyl or 1-(acetoxy) ethyl ester.

7. An antibacterial composition comprising an antibacterially effective amount of the compound of the formula

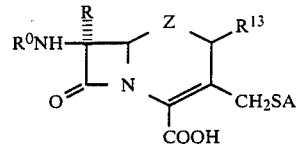

wherein the symbols are as defined in claim 1, or a pharmaceutically acceptable salt thereof or a metabolically unstable, nontoxic ester thereof and a pharmaceutically acceptable diluent or carrier.

8. An antibacterial composition of claim 7, which contains a compound which is

7β-[2-(2-aminothiazol-4-yl)2-(Z)-methoxyiminoacetamido]-3-[(imidazo[1,2-a]pyridin-5-yl)thiomethyl]-3-cephem-4-carboxylic acid, 7β-[2-aminothiazol-4-yl)-2-(Z)-ethoxyiminoacetamido]-3-[(imidazo[1,2-a]pyridin-5-yl)thiomethyl]-3-cephem-4-carboxylic acid, 7β-[2-(2-aminothiazol-4-yl)-2-(Z)-propargyloxyiminoacetamido]-3-[(imidazo[1,2-a)pyridin-5-yl)thiomethyl]-3-cephem-4-carboxylic acid, 7β-[2-(2-aminothiazol-4-yl)-2-(Z)-(2-methoxyethoxyiminoacetamido]-3-[(imidazo[1,2-a]pyrindin-5-yl)thiomethyl]-3-cephem-4-carboxylic acid, 7β-[2-(2-aminothiazol-4-yl)-2-(Z)-(2-hydroxyethoxyiminoacetamido]-3-[(imidazo[1,2-a]pyridin-5-yl)thiomethyl]-3-cephem-4-carboxylic acid, 7β-[2-(2-aminothiazol-4-yl)2(Z)-(2-dimethylaminoethoxyiminoacetamido]-3-[(imidazo[1,2-a]pyridin-5-yl)thiomethyl]-3-cephem-4-carboxylic acid, 7β-[2-(2-aminothiazol-4-yl)-2(Z)-methoxyiminoacetamido]-3-[(imidazo[1,2-a]pryazin-5-yl)thiomethyl]-3-cephem-4-carboxylic acid or 7β-[2-(2-aminothiazol-4-yl)-2(Z)-methoxyiminoacetamido]-3-[(5-methylimidazo[1,2-a]pyrimidin-7-yl)thiomethyl]-3-cephem-4-carboxylic acid, or a pharmaceutically acceptable salt thereof or a metabolically untable, nontoxic ester thereof.

9. An antibacterial composition of claim 7 in which the pharmaceutaically acceptable salt is an alkali metal salt.

10. An antibacterial composition of claim 7 in which the pharmaceutically acceptable salt is a sodium salt.

11. An antibaoterial composition of claim 7 which contains a metabolically unstable, nontoxic ester which is a $C_{2-6}$ alkanoyloxy $C_{1-6}$ alkyl ester.

12. An antibacterial composition of claim 7 in which the metabolically unstable, nontoxic ester is a pivaloyloxymethyl, acetoxymethyl or 1-(acetoxy)ethyl ester.

* * * * *